US007985748B2

(12) United States Patent
McCormick et al.

(10) Patent No.: US 7,985,748 B2
(45) Date of Patent: *Jul. 26, 2011

(54) ALPHA2C ADRENORECEPTOR AGONISTS

(75) Inventors: Kevin D. McCormick, Basking Ridge, NJ (US); Christopher W. Boyce, Flemington, NJ (US); Neng-Yang Shih, Lexington, MA (US); Robert G. Aslanian, Rockaway, NJ (US); Pietro Mangiaracina, Monsey, NY (US); Manuel de Lera Ruiz, Branchburg, NJ (US); Younong Yu, East Brunswick, NJ (US); Purakkattle Biju, Piscataway, NJ (US); Chia-Yu Huang, West Windsor, NJ (US); Bo Liang, Lawrenceville, NJ (US); Ruiyan Liu, Yardley, PA (US); Rong-Qiang Liu, Kendall Park, NJ (US); Lisa Guise-Zawacki, Yardley, PA (US)

(73) Assignees: Pharmacopeia Drug Discovery, Inc., Princeton, NJ (US); Scheeing Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/722,879

(22) Filed: Mar. 12, 2010

(65) Prior Publication Data
US 2010/0173823 A1 Jul. 8, 2010

Related U.S. Application Data

(63) Continuation of application No. 11/508,467, filed on Aug. 23, 2006, now abandoned.

(60) Provisional application No. 60/711,453, filed on Aug. 25, 2005.

(51) Int. Cl.
C07D 413/06 (2006.01)
A61K 31/538 (2006.01)

(52) U.S. Cl. ...................... 514/230.5; 544/105
(58) Field of Classification Search .................. 544/105; 514/230.5
See application file for complete search history.

(56) References Cited

U.S. PATENT DOCUMENTS

| 5,977,134 | A | 11/1999 | Ciccarone et al. | |
| 6,673,337 | B2 | 1/2004 | Olejnik et al. | |
| 7,700,592 | B2 * | 4/2010 | McCormick et al. | 514/230.5 |
| 2003/0087962 | A1 | 5/2003 | Demopulos et al. | |

FOREIGN PATENT DOCUMENTS

| WO | WO 97/12874 | 4/1997 |
| WO | WO 97/16727 A | 5/1997 |
| WO | WO 97/30992 | 8/1997 |
| WO | WO 99/28300 A | 6/1999 |
| WO | WO 01/00586 | 1/2001 |
| WO | WO 02/076950 | 10/2002 |
| WO | WO 03/099795 | 12/2003 |
| WO | WO 2004/050635 | 6/2004 |
| WO | WO 2005/089515 | 9/2005 |
| WO | WO 2007/024949 | 3/2007 |

OTHER PUBLICATIONS

R. P. Ahlquist, "A Study of the Adrenotropic Receptors", Am. J. Physiol., (1948), pp. 586-600, vol. 153. Arnold et al., "Differentiation of Receptor Systems Activated by Sympathomimetic Amines", Nature, (1967), pp. 597-598. vol. 214. Anderson et al., "Preparation of Water-Soluble Compounds Through Salt Formulation", The Practice of Medicinal Chemistry, Academic Press, New York (1996), pp. 739-754. Bagley et al., "Synthesis and Alpha 2 Adrenergic Activities of Imidazole and Imidazolidine Analogues, In Vitro and in Vivo Selectivity", Medicinal Chemistry Research, Birkahuser, Boston, US, (1994), pp. 346-364, vol. 4, No. 5. Berge et al., Journal of Pharmaceutical Salts, (1977), pp. 1-19, vol. 66 (1). Bousquet et al., "Role of the Ventral Surface of the Brain Stem in the Hypotensive Action of Clonidine", European Journal of Pharmacology, (1975), pp. 151-156, vol. 34. P. Bousquet et al., "Imidazoline Receptors: From Basic Concepts to Recent Developments", Journal of Cardiovascular Pharmacology. (1995), pp. S1-S6, vol. 26 (Suppl. 2). Chang et al., Microwave-Assisted Soluble Polymer-Supported Synthesis of Benzopiperazinones, Synlett, (2003), pp. 1688-1692, vol. 11. Feng et al., "One-Pot Regioselective Annulation Toward 3,4-Dihydro-3-Oxo-2H-1,4-Benzoxazine Scaffolds Under Controlled Microwave Heating", Tetrahedron. (2006), pp. 4635-4642, vol. 62. Gould et al., International Journal of Pharmaceutics (1986), pp. 201-217, vol. 33. Greene et al., Protective Groups in Organic Synthesis, (1991), Wiley, New York. T. Higuchi et al., "Pro-Drugs as Novel Delivery System", A.C.S. Symposium Series, (1975) vol. 14. Lands et al., "Differentiation of Receptor Systems Activated by Sympathomimetic Amines", Nature, (1976), pp. 597-598, vol. 214. Macdonald et al., "Gene Targeting-Homing in on Alpha2-Adrenoceptors-Subtype Function", TIPS, (1997), pp. 211-219, vol. 18. Michel et al., "Classification of Alpha 1-Adrenoceptor Subtypes", Naunyn-Schmiedeberg's Arch Pharmacol., (1995). pp. 1-10, vol. 352. Reis et al., "The Imidazoline Receptor Pharmacology, Functions, Ligands, and Relevance to Biology and Medicine", Annals of the New York Academy of Sciences, (1995), vol. 763, Table of Contents. Roche et al., Bioreversible Carriers in Drug Design, American Pharmaceutical Association and Pergamon Press, (1987). Written Opinion of the International Searching Authority for PCT/US2008/001778)-AL06356-01, 10 Pages, (2008). International Search Report (PCT/US2008/001776) for AL06356-01 mail date Feb. 7, 2008, 6 pages, (2008). Written Opinion of the International Searching Authority for (PCT/US2006/032917)-AL06356, 8 pages, (2006).
International Search Report (PCT/US2006/032917) for AL06356 mail date Mar. 20, 2007, 7 pages, (2006).

* cited by examiner

*Primary Examiner* — Kahsay T Habte
(74) *Attorney, Agent, or Firm* — Gerard Devlin; H. Eric Fischer

(57) ABSTRACT

In its many embodiments, the present invention relates to a novel class of phenylmorpholine and phenylthiomorpholine compounds useful as α2C adrenergic receptor agonists, pharmaceutical compositions containing the compounds, and methods of treatment, prevention, inhibition, or amelioration of one or more diseases associated with the α2C adrenergic receptor agonists using such compounds or pharmaceutical compositions.

15 Claims, No Drawings

ALPHA2C ADRENORECEPTOR AGONISTS

RELATED APPLICATIONS

This application claims priority to provisional application U.S. Ser. No. 60/711,453, filed on Aug. 25, 2005, herein incorporated by reference.

FIELD OF THE INVENTION

The present invention relates to phenylmorpholine and phenylthiomorpholine compounds useful as α2C adrenergic receptor agonists, pharmaceutical compositions containing the compounds, and methods of treatment and prevention using the compounds and compositions to treat disease states such as congestion (including nasal congestion), migraine, congestive heart failure, cardiac ischemia, pain, glaucoma, and psychotic disorders without substantial adverse side effects associated with α2A receptor agonist treatments.

BACKGROUND OF THE INVENTION

The initial classification of adrenergic receptors into α- and β-families was first described by Ahlquist in 1948 (Ahlquist R P, "A Study of the Adrenergic Receptors," Am. J. Physiol. 153:586-600 (1948)). Functionally, the α-adrenergic receptors were shown to be associated with most of the excitatory functions (vasoconstriction, stimulation of the uterus and pupil dilation) and B-adrenergic receptors were implicated in vasodilation, bronchodilation and myocardial stimulation (Lands et al., "Differentiation of Receptor Systems Activated by Sympathomimetic amines," Nature 214:597-598 (1967)). Since this early work, α-adrenergic receptors have been subdivided into α1- and α2-adrenergic receptors. Cloning and expression of α-adrenergic receptors have confirmed the presence of multiple subtypes of both α1-(α1A, α1B, α1D) and α2-(α2A, α2B, α2C) adrenergic receptors (Michel et al., "Classification of $\alpha_1$-Adrenoceptor Subtypes," Naunyn-Schmiedeberg's Arch. Pharmacol, 352:1-10 (1995); Macdonald et al., "Gene Targeting—Homing in on $\alpha_2$-Adrenoceptor-Subtype Function," TIPS, 18:211-219 (1997)).

Current therapeutic uses of α2 adrenergic receptor drugs involve the ability of those drugs to mediate many of the physiological actions of the endogenous catecholamines. There are many drugs that act on these receptors to control hypertension, intraocular pressure, eye reddening and nasal congestion and induce analgesia and anesthesia.

α2 adrenergic receptors can be found in the rostral ventrolateral medulla, and are known to respond to the neurotransmitter norepinephrine and the antihypertensive drug clonidine to decrease sympathetic outflow and reduce arterial blood pressure (Bousquet et al., "Role of the Ventral Surface of the Brain Stem in the Hypothesive Action of Clonidine," Eur. J. Pharmacol., 34:151-156 (1975); Bousquet et al., "Imidazoline Receptors: From Basic Concepts to Recent Developments," 26:S1-S6 (1995)). Clonidine and other imidazolines also bind to imidazoline receptors (formerly called imidazoline-guanidinium receptive sites or IGRS) (Bousquet et al., "Imidazoline Receptors: From Basic Concepts to Recent Developments," 26:S1-S6 (1995)). Some researchers have speculated that the central and peripheral effects of imidazolines as hypotensive agents may be related to imidazoline receptors (Bousquet et al., "Imidazoline Receptors: From Basic Concepts to Recent Developments," 26:S1-S6 (1995); Reis et al., "The Imidazoline Receptor: Pharmacology, Functions, Ligands, and Relevance to Biology and Medicine," Ann. N.Y. Acad. Sci., 763:1-703 (1995).

Compounds which have adrenergic activity are well known in the art, and are described in numerous patents and scientific publications. The two main families of adrenergic receptor are termed alpha adrenergic receptors and beta adrenergic receptors in the art, and each of these two families is known to have subtypes, which are designated by letters of the alphabet, such as α2A, α2B, and α2C. It is generally known that adrenergic activity is useful for treating animals of the mammalian species, including humans, for curing or alleviating the symptoms and conditions of numerous diseases and conditions. In other words, it is generally accepted in the art that pharmaceutical compositions having an adrenergic compound or compounds as the active ingredient are useful for treating, among other things, glaucoma, chronic pain, migraines, heart failure, and psychotic disorders. It is also known that compounds having adrenergic activity, such as α2A agonists, may be associated with undesirable side effects. Examples of such side effects include hyper- and hypotension, sedation, locomotor activity, and body temperature variations.

It has been discovered in accordance with the present invention that adrenergic compounds that act selectively, and preferably even specifically, as agonists of the α2C or the α2B/α2C (hereinafter referred to as α2C or α2B/2C) receptor subtypes in preference over the α2A receptor subtype, with adrenergic compounds that are functionally selective agonists of the α2C receptor subtype in preference over the α2A receptor subtype and α2B/2C receptor subtype, possess desirable therapeutic properties associated with adrenergic receptors but without having one or more undesirable side effects such as changes in blood pressure (e.g., a hypertensive or hypotensive effect) or sedation. For the purposes of this present invention, a compound is defined to be an active agonist of the α2C receptor subtype if the compound's efficacy at the α2C receptor is $\geq 30\%$ $E_{max}$ (GTPγS assay). A compound is a functionally selective agonist of the α2C receptor subtype over the α2A receptor subtype if the compound's efficacy at the α2C receptor is $\geq 30\%$ $E_{max}$ (GTPγS assay) and its efficacy at the α2A receptor is $\geq 30\%$ $E_{max}$ (GTPγS assay).

There is a need for new compounds, formulations, treatments and therapies to treat diseases and disorders associated with α2C adrenergic receptors. Furthermore, there is a need to develop compounds that are functionally selective for the α2C receptor subtype with respect to the α2A receptor subtype or the α2B/α2C receptor subtype. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds as active or functionally selective α2C adrenergic receptor agonists or metabolites, stereoisomers (e.g., enantiomers or diastereomers) salts, solvates or polymorphs thereof, methods of preparing such compounds, pharmaceutical compositions comprising one or more such compounds, methods of preparing pharmaceutical formulations comprising one or more such compounds, and methods of treatment, prevention, inhibition or amelioration of one or more conditions associated with α2C receptors using such compounds or pharmaceutical compositions.

In one aspect, the present application discloses a compound, or pharmaceutically acceptable salts or metabolites, solvates or polymorphs of said compound, said compound having the general structure shown in Formula I:

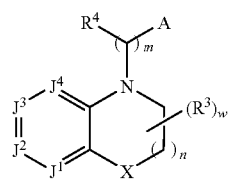

Formula I or a pharmaceutically acceptable salt or metabolite, solvate or polymorph of said compound, wherein:

A is a 5-membered heterocyclic ring containing 1-3 heteroatoms, and is substituted with at least one $R^5$;

X is —O—, —S(O)$_p$—, or —N($R^6$)—;

$J^1$, $J^2$, $J^3$, and $J^4$ are independently —N—, —N(O)— or —C($R^2$)—, provided that 0-3 of $J^1$, $J^2$, $J^3$ and $J^4$ are —N—;

$R^2$ is independently selected from the group consisting of H, —OH, halo, —CN, —NO$_2$, —(CH$_2$)$_q$Y$R^7$, —(CH$_2$)$_q$N$R^7$Y$R^{7'}$, —(CH$_2$)$_q$OY$R^7$, —(CH$_2$)$_q$ON=C$R^7R^{7'}$, —P(=O)(O$R^7$)(O$R^{7'}$), —P(=O)(N$R^7R^{7'}$)$_2$, —P(=O)$R^8_2$, and alkyl, alkoxy, alkenyl, alkynyl, cycloalkyl, aryl, arylalkyl, heteroaryl, heteroarylalkyl, and heterocyclyl groups optionally substituted with at least one $R^5$;

Y is selected from the group consisting of a bond, —C(=O)—, —C(=O)N$R^7$—, —C(=O)O—, —C(=N$R^7$)—, —C(=NO$R^7$)—, —C(=N$R^7$)N$R^7$—, —C(=N$R^7$)N$R^7$O—, —S(O)$_p$—, —SO$_2$N$R^7$—, and —C(S)N$R^7$—;

$R^3$ is independently selected from the group consisting of H and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$, provided that when n is 3 or 4, no more than 2 of the $R^3$ groups may be (=O);

$R^4$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^5$ is independently selected from the group consisting of H, halo, —OH, —CN, —NO$_2$, —N$R^7R^{7'}$, —S$R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —N$R^7R^{7'}$, and —S(O)$_p R^7$ substituents;

$R^6$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —N$R^7R^{7'}$, and —S$R^7$ substituents, and —C(=O)$R^7$, —C(=O)O$R^7$, —C(=O)N$R^7R^{7'}$, —SO$_2R^7$ and —SO$_2$N$R^7R^{7'}$;

$R^7$ is independently selected from the group consisting of H and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —S$R^{11}$ substituents;

$R^{7'}$ is independently selected from the group consisting of H and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —S$R^{11}$ substituents; or $R^7$ and $R^{7'}$ together with the nitrogen atom to which they are attached form a 3- to 8-membered heterocyclyl, heterocyclenyl or heteroaryl ring having, in addition to the N atom, 1 or 2 additional hetero atoms selected from the group consisting of O, N, —N($R^9$)— and S, wherein said rings are optionally substituted by 1 to 5 independently selected $R^5$ moieties, $R^8$ is independently selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —S$R^{11}$ substituents;

$R^9$ is independently selected from the group consisting of H, —C(O)—$R^{10}$, —C(O)—O$R^{10}$, and —S(O)$_p$—O$R^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —S$R^{11}$ substituents; and $R^{10}$ is selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —S$R^{11}$ substituents;

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

m is 1-5;

n is 1-3;

p is 0-2;

q is 0-6; and w is 0-4.

The compounds of Formula I can be useful as α2C adrenergic receptor agonists, and can be useful in the treatment and prevention of allergic rhinitis, all types of congestion (including, but not limited to nasal congestion), migraine, congestive heart failure, cardiac ischemia, glaucoma, and psychotic disorders. Further, the compounds of Formula I can be useful in the treatment of pain (both chronic and acute), such as pain that is caused by inflammation, neuropathy, arthritis (including rheumatoid arthritis, diabetes (e.g., diabetes mellitus or diabetes insipidus) or pain of an unknown origin. Other pain that can be treated is nociceptive pain and pain that is visceral in origin or pain that is secondary to inflammation or nerve damage in other diseases. Other utilities for the inventive compounds could include stress-induced urinary incontinence and neuronal damage from ischemia.

Alternatively, the present invention provides for a method for the treatment of congestion in a mammal in need thereof which comprises administering to a mammal an effective dose of at least one compound having adrenergic activity wherein said compound is a functionally selective agonist of the α2c receptor.

A further embodiment of the present invention is a method for the treatment of congestion in a mammal in need thereof which comprises administering to a mammal an effective dose of at least one compound having adrenergic activity wherein said compound is a selective agonist of the α2c adrenergic receptor, wherein the functional selective agonist of the α2c receptor has an efficacy that is greated than or equal to 30% $E_{max}$ when assayed in the GTPγS assay.

Another embodiment of the present invention is a method for the treatment of congestion in a mammal in need thereof without modifying the systemic blood pressure at therapeutic doses which comprises administering to the mammal an effective dose of at least one compound having adrenergic activity wherein said compound is a functionally selective agonist of the α2c receptor.

DETAILED DESCRIPTION

In an embodiment, the present invention discloses certain heterocyclic compounds which are represented by structural Formula I, or a pharmaceutically acceptable salt or solvate thereof, wherein the various moieties are as described above.

In another embodiment, if $J^1$-$J^4$ are each —C(H)—, n is 1, m is 1, $R^4$ is H, A is 1H-imidazol-4-yl, and X is —N($R^6$)—, then $R^6$ is not —C(=O)-naphthyl.

In another embodiment, if $J^1$-$J^4$ are each —C(H)—, n is 1, m is 1, $R^4$ is H, A is 1H-imidazol-4-yl, and X is —N($R^6$)—, then $R^6$ is not —S(O$_2$)-naphthyl.

In another embodiment, if $J^1$, $J^2$, and $J^4$ are each —C(H)—, $J^3$ is —C(Br)—, n is 2, m is 1, $R^3$ is 3-benzyl, $R^4$ is H, A is 1H-imidazol-4-yl, and X is —N($R^6$)—, then $R^6$ is not —C(O$_2$)benzyl.

In another embodiment, $J^1$-$J^4$ are each —C($R^2$)—, n is 1, A is imidazolyl, and X is —O—.

In another embodiment, $J^1$-$J^4$ are each —C(H)—, n is 1, A is imidazolyl, and X is —O—.

In another embodiment, $J^1$-$J^4$ are each —C($R^2$)—, n is 1, A is imidazolyl, and X is —N($R^6$)—.

In another embodiment, $J^1$-$J^4$ are each —C($R^2$)—, n is 1, A is imidazolyl, and X is —S(O)$_p$—.

In another embodiment, $R^2$ is independently selected from H, —OH, halo, —CN, —NO$_2$, —(CH$_2$)$_q$Y$R^7$, —(CH$_2$)$_q$NR$^7$YR$^{7'}$, —(CH$_2$)$_q$OY$R^7$, —(CH$_2$)$_q$ON=CR$^7$R$^{7'}$, —P(=O)(OR$^7$)(OR$^{7'}$), —P(=O)(NR$^7$R$^{7'}$)$_2$, —P(=O)R$^8$$_2$, alkyl, alkoxy and polyhaloalkoxy.

In another embodiment, $R^3$ is independently selected from H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$.

In another embodiment, $R^3$ is independently selected from H, alkyl and haloalkyl.

In another embodiment, $R^4$ is independently selected from H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$.

In another embodiment, $R^4$ is independently selected from H, alkyl, allyl, and haloalkyl.

In another embodiment, $R^5$ is independently selected from H, halo, —NR$^7$R$^{7'}$, —SR$^7$, alkyl, and alkoxy.

In another embodiment, $R^6$ is independently selected from H, alkyl, haloalkyl, cycloalkyl, —C(=O)R$^7$, —C(=O)OR$^7$, —C(=O)NR$^7$R$^{7'}$, —SO$_2$R$^7$ and —SO$_2$NR$^7$R$^{7'}$.

In another embodiment, $R^7$ is independently chosen from H, alkyl, haloalkyl, cycloalkyl, aryl, and heteroaryl.

In another embodiment, $R^{7'}$ is independently chosen from H, alkyl, haloalkyl, cycloalkyl, aryl, and heteroaryl.

In another embodiment, $R^7$ and $R^{7'}$ together with the N atom to which they are attached form a aziridine, azetidine, pyrrole, pyrrolidine, piperidine, piperazine or morpholine ring, each of which are optionally substituted by $R^5$.

In another embodiment, $R^8$ is independently chosen from alkyl, haloalkyl, cycloalkyl, aryl, and heteroaryl.

In another embodiment, m is 1 or 2.

In another embodiment, n is 1 or 2.

In another embodiment, n is 1.

In another embodiment, q is 0, 1, 2, or 3.

In another embodiment, the present invention discloses compounds which are represented by structural formulae II-V or a pharmaceutically acceptable salt, solvate or ester thereof, wherein the various moieties are as described above:

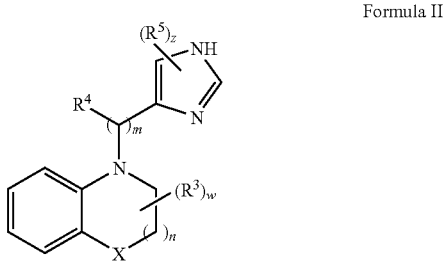

Formula II

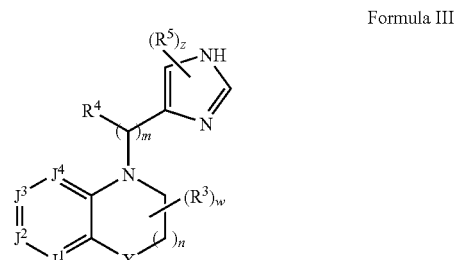

Formula III

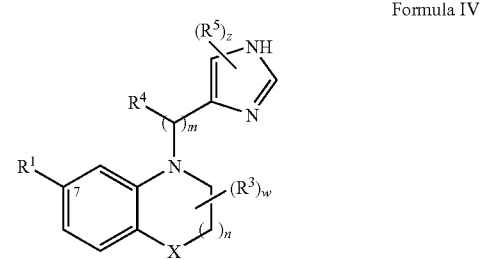

Formula IV

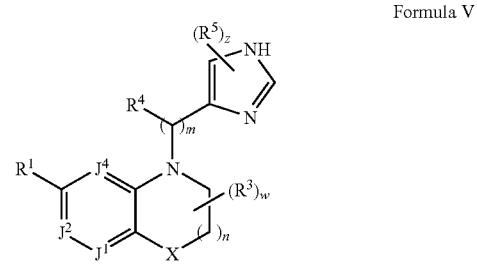

Formula V wherein z is 0-3 and $R^1$ is selected from the group consisting of H, —OH, halo, —CN, —NO$_2$, —SR$^7$, —(CH$_2$)$_q$YR$^7$, —(CH$_2$)$_q$NR$^7$YR$^{7'}$, —(CH$_2$)$_q$OYR$^7$, —(CH$_2$)$_q$ON=C NR$^7$R$^{7'}$, —P(=O)(OR$^7$)(OR$^{7'}$), —P(=O)(NR$^7$R$^{7'}$)$_2$, —P(=O)R$^8$$_2$ and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$.

An inventive group of compounds is shown in below:
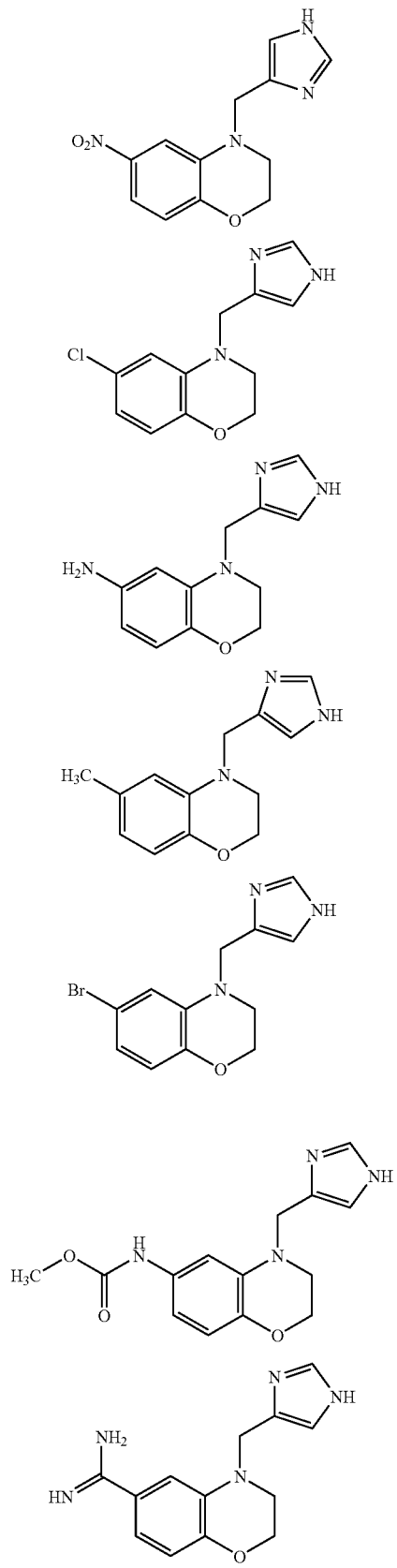
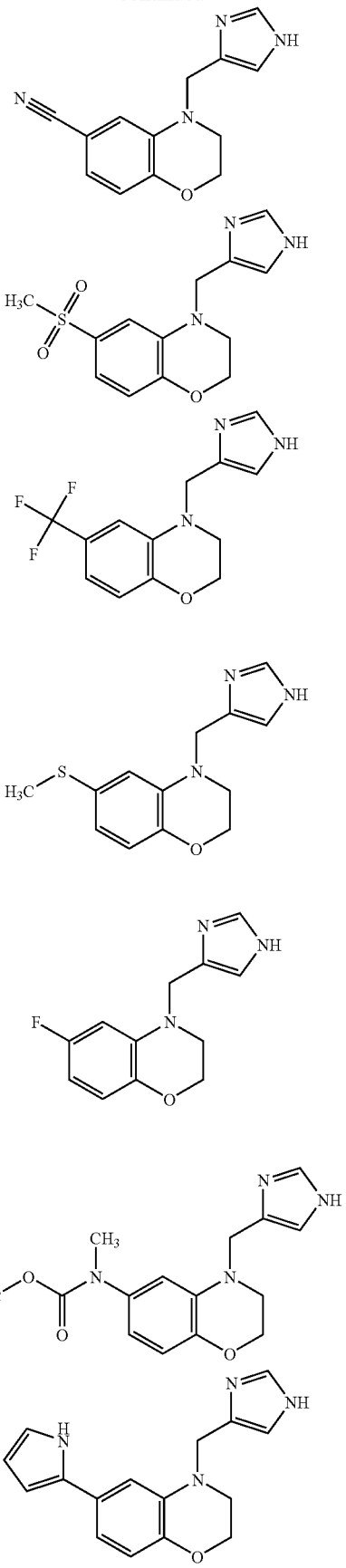

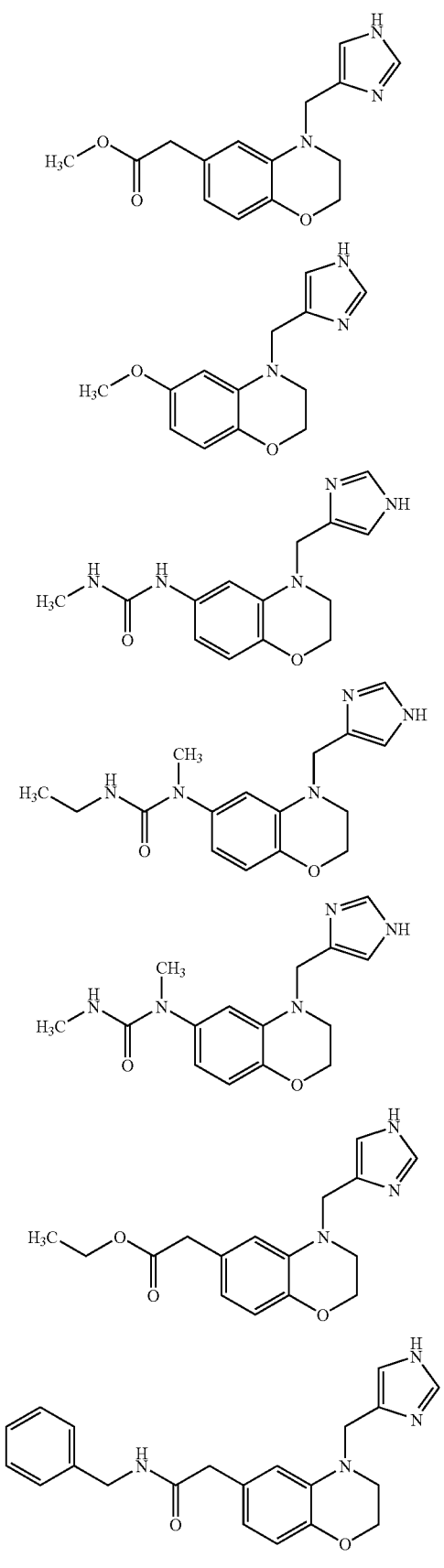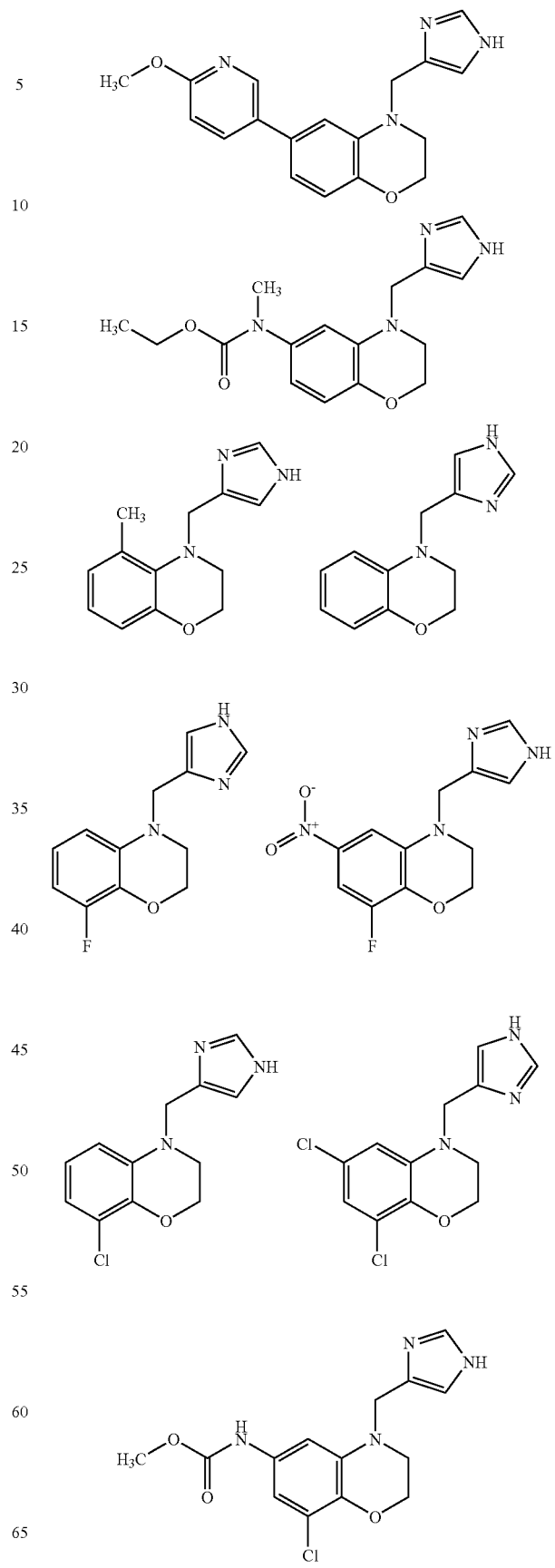

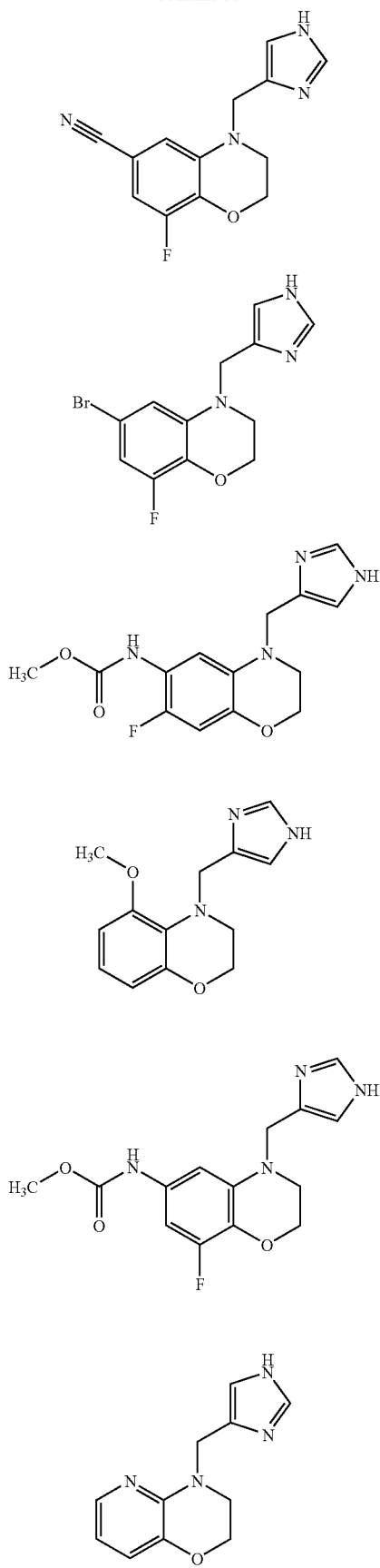
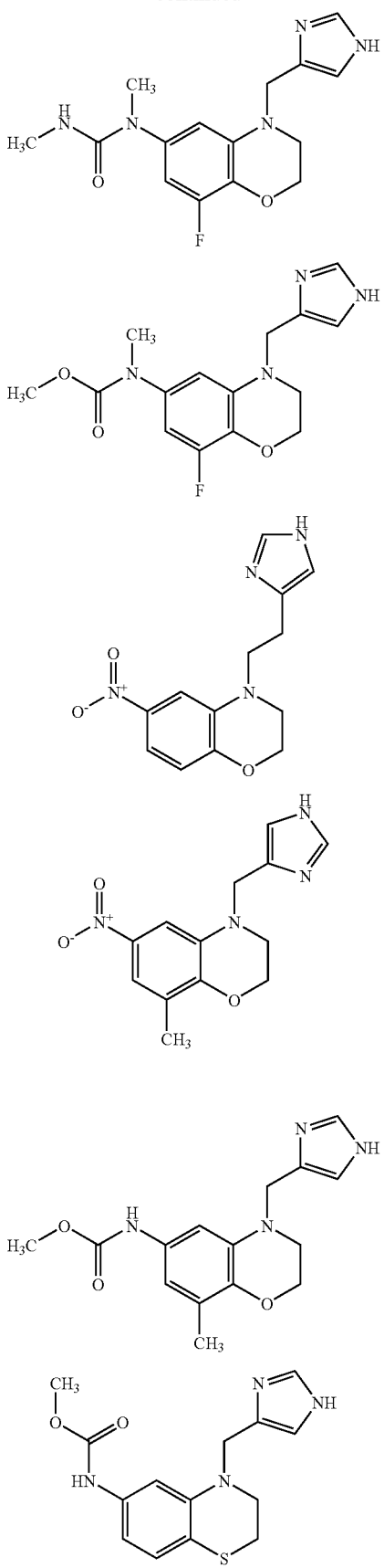

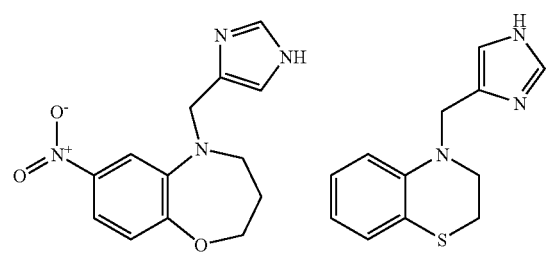
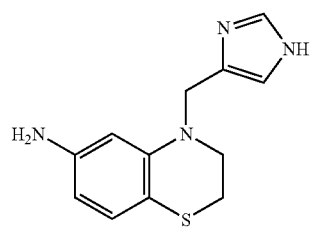
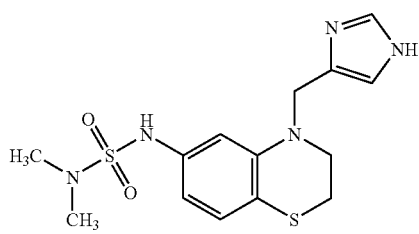
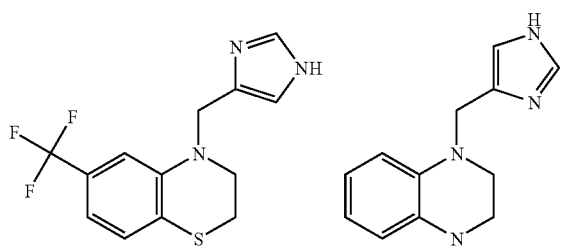
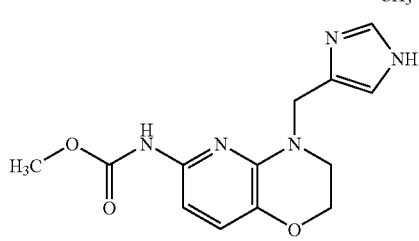
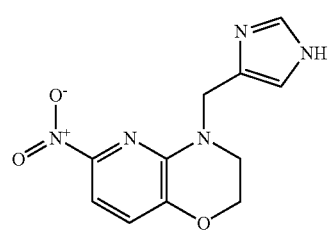
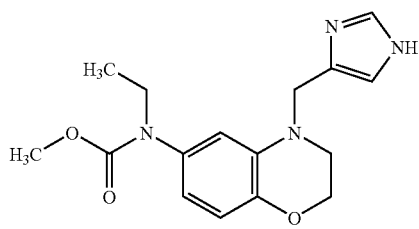
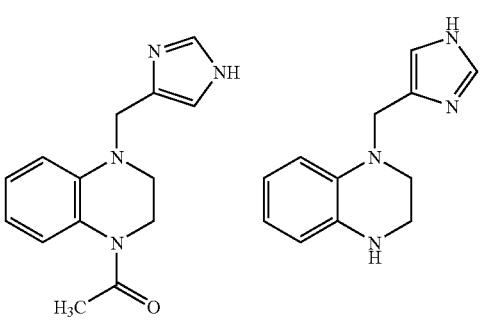
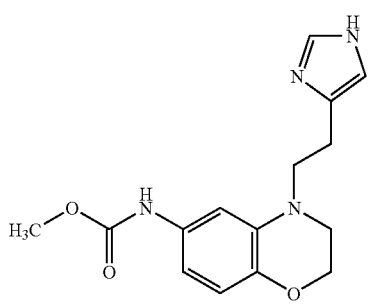
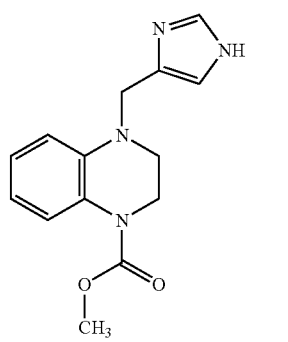
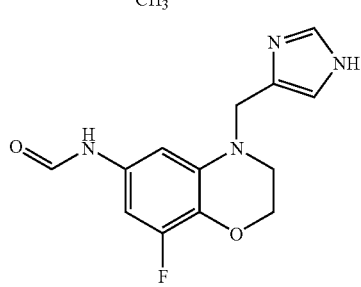
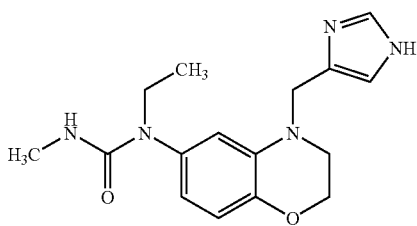
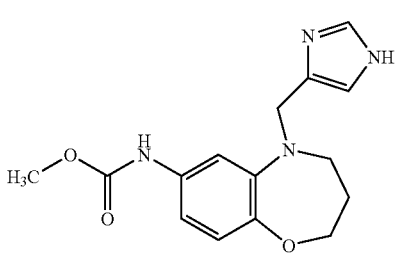

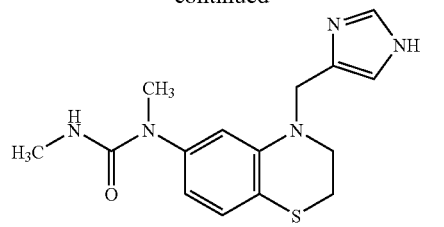
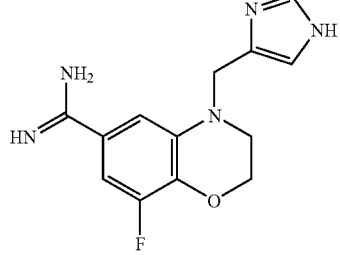
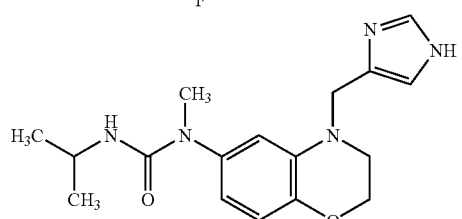
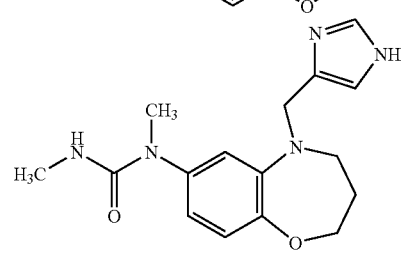
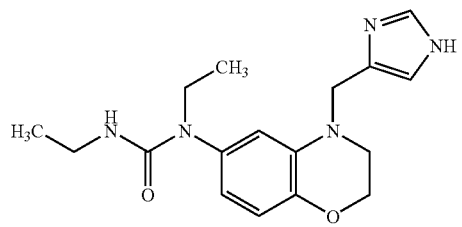
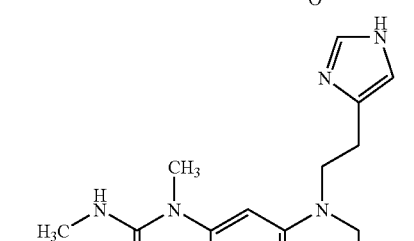
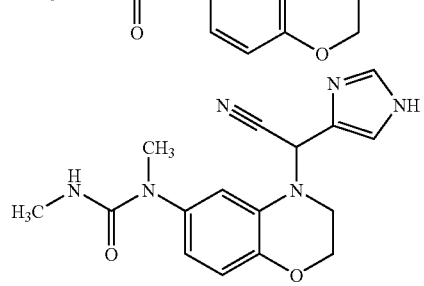
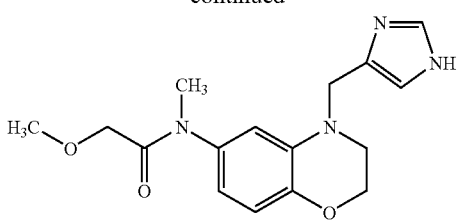
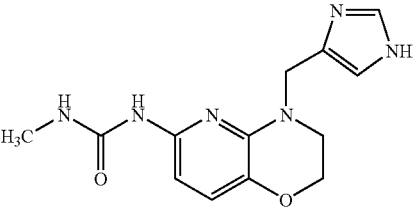
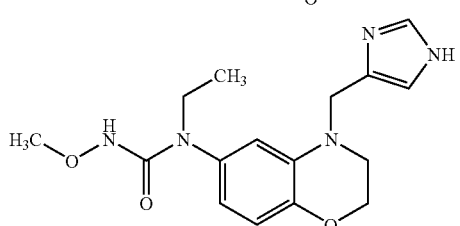
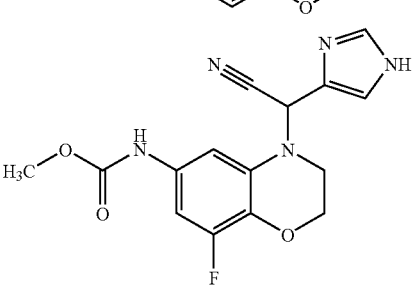
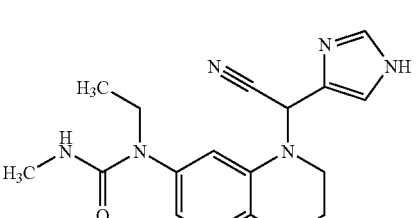
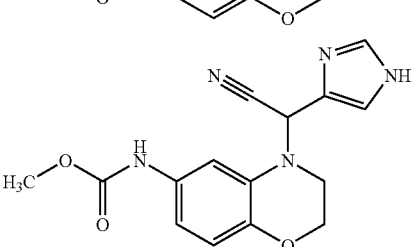
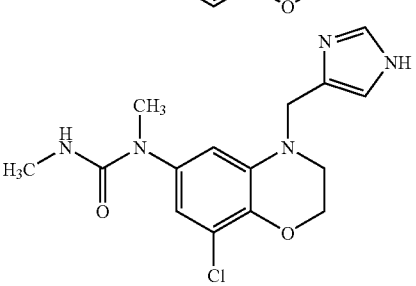

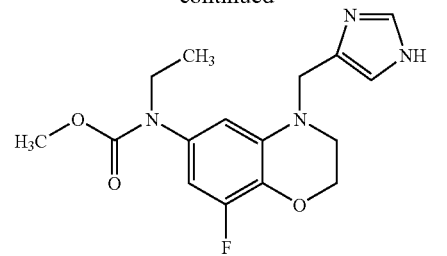
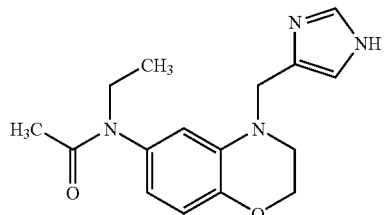
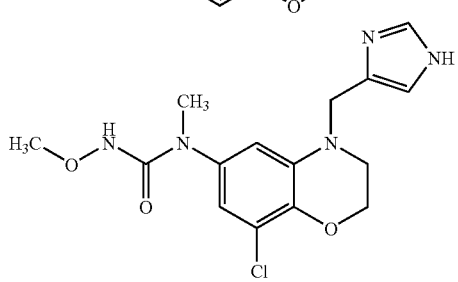
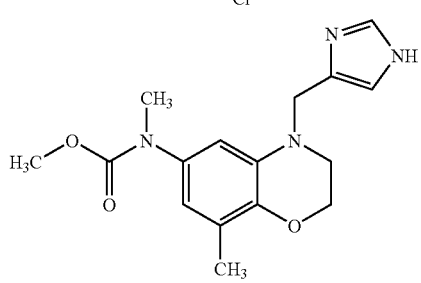
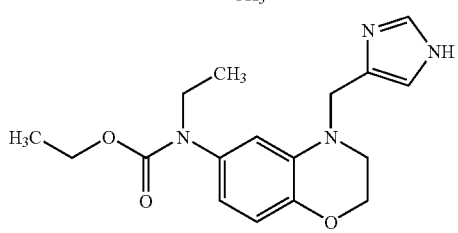
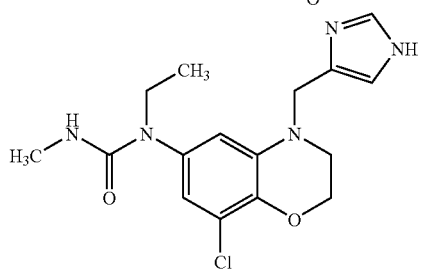
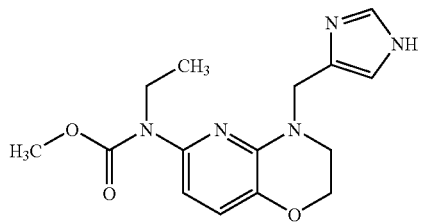
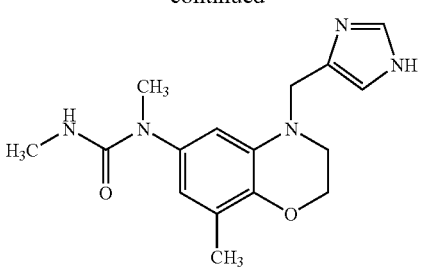
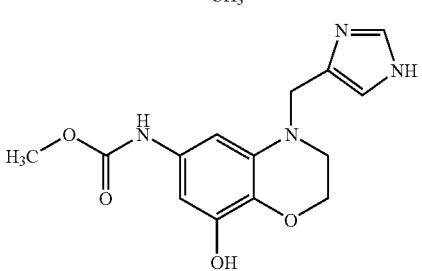
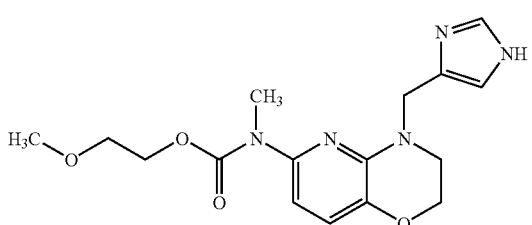
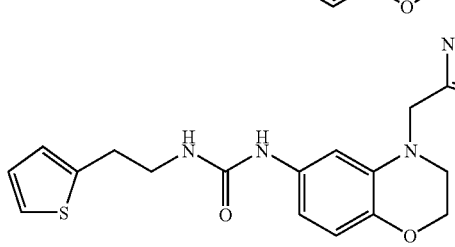
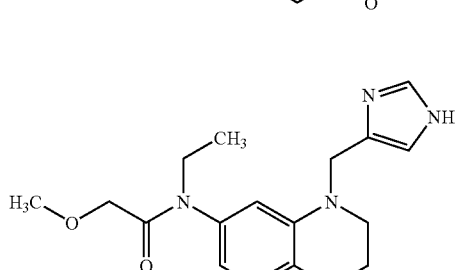
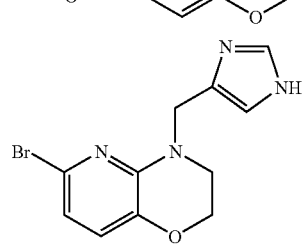
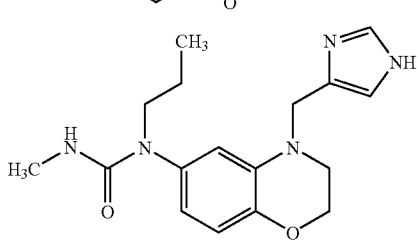

-continued

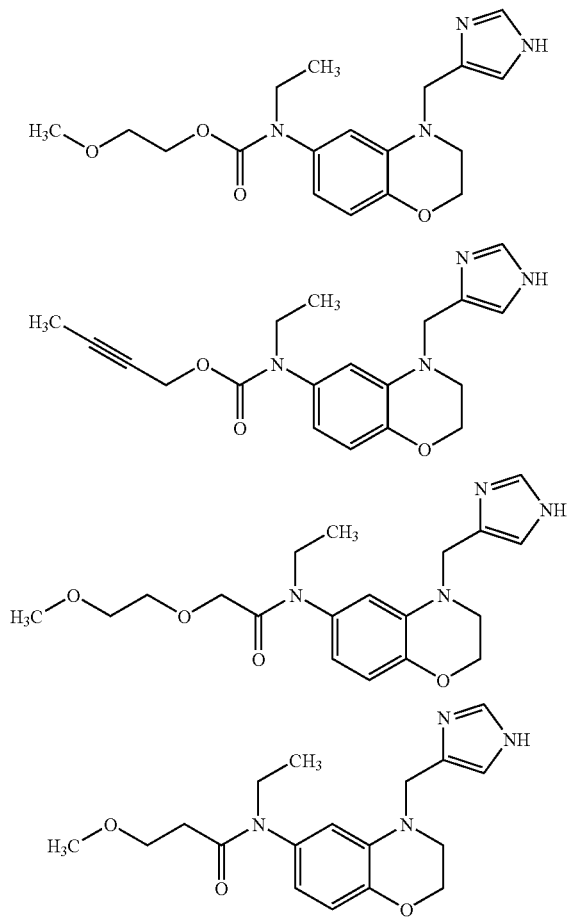

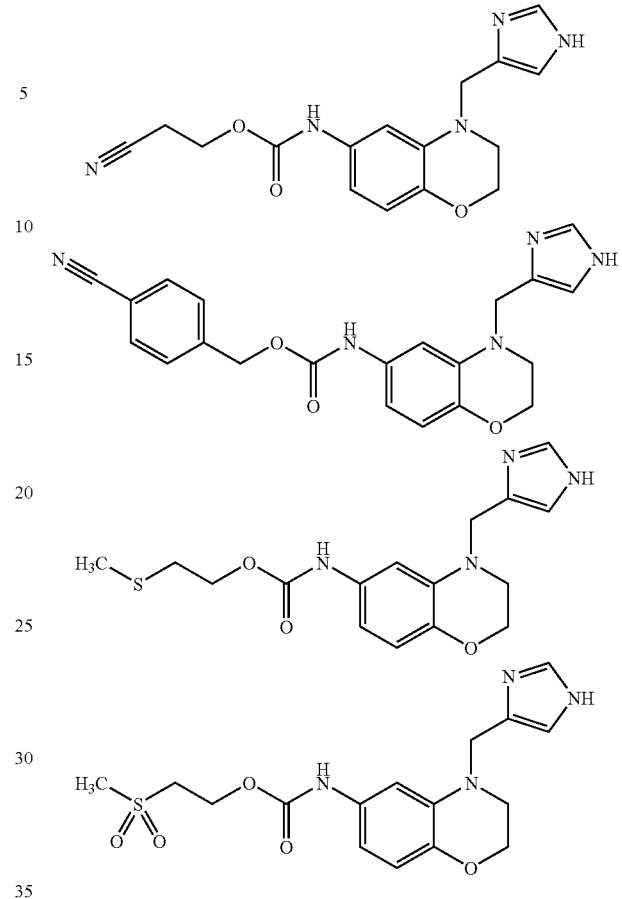

As used above, and throughout this disclosure, the following terms, unless otherwise indicated, shall be understood to have the following meanings:

"Patient" includes both human and animals.

"Mammal" means humans and other mammalian animals.

"Congestion" refers to all type of congestion including, but not limited to, congestion associated with perennial allergic rhinitis, seasonal allergic rhinitis, non-allergic rhinitis, vasomotor rhinitis, rhinitis medicamentosa, sinusitis, acute rhinosinusitis, or chronic rhinosinusitis or when the congestion is caused by polyps or is virally induced, such as congestion associated with the common cold.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" and "Halo" mean fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, and the like.

It should be noted that in heterocyclyl ring systems of this invention, there are no hydroxyl groups on carbon atoms adjacent to a N, O or S, as well as there are no N or S groups on carbon adjacent to another heteroatom. Thus, for example, in the ring:

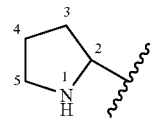

there is no —OH attached directly to carbons marked 2 and 5.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heterocyclylalkyl" means a heterocyclyl-alkyl group in which the heterocyclyl and the alkyl are as previously described. Preferred heterocyclylalkyls contain a lower alkyl group, Non-limiting examples of suitable heterocyclylalkyl groups include piperidylmethyl, piperidylethyl, pyrrolidylmethyl, morpholinylpropyl, piperazinylethyl, azindylmethyl, azetidylethyl, oxiranyipropyl and the like. The bond to the parent moiety is through the alkyl group.

"Heterocyclenyl" (or "heterocycloalkeneyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an organic acid group in which the —OH of the carboxyl group is replaced by some other substituent. Suitable non-limiting examples include H—C(O)—, alkyl-C(O)—, cycloalkyl-C(O)—, heterocyclyl-C(O)—, and heteroaryl-C(O)— groups in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

It is noted that carbons of formula I can be replaced with 1-3 silicon atoms, provided all valency requirements are satisfied.

The term "optionally substituted" means optional substitution with the specified groups, radicals or moieties.

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or formula, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$)alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula I incorporates a —NH— functional group, such as a in a primary or secondary amine or in a nitrogen-containing heterocycle, such as imidazole or piperazine ring, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino ($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

"Effective amount" or "therapeutically effective amount" is meant to describe an amount of compound or a composition of the present invention effective in producing the desired therapeutic, ameliorative, inhibitory or preventative effect.

"Capsule" is meant to describe a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet" is meant to describe a compressed or molded solid dosage form containing the active ingredients with suitable diluents. The tablet can be prepared by compression of mixtures or granulations obtained by wet granulation, dry granulation or by compaction.

"Oral gels" is meant to describe to the active ingredients dispersed or solubilized in a hydrophillic semi-solid matrix.

"Powders for constitution" refers to powder blends containing the active ingredients and suitable diluents which can be suspended in water or juices.

"Diluent" refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

"Disintegrants" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

"Binders" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

"Lubricant" is meant to describe a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

"Glidents" means materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

"Coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

"Bioavailability" refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula III contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons or sulfurs on various substituents, including enantiomeric forms (which may exist even in the absence of asymmetric carbons), rotameric forms, atropisomers, and diastereomeric forms, are contemplated within the scope of this invention. For example, if a compound of Formula (I) incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

Polymorphic forms of the compounds of formula I, and of the salts, solvates and prodrugs of the compounds of formula I, are intended to be included in the present invention The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^{3}H$, $^{11}O$ and $^{14}C$) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

The compounds according to the invention have pharmacological properties; in particular, the compounds of Formula I can be useful as α2C adrenoreceptor agonists.

A preferred dosage is about 0.001 to 500 mg/kg of body weight/day of the compound of Formula I. An especially preferred dosage is about 0.01 to 25 mg/kg of body weight/day of a compound of Formula I, or a pharmaceutically acceptable salt or solvate of said compound.

The compounds of this invention may also be useful in combination (administered together or sequentially) with one or more therapeutic agents such as, for example, steroids, PDE-4 inhibitors, anti-muscarinic agents, cromolyn sodium, $H_1$ receptor antagonists, 5-$HT_1$ agonists, NSAIDs, angiotensin-converting enzyme inhibitors, angiotensin II receptor agonists, β-blockers, β-agonists (including both short and long acting), leukotriene antagonists, diuretics, aldosterone antagonists, ionotropic agents, natriuretic peptides, pain management/analgesic agents, anti-anxiety agents, anti-migraine agents, and therapeutic agents suitable for treating heart conditions, psychotic disorders, and glaucoma.

Suitable steroids include prednisolone, fluticasone (including all esters such as the propionate or furoate esters), triamcinolone, beclomethasone, mometasone (including any ester form such as mometasone furoate), budasamine, ciclesonide, betamethasone, dexamethasone, prednisone, flunisolide, and cortisone.

Suitable PDE-4 inhibitors include roflumilast, theophylline, rolipram, piclamilast, cilomilast, and CDP-840.

Suitable antiimuscarinic agents include ipratropium bromide and tiatropium bromide.

Suitable $H_1$ antagonists include astemizole, azatadine, azelastine, acrivastine, brompheniramine, cetirizine, chlorpheniramine, clemastine, cyclizine, carebastine, cyproheptadine, carbinoxamine, descarboethoxyloratidine, diphenhydramine, doxylamine, dimethindene, ebastine, epinastine, efletirizeine, fexofenadine, hydroxyzine, ketotifen, loratidine, levocabastine, meclizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Suitable anti-inflammatory agents include aspirin, diclofenac, diflunisal, etodolac, flurbiprofen, ibuprofen, indomethacin, ketoprofen, ketorolac, nabumetone, naproxen, oxaprozin, piroxicam, sulindac, and tolmetin.

Suitable aldosterone antagonists include spironolactone.

Suitable ionotropic agents include digitalis.

Suitable angiotensin II receptor agonists include irbesartan and losartan.

Suitable diuretics include spironolactone, methyclothiazide, bumetanide, torsemide, hydroflumethiazide, trichlormethiazide, hydroclorothiazide, triamterene, ethacrynic acid, methyclothiazide, hydrochlorothiazide, benzthiazide, hydrochlorothiazide, quinethazone, hydrochlorothiazide, chlortha- lidone, furosemide, indapamide, hydroclorothiazide, triamterene, trichlormethiazide, hydrochlorothiazide, amiloride HCl, amiloride HCl, metolazone, trichlormethiazide, bendroflumethiazide, hydrochlorothiazide, polythiazide, hydroflumethiazide, chlorthalidone, and metolazone.

Suitable pain management/analgesic agents include Celecoxib, amitriptyline, ibuprofen, naproxen, gabapentin, tramadol, rofecoxib, oxycodone HCl, acetaminophenoxycodone HCl, carbamazepine, diclofenac, diclofenac, etodolac, fenoprofen calcium, flurbiprofen, ibuprofen, indomethacin, ketoprofen, ketorolac tromethamine, mefenamic acid, meloxicam, nabumetone, naproxen, oxaprozin, piroxicam, sulindac, tolmetin sodium, valdecoxib, diclofenac/misoprostol, oxycontin, vicodin, darvocet, morphine sulfate, dilaudid, stadol, stadol NS, acetaminophen with codeine, acetaminophen with codeine #4, Lidoderm® patches, and percocet.

Suitable β-blockers include acebutolol, atenolol, atenolol/chlorthalidone, betaxolol, bisoprolol fumarate, bisoprolol/HCTZ, labetolol, metoprolol tartrate, nadolol, pindolol, propranolol, propranolol/HCTZ, sotalol, and timolol.

Suitable β-agonists include dobutamine, ritodrine, salbutamol, levalbuterol, metaproternol, formoterol, fenoterol, bambuterol, brocaterol, clenbuterol, terbutaline, tulobuterol, epinephrine, isoprenalin, and hexoprenalin.

Suitable leukotriene antagonists include levamisole.

Suitable anti-migraine agents include rovatriptan succinate, naratriptan HCl, rizatriptan benzoate, sumatriptan succinate, zolmitriptan, almotriptan malate, methysergide maleate, dihydroergotamine mesylate, ergotamine tartrate, ergotamine tartrate/caffeine, Fioricet®, Fiorninal®, Depakene®, and Depakote®.

Suitable anti-anxiety and anti-depressant agents include amitriptyline HCl, bupropion HCl, citalopram hydrobromide, clomipramine HCl, desipramine, fluoxetine, fluvoxamine maleate, maprotiline HCl, mirtazapine, nefazodone HCl, nortriptyline, paroxetine HCl, protriptyline HCl, sertraline HCl, doxepin, and trimipramine maleate.

Suitable angiotensin converting enzyme inhibitors include Captopril, enalapril, enalapril/HCTZ, lisinopril, lisinopril/HCTZ, and Aceon®.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula I, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula I, or a pharmaceutically acceptable salt or solvate of said compound and a pharmaceutically acceptable carrier, vehicle or diluent.

Yet another aspect of this invention is a kit comprising an amount of at least one compound of Formula I, or a pharmaceutically acceptable salt or solvate of said compound and an amount of at least one therapeutic agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz), Varian Mercury VX-400 (400 MHz), or Bruker-Biospin AV-500 (500 MHz), and are reported as ppm with number of protons and multiplicities indicated parenthetically. Where LC/MS data are presented, analyses was performed using an Applied Biosystems API-100 mass spectrometer and C18 column, 10-95% $CH_3CN$—$H_2O$ (with 0.05% TFA) gradient. The observed parent ion is given.

The following solvents and reagents may be referred to by their abbreviations in parenthesis:
Me=methyl; Et=ethyl; Pr=propyl; Bu=butyl; Ph=phenyl, and Ac=acetyl
µl=microliters
AcOEt or EtOAc=ethyl acetate
AcOH or HOAc=acetic acid
ACN=acetonitrile
atm=atmosphere
Boc or BOC=tert-butoxycarbonyl
DOE=dichloroethane
DCM or $CH_2Cl_2$: dichloromethane:
DIPEA=diisopropylethylamine
DMAP=4-dimethylaminopyridine
DMF=dimethylformamide
DMS=dimethylsulfide
DMSO=dimethyl sulfoxide
EDCl=1-(3-dimethylaminopropyl)-3-ethylcarbodiimide
Fmoc=9-fluorenylmethoxycarbonyl
g=grams
h=hour
hal=halogen
HOBt=1-hydroxybenzotriazole
LAH=lithium aluminum hydride
LCMS=liquid chromatography mass spectrometry
min=minute
mg=milligrams
mL=milliliters
mmol=millimoles
MCPBA=3-chloroperoxybenzoic acid
MeOH=methanol
MS=mass spectrometry
NMR=nuclear magnetic resonance spectroscopy
RT or rt=room temperature (ambient, about 25° C.)
TEA or $Et_3N$=triethylamine
TFA=trifluoroacetic acid
THF=tetrahydrofuran
TLC=thin layer chromatography
TMS=trimethylsilyl
Tr=triphenylmethyl

EXAMPLES

The compounds of this invention can be prepared as generally described in Schemes 1 and 2, and the following examples. Scheme 1 shows an approach in which S1 and S2 are joined together. Examples of these approaches include reaction of SI with an electrophilic S2 compound, where R' is a carboxaldehyde (coupling by reductive amination), carboxylic acid (amide coupling) or halide (coupling by alkylation).

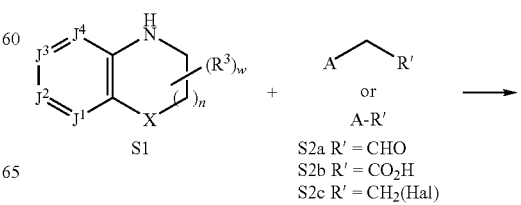

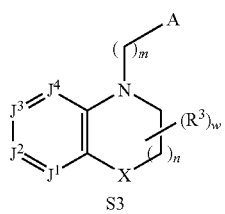

X = N, O, or S

Scheme 2 discloses a general approach for synthesizing S1, whereby an appropriately substituted aniline S4 can be converted to S1 through a single or multistep ring cyclization approach.

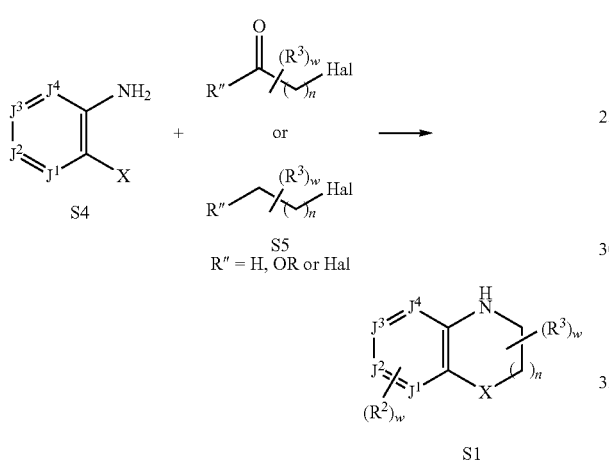

Compounds of formula S3 can be prepared by the general methods outlined above. Specifically exemplified compounds were prepared from S4 or S1 fragments as described in the examples below or from starting materials known in the art.

The starting materials and reagents used in preparing compounds described are either available from commercial suppliers such as Aldrich Chemical Co. (Wisconsin, USA) and Acros Organics Co. (New Jersey, USA) or were prepared by literature methods known to those skilled in the art. These examples are being provided to further illustrate the present invention. They are for illustrative purposes only; the scope of the invention is not to be considered limited in any way thereby.

Preparative Example 1

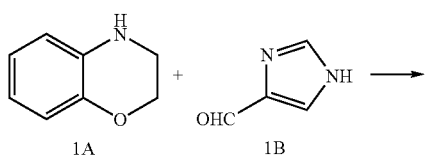

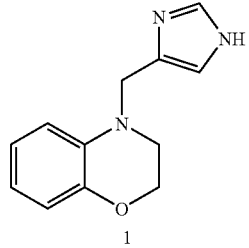

A solution of 3,4-dihydro-2H-1,4-benzoxazine 1A (0.1 g, 0.75 mmol) in DCE (10 mL) was treated with imidazole-4-carboxaldehye 1B (0.11 g, 1.1 mmol), NaBH(OAc)$_3$ (0.47 g, 2.2 mmol), and AcOH (one drop) and stirred at 60° C. overnight. The reaction was then diluted with CH$_2$Cl$_2$, washed with saturated aqueous NaHCO$_3$, dried over Na$_2$SO$_4$, and concentrated. Chromatography (0-4% 7 N NH$_3$-MeOH/ CH$_2$Cl$_2$) provided 1 as a beige solid (0.08 g, 50%). LMCS m/z 216 (MH+).

Alternatively, the title compound 1 can be synthesized by the reaction of 1A and resin bound imidazole-4-carboxaldehye 1D as described below:

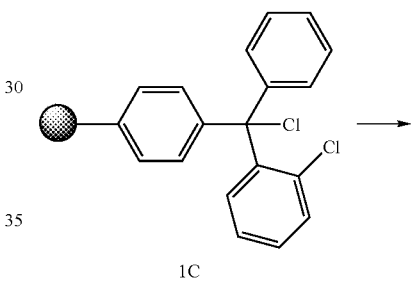

Novabiochem Resin 1C (100-200 mesh, 1% DVB, 1.4 mmol/g, 5 g) was suspended in anhydrous DMF (25 mL) and DCE (25 mL) and treated sequentially with 1B (2 g, 21 mmol) and TEA (2.96 mL, 21 mmol). The resin was shaken overnight and washed with DMF (3×), MeOH (3×), and DCM (4×) then dried in vacuo overnight. The resulting resin 1D (100 mg, 1.4 mmol/g, 0.14 mmol) was suspended in DCE (4 mL) and treated with 1A (94.5 mg, 0.7 mmol) and NaBH (OAc)$_3$ (148 mg, 0.7 mmol). The reaction was shaken overnight and washed with DMF (3×), MeOH (3×), and DCM (4×), then dried in vacuo. The resulting resin was subjected to 30% TFA/DCM, stirred at RT for 2 h and the mixture was concentrated under vacuum. The residue was purified by Gilson prep-HPLC to afford compound 1 (12.3 mg).

Preparative Example 2

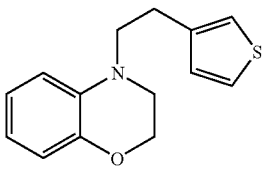

2

Step 1

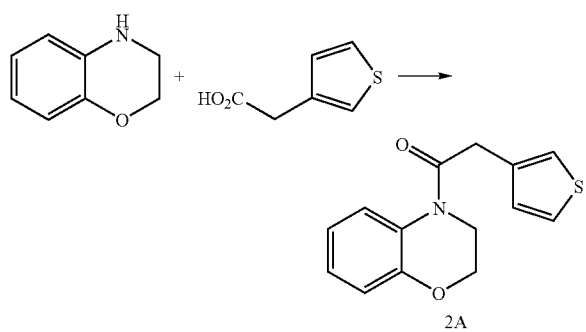

2A

A solution of 3,4-dihydro-2H-1,4-benzoxazine (0.52 g, 3.8 mmol) and thiophene-3-acetic acid (0.82 g, 5.7 mmol) in 1:1 CH$_2$Cl$_2$:DMF (20 mL) was treated with DIPEA (2.6 ml, 15 mmol), HOBt (1.29 g, 9.5 mmol), and EDCl (1.83 g, 9.5 mmol) and stirred at 70° C. overnight. The reaction was then diluted with CH$_2$Cl$_2$, washed with saturated aqueous NaHCO$_3$, dried over Na$_2$SO$_4$, and concentrated. Chromatography (0-10% 1 N NH$_3$-MeOH/EtOAc) provided 2A as a red solid (0.54 g, 55%)

Step 2

A solution of 2A (0.094 g, 0.36 mmol) in THF (10 mL) was treated with BH$_3$—SMe$_2$ (2M/THF, 0.27 mL, 0.54 mmol) and stirred at reflux for 2 h. The reaction was concentrated and subjected to chromatography (EtOAc) to provide 2 as a white solid (0.040 g, 45%). LMCS m/z 246 (MH+).

Preparative Example 3

3

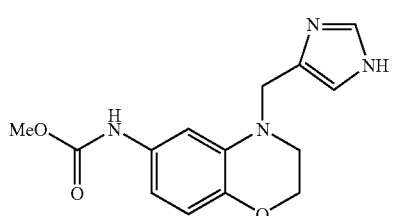

Step 1

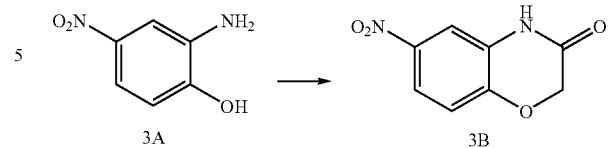

A mixture of 2-amino-4-nitrophenol (3A, 25.03 g, 0.16 mol) in 4-methyl-2-pentanone and water (420 mL, 1:1) was treated with sodium bicarbonate (32.74 g, 0.39 mol), cooled to 0° C., and treated then with chloroacetyl chloride (15.52 mL, 0.19 mol). The reaction mixture was heated to reflux overnight. After cooling to RT, the mixture was concentrated under vacuum. The residue was diluted with water (200 mL) and EtOAc (100 mL), and filtered to give the pale gray solid 3B (26.05 g). The filtrate was separated and the aqueous was extracted with EtOAc (3×100 mL). The combined organic layers were washed with water, and dried (MgSO$_4$), filtered, and concentrated under vacuum to give additional light gray solid 3B (7.7 g). The resulting solid (quantitative yield) was used for next reaction without further purification.

Step 2

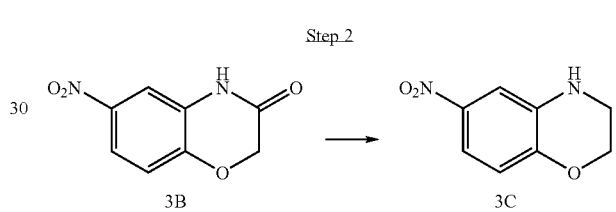

To compound 3B (6.76 g, 34.84 mmol) in anhydrous THF (200 mL) was added BH$_3$-SMe$_2$ (2.0M/THF, 35 mL, 69.68 mmol). The mixture was heated to reflux for 2 h. After cooling to RT, the mixture was quenched with MeOH (10 ml) and heated to reflux for another 10 minutes. The reaction mixture was concentrated under vacuum. Chromatography (10%-30% EtOAc/hexanes) provided 3C (6.1 g, 97% for two steps).

Step 3

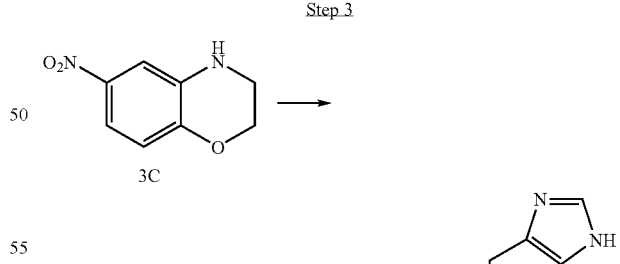

A mixture of 3C (4.35 g, 21.16 mmol) in anhydrous dichloroethane (60 mL) was treated with imidazole-4-carboxaldehye (1B, 2.79 g, 28.99 mmol) and AcOH (0.35 mL, 6 mmol). The mixture was stirred at RT for 10 min and then treated with NaBH(OAc)$_3$ (15.36 g, 72.48 mmol). The reaction mixture was stirred at RT overnight, and quenched with 2N NaOH solution, concentrated under vacuum. The residue was diluted with water (50 mL) and extracted with EtOAc (4×100 mL). The organic layer was dried (MgSO$_4$), filtered, and concentrated under vacuum. Chromatography (DCM containing 1 to 5% of 7N NH$_3$ in MeOH) provided 3D (5.56 g, 89%). MS m/z 261 (MH+).

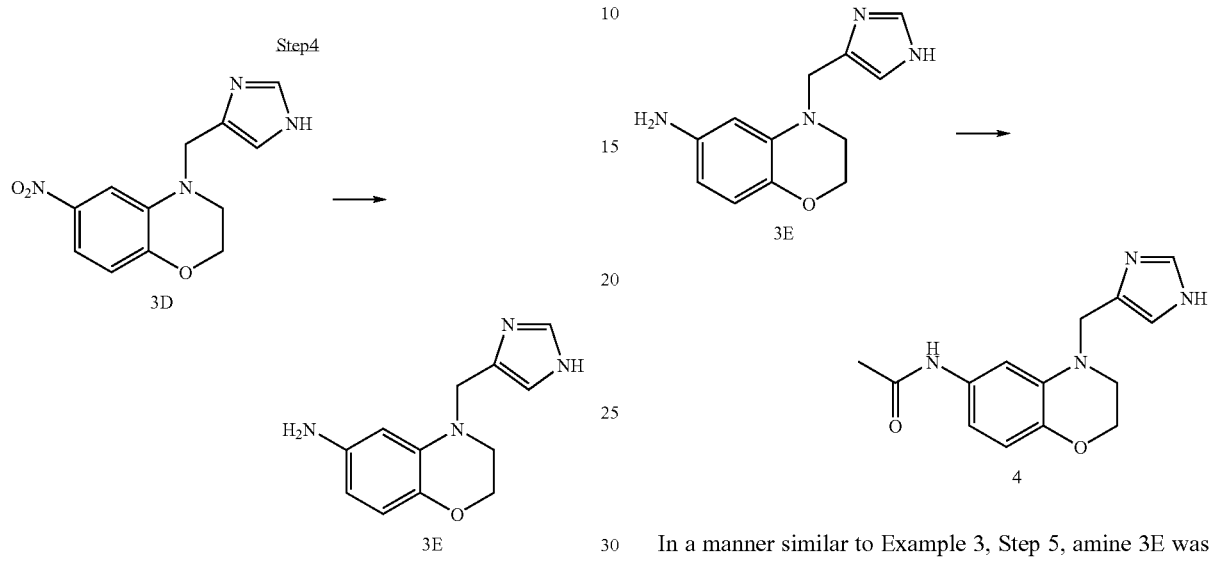

Compound 3D (5.56 g, 21.38 mmol) was dissolved in MeOH/EtOAc (300 mL, 1:1), 10% Pd/C (1.11 g, 20% by weight) was carefully added. The mixture was stirred at RT under a hydrogen balloon overnight and filtered. The solvent was evaporated off under vacuum to give a white solid 3E (5.46 g, 100%). MS m/z 231 (MH+).

A mixture of amine 3E (2.14 g, 9.30 mmol) in anhydrous DCM (40 mL) was sequentially treated with TEA (3.24 mL, 23.3 mmol) and ClCO$_2$Me (1.43 mL, 18.6 mmol). The mixture was stirred at RT for 2 h, and then quenched with 2N NaOH solution. The resulting mixture was stirred for another 2 h and separated. The aqueous layer was extracted with DCM (3×50 mL). The combined organic layers were dried (MgSO$_4$), filtered, and concentrated under vacuum. Chromatography (DCM containing 1 to 4% of 7N NH$_3$/MeOH) provided 3 as a white solid (1.64 g, 61%). MS m/z 289 (MH+).

Preparative Example 4

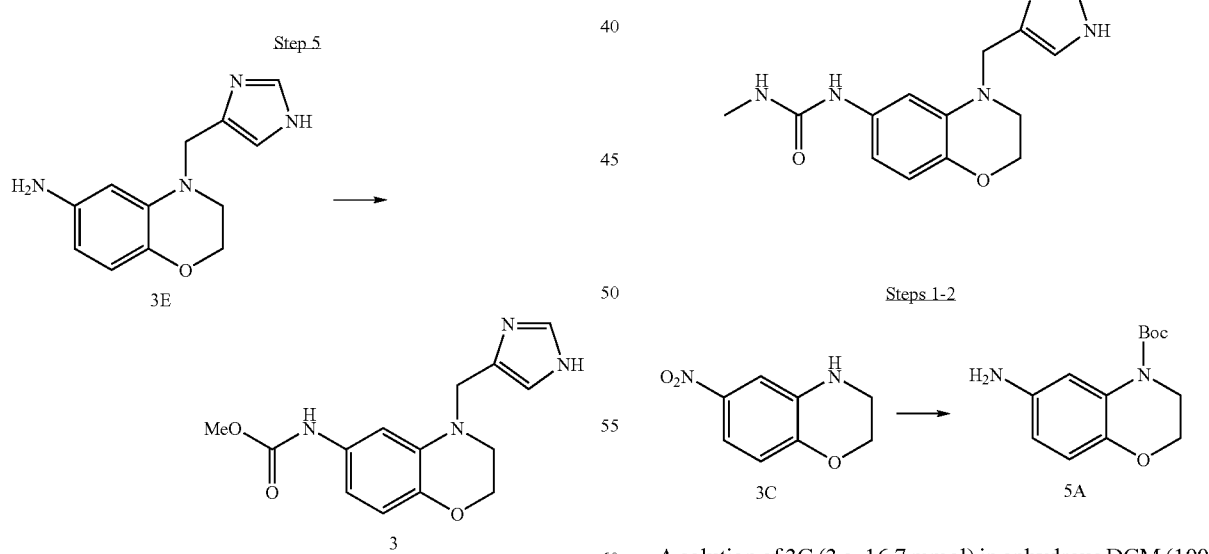

In a manner similar to Example 3, Step 5, amine 3E was treated with TEA and AcCl to provide the compound 4. MS m/z 273 (MH+).

Preparative Example 5

A solution of 3C (3 g, 16.7 mmol) in anhydrous DCM (100 mL) was treated with Boc$_2$O (7.27 g, 33.3 mmol), pyridine (5.39 mL, 66.7 mmol), and catalytic DMAP. The mixture was stirred at RT overnight and concentrated under vacuum. The residue was diluted with water (50 mL) and extracted with EtOAc (3×100 mL). The combined organic layers were dried (MgSO$_4$), concentrated and subjected to chromatography (5-5% EtOAc/hexanes, yield: 3 g, 64%).

The resulting product was hydrogenated in a manner similar to that found in Example 3, Step 4 to provide 5A.

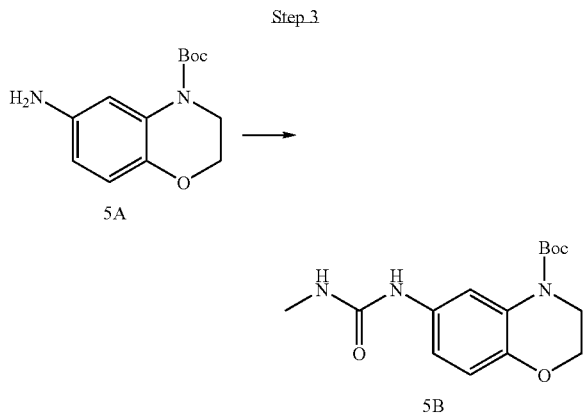

To amine 5A (1.1 g, 4.4 mmol) in anhydrous THF (15 mL) was added MeNCO (215 mg, 4.4 mmol). The mixture was stirred at RT overnight and then concentrated. Chromatography (DCM containing 1 to 5% of 7N NH$_3$/MeOH) provided 5B (890 mg, 66%).

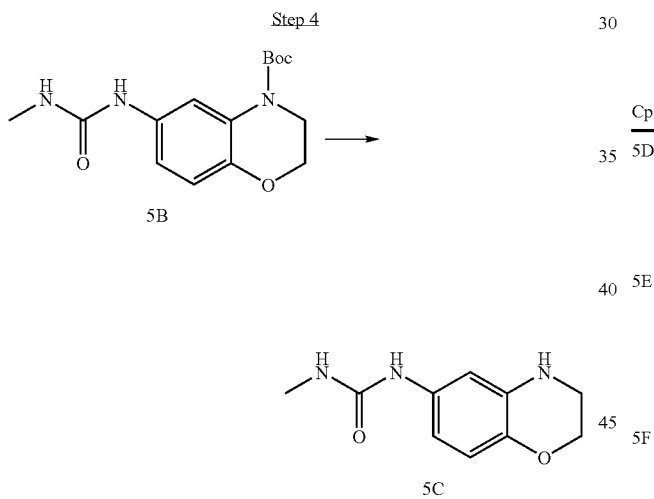

Compound 5B (890 mg, 2.9 mmol) was stirred at RT in 30% TFA/DCM (14 mL) containing three drops of Et$_3$SiH for 1 h, and then quenched with 2N NaOH solution. The mixture was extracted with EtOAc (3×50 mL). The organic layer was dried (MgSO$_4$), filtered and concentrated under vacuum. The residue (5C, 600 mg) was used in the next reaction without further purification.

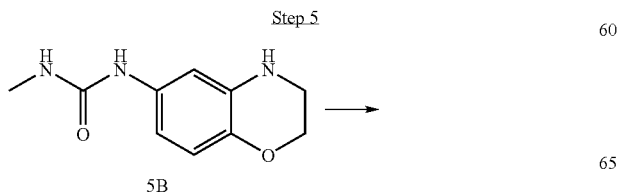

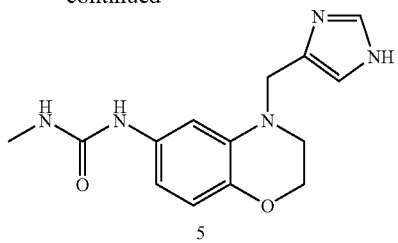

In a manner similar to that described in Example 3 (Step 3), compound 5C was treated with imidazole-4-carboxaldehyde (1B) to provide title compound 5 (56% for two steps). MS m/z 288 (MH+).

Compounds 5D-5F in Table 1 below can be prepared from compound 5A using various capping reagents as shown, followed by Boc-deprotection and reductive alkylation as described above.

TABLE 1

| Cpd | Reagent | R | MS (MH+) |
|---|---|---|---|
| 5D | Methanesulfonic anhydride/pyridine | methanesulfonyl | 309 |
| 5E | dimethylsulfamoyl chloride and pyridine | dimethylsulfamoyl | 338 |
| 5F | dimethylcarbamoyl chloride and pyridine | dimethylcarbamoyl | 302 |

Preparative Example 6

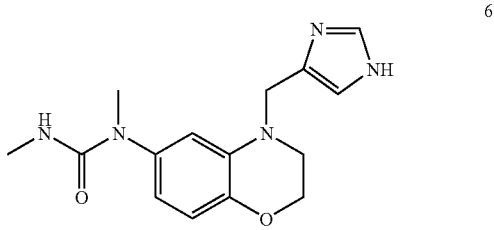

Step 1

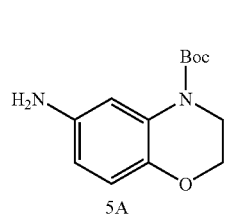

5A

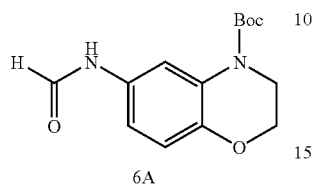

6A

Steps 3-5

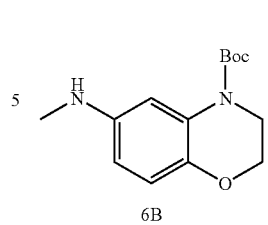

6B

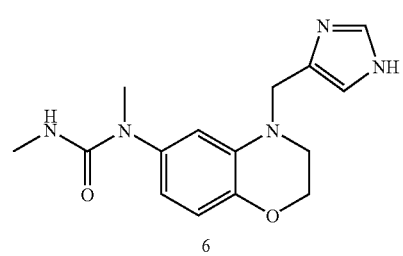

6

To a flask with Ac$_2$O (2.02 mL, 21.4 mmol) at 0° C. was added HCO$_2$H (0.82 mL, 21.4 mmol) by syringe. After stirring at 0° C. for 5 min, the mixture was heated up to 55° C. for 2 h, and then was cooled to 0° C. again. Amine 5A (2 g, 8.0 mmol) in anhydrous THF (100 mL) was added and the mixture was stirred at 0° C. for 30 min. The reaction mixture was concentrated under vacuum and diluted with 2 N NaOH solution to pH 9, extracted with EtOAc (3×50 mL). The organic layer was dried (MgSO$_4$), filtered, and concentrated under vacuum to give a foam 6A (quantitative yield).

Alternatively, a mixture of compound 5A (17.5 g, 69.9 mmol) in butyl formate (700 ml) was heated at 50° C. for 3 h and then left at RT overnight. The reaction mixture was then concentrated, added to 100 ml of 0.5N NaOH, extracted with CH$_2$Cl$_2$ (4×), dried with Na$_2$SO$_4$, and concentrated. Chromatography (10%-50% EtOAc/hexane) gave 6A (9.19 g, 47%) as a light brown sticky foam.

Step 2

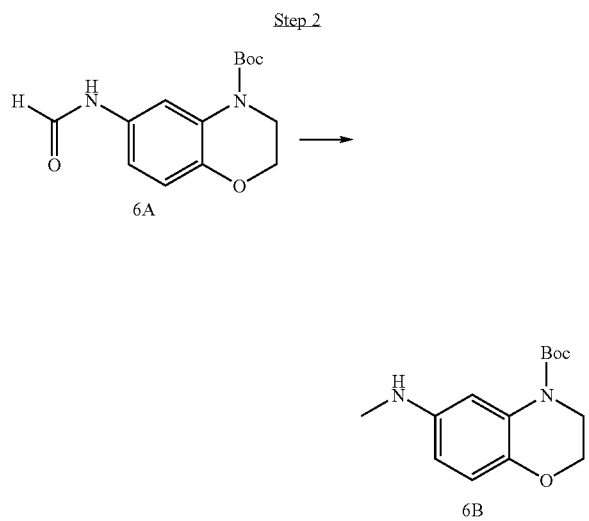

A mixture of compound 6A (2.75 g, 9.88 mmol) in THF (30 ml) was treated slowly with BH$_3$-DMS (2.0 M/THF, 7.8 ml) and then heated at reflux for 3 h. The reaction mixture was concentrated, treated with K$_2$CO$_3$ (1.5 g) and EtOH, and then stirred overnight at RT. The reaction mixture was filtered, concentrated, added to H$_2$O and extracted with CH$_2$Cl$_2$ (4×). The combined organic layers were dried with Na$_2$SO$_4$, filtered and concentrated to provide 6B as a clear oil (2.76 g).

A solution of 6B (2.76 g, crude) in CH$_2$Cl$_2$ (20 ml) was treated slowly with MeNCO (1.0 g, 12.5 mmol) and stirred at RT overnight. The reaction mixture was concentrated and chromatographed (50% to 80% EtOAc/hex, 3.10 g, 98% yield from 6A). This product (3.10 g, 9.65 mmol) was taken up in of CH$_2$Cl$_2$ (80 ml) and deprotected with of TFA (11.5 ml) as described in Example 5, Step 4 (95% yield). A mixture of the resulting amine and aldehyde 1B (1 eq) in a minimal amount of CH$_2$Cl$_2$ was treated with Ti(OiPr)$_4$ (1.3 eq). After stirring for 2 h at RT, NaBH$_4$ (1.2 eq) and EtOH were added. The reaction mixture was then stirred overnight, concentrated, treated with H$_2$O and extracted with CH$_2$Cl$_2$ (4×). The combined organic layers were dried with Na$_2$SO$_4$, filtered, concentrated and chromatographed (silica gel, 5% MeOH/CH$_2$Cl$_2$ w/NH$_3$) to provide the title compound 6 (74% yield). MS m/z 302 (MH+).

Compounds in Table 2 below can be prepared from compound 6B using the various capping reagents as shown, followed by Boc-deprotection and reductive alkylation as shown in Example 5.

TABLE 2

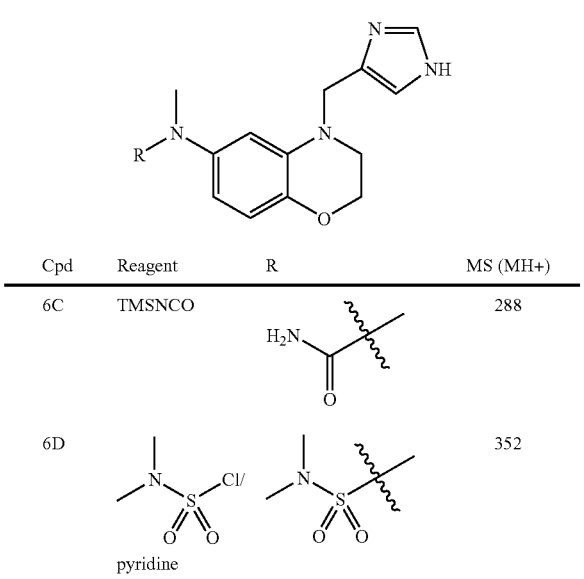

| Cpd | Reagent | R | MS (MH+) |
|---|---|---|---|
| 6C | TMSNCO | ![H2N-C(=O)-] | 288 |
| 6D | ![Me2N-S(=O)2-Cl / pyridine] | ![Me2N-S(=O)2-] | 352 |

TABLE 2-continued

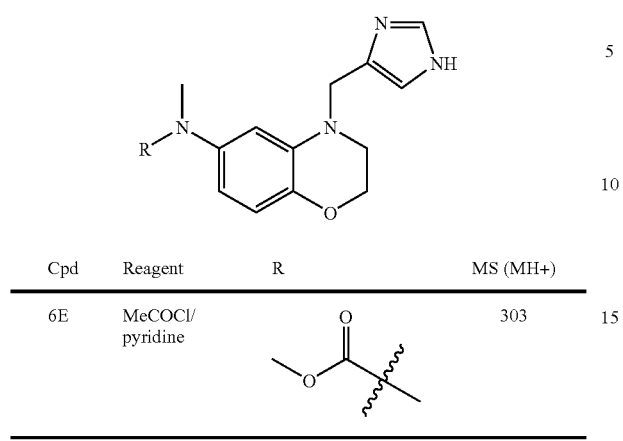

| Cpd | Reagent | R | MS (MH+) |
|---|---|---|---|
| 6E | MeCOCl/pyridine | ![](methyl 2-methylpropanoate ester group) | 303 |

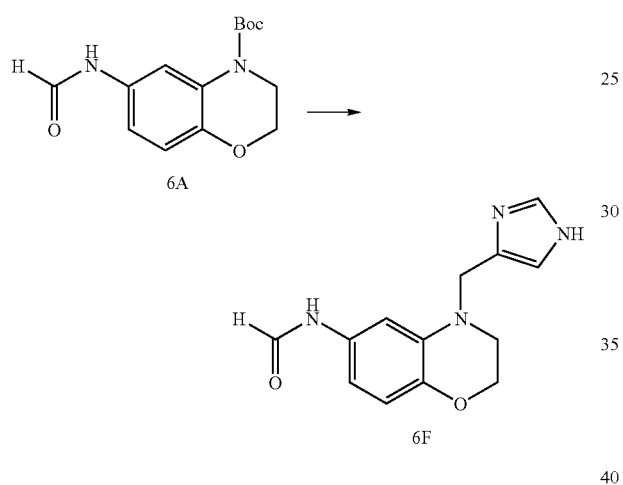

Compound 6F was prepared as follows: 6A was treated with TFA, followed by reductive alkylation with imidazole-4-carboxaldehyde (1B) as described previously in Example 5 (Step 4) and Example 3 (Step 3). MS m/z 259 (MH+).

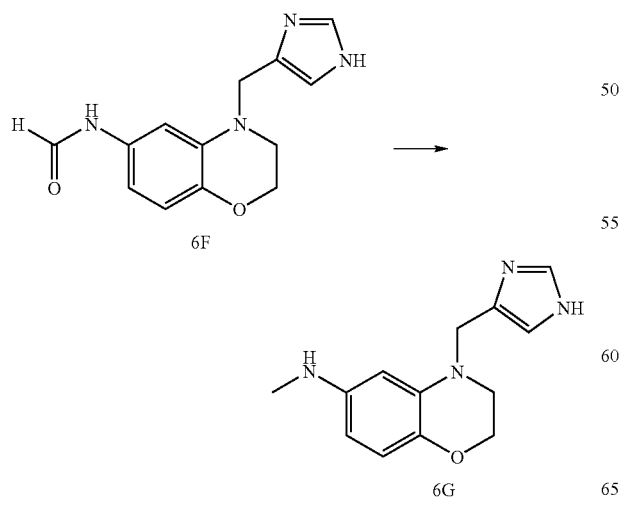

In a manner similar to Example 3, Step 2, compound 6F was reduced with $BH_3$—$SMe_2$ to provide 6G. MS m/z 245 (MH+).

Preparative Example 7

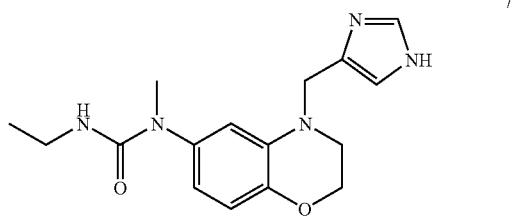

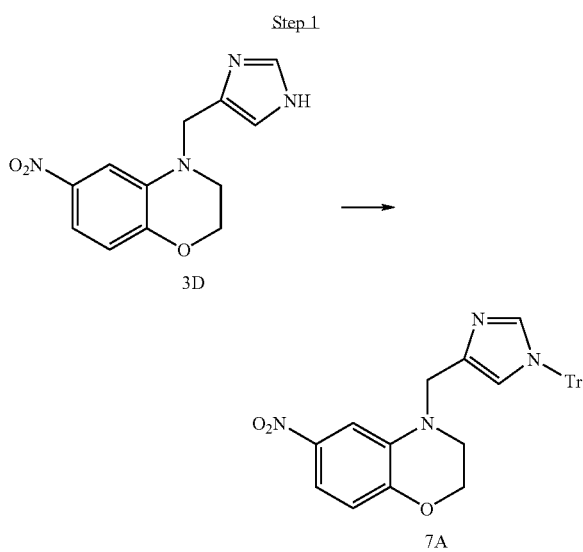

To a suspension of compound 3D (4.8 g, 18.46 mmol) in anhydrous DCM (200 mL) was sequentially added TrCl (5.15 g, 18.46 mmol) and TEA (7.7 mL, 55.37 mmol). The mixture was stirred at RT overnight, and quenched with saturated $NH_4Cl$ solution. The solution was separated and the aqueous was extracted with DCM (3×100 mL). The combined organic layers were washed with water, dried ($MgSO_4$), filtered, and concentrated under vacuum to give red yellowish solid 7A (9.13 g, yield: 98%).

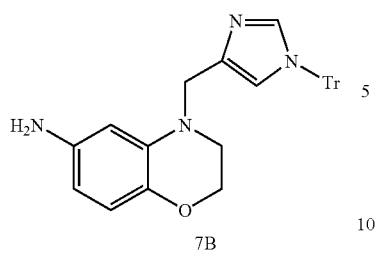

7B

To compound 7A (4.55 g, 9.06 mmol) in MeOH/EtOAc (400 mL, 1:1) in a hydrogenation bottle was added 10% Pd—C (1 g). The reaction vessel was shaken in the Parr shaker under 50 psi hydrogen for 4 h. Then the catalyst was filtered off through a celite bed and washed with MeOH and EtOAc. The filtrate was concentrated under vacuum to give white solid 7B (3.81 g, 89%).

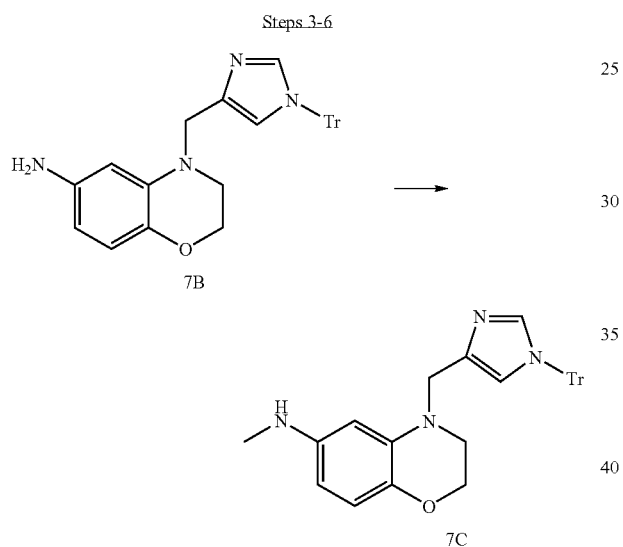

Following the approach outlined in Example 6 (Steps 1-2), 7B was treated with Ac$_2$O/HCO$_2$H and then reduced with BH$_3$—SMe$_2$ to afford 7C. In a manner similar to that found in Example 5 (Steps 3-4), 7C was further elaborated by treatment with EtNCO and deprotection with TFA to provide the title compound 7. MS m/z 316 (MH+).

Preparative Example 8

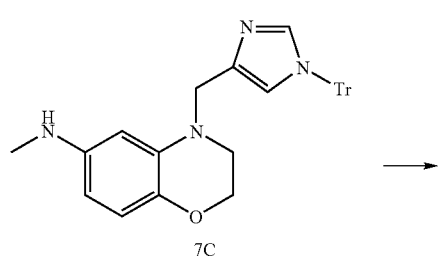

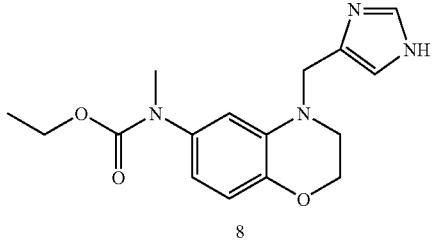

8

To compound 7C (1.5 g, 3.09 mmol) in anhydrous DCM (10 mL) was added pyridine (0.5 mL, 6.18 mmol) and ClCO$_2$Et (0.59 mL, 6.18 mmol) sequentially. The mixture was stirred at RT overnight, and then quenched with saturated NH$_4$Cl solution. The solution was concentrated and the aqueous was extracted with EtOAc (3×50 mL). The combined organic layers were washed with brine, dried (MgSO$_4$), filtered, and concentrated under vacuum.

The residue was then deprotected with TFA, in a manner described in Example 5, Step 4, to afford compound 8 (145 mg, 15% for two steps). MS m/z 317 (MH+).

Preparative Example 9

The synthesis in Example 9 used starting materials 9A, 9B or 9C. Compound 9B can be synthesized from 9A by using reduction method A or B:

Method A: To compound 9A in MeOH was added 10% Pd/C and the mixture was stirred at RT under hydrogen balloon overnight. Then the catalyst was filtered off through a celite bed and washed with MeOH. The filtrate was concentrated to give compound 9B for next reaction without further purification.

Method B: To compound 9A in EtOH was added SnCl$_2$·2H$_2$O (4 eq.), and the mixture was heated to reflux for 2 h. The mixture was concentrated and poured into ice, neutralized to pH 7 with sat. NaHCO$_3$. Then the solid was filter off and washed extensively with EtOAc. The filtrate was separated and the aqueous was extracted with (3×). The organic layer was dried (MgSO$_4$), filtered and concentrated to give compound 9B.

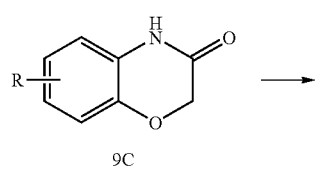

9C

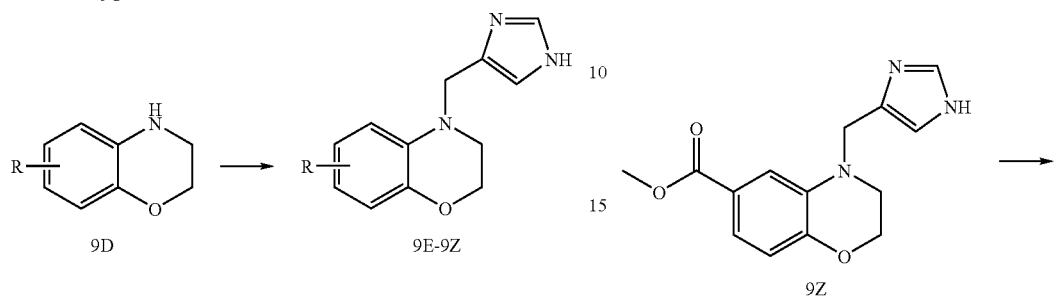

9D                    9E-9Z

Compounds 9E-9Z (shown in Table 3) were synthesized starting from 9A, 9B or 9C by following the procedures described in Example 3. The selective single-nitro reduction of starting material 9A13 (2,6-dinitrophenol) using Method A provided 2-amino-6-nitrophenol.

TABLE 3

| Starting Material | R | Reduction method from 9A | Cpd | Spectral data MS (MH+) unless noted |
|---|---|---|---|---|
| 9A1 | 4-F | A | 9E | 234 |
| 9A2 | 5-F | A | 9F | 234 |
| 9A3 | 6-F | A | 9G | 234 |
| 9A4 | 5,6-diF | A | 9H | 252 |
| 9B1 | 4-Cl | N.A. | 9I | $^1$H NMR (CDCl$_3$): 7.60 (s, 1H), 6.90 (s, 1H), 6.75 (d, 1H), 6.66 (d, 1H), 6.55 (dd, 1H), 4.40 (s, 2H), 4.20 (t, 2H), 3.40 (t, 2H) |
| 9B2 | 5-Cl | N.A. | 9J | 250 |
| 9A5 | 6-Cl | B | 9K | 250 |
| 9A6 | 4,6-diCl | B | 9L | 284 |
| 9C1 | 4-Me | N.A. | 9M | 230 |
| 9A7 | 3-Me | A | 9N | 230 |
| 9B3 | 4-Ph | N.A. | 9O | 292 |
| 9A8 | 4-Br | B | 9P | 294 |
| 9A9 | 4-CF$_3$ | A | 9Q | 284 |
| 9A10 | 3-OMe | A | 9R | 246 |
| 9A11 | 4-OMe | A | 9S | 246 |
| 9B4 | 5-OMe | N.A. | 9T | 246 |
| 9A12 | 6-OMe | A | 9U | 246 |
| 9B5 | 4-SO$_2$NH$_2$ | N.A. | 9V | 295 |
| 9B6 | 4-SO$_2$Et | N.A. | 9W | 308 |
| 9B7 | 5-NO$_2$ | N.A. | 9X | 261 |
| 9A13 | 6-NO$_2$ | A | 9Y | 261 |
| 9A14 | 4-CO$_2$CH$_3$ | B | 9Z | 274 |

Starting Material 9A10 in Table 3 was Prepared as Follows:

Dimethylsulfate (2.7 mL, 0.058 mmol) was added carefully to 2-nitrobenzene-1,3-diol (2.5 g, 0.232 mmol) and the mixture was stirred vigorously while 10% NaOH solution (21 mL) was added and the temperature was kept below 40° C. After about 15 min, the mixture was cooled and then filtered. The filtrate was collected and acidified with 10% HCl, and extracted with ether (3×25 mL). The organic layer was dried (MgSO$_4$), filtered, and concentrated under vacuum. Chromatography (10-30% EtOAc/hexanes) provided 9A10 (1 g, 37%).

Starting Material 9A12 in Table 3 was Prepared as Follows:

Fuming HNO$_3$ (0.34 mL, 0.008 mmol) was carefully added to a mixture of 2-methoxyphenol (0.886 mL, 0.008 mmol) in anhydrous DCM (10 mL) at −20° C. After stirring for 2 h at RT, the mixture was concentrated under vacuum. Chromatography (10-30% EtOAc/hexanes) provided 9A12 (400 mg, 29%) and 2-methoxy-3-nitrophenol (400 mg, 29%).

Preparative Example 10

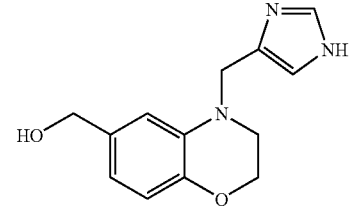

9Z

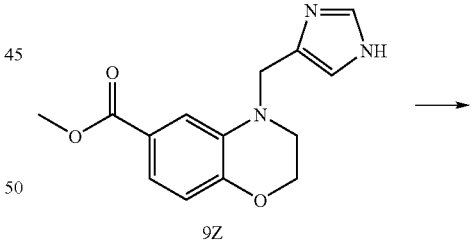

10

A mixture of compound 9Z (46 mg, 0.24 mmol) in anhydrous THF (10 mL) at 0° C. was carefully treated with LAH powder (18 mg, 0.48 mmol) and then stirred for 2 h at RT. The reaction was quenched with 1N NaOH solution (2 mL), filtered and concentrated under vacuum. Chromatography (DCM with 3 to 5% of 7N NH$_3$-MeOH) provided 10 (47 mg, 80%). MS m/z 246(MH+).

Preparative Example 11

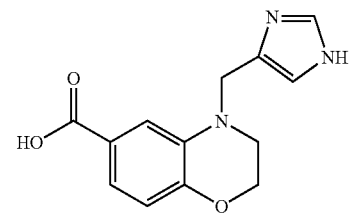

9Z

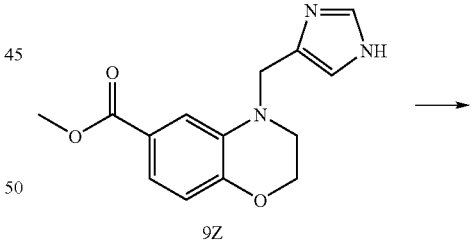

11

A mixture of 9Z (67 mg, 0.24 mmol) in MeOH (5 mL) was treated with NaOH (15 mg, 0.38 mmol) and stirred at RT overnight. The reaction was then neutralized with 10% HCl and concentrated under vacuum. The residue was taken up in MeOH, stirred for 1 h, filtered, and concentrated. Chromatography (Prep-HPLC) provided compound 11 (21 mg, 32%). MS m/z 260(MH+).

Preparative Example 12

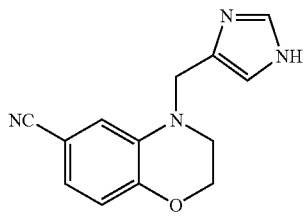

12

Step 1

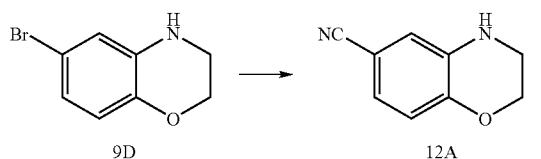

A mixture of 6-bromo-3,4-dihydro-2H-benzo[1,4]oxazine (9D, 1.5 g, 7.05 mmol) and CuCN (1.58 g, 17.61 mmol) in anhydrous DMF (15 mL) was stirred at 130° C. for 3 h and then at 150° C. overnight. Then the mixture was cooled to RT, quenched with water and concentrated under vacuum. The residue was taken up in 2N NaOH and EtOAc (100 mL) and then agitated in a sonicator for 1 h. The precipitate was filtered off and washed with EtOAc. The filtrate and washings were combined and extracted with EtOAc (2×80 mL). The organic layer was dried (MgSO₄), filtered and concentrated under vacuum to give compound 12A (1.062 g, 94%).

Step 2

In a manner similar to that found in Example 3, Step 3, 12A was converted to the title compound 12. MS m/z 241 (MH+).

Example 13

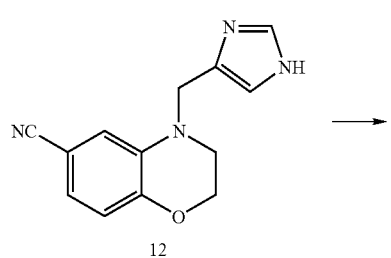

12

-continued

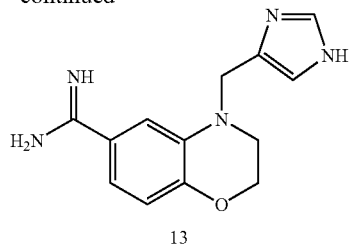

13

A solution of 12 (0.179 g, 0.75 mmol) in anhydrous EtOH (10 mL) was cooled to 0° C. and treated with bubbling HCl gas for 15 min. The mixture was stirred at 0° C. for 30 min, warmed to RT overnight, and concentrated. The residue was dissolved in 2.0 M NH₃-MeOH (5 mL), stirred at RT for 4 h, and then concentrated under vacuum. Chromatography (Ranin-Prep HPLC, Waters SunFire™ Prep C18 5 μM, 19-100 mm column, 5-90% CH₃CN/H₂O gradient) gave the compound 13 (36 mg: 19%). MS m/z 258 (MH+).

Preparative Example 14

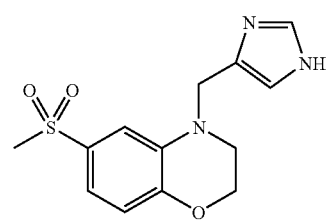

14

Step 1

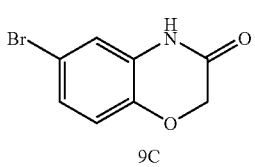

9C

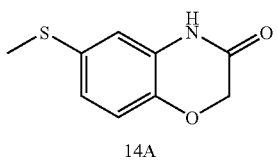

14A

To a suspension of KH (30% in mineral oil, washed with hexanes, 1.2 g, 8.98 mmol) in anhydrous THF (20 mL) at 0° C. under argon was added a solution of 6-bromo-4H-benzo[1,4]oxazin-3-one (9C, 1.02 g, 4.49 mmol) in THF (20 mL). After 15 min, the solution was cooled to −78° C., and t-BuLi (1.7 M in pentane, 5.18 mL, 8.8 mmol) was added dropwise. The mixture was stirred for 15 min at −78° C., and then treated with dimethyl disulfide dropwise. The solution was warmed gradually to RT and stirred overnight. The reaction was then quenched by sat. NH₄Cl (15 mL) carefully, and filtered. The filtrate was diluted with water and extracted with EtOAc (3×50 mL). The combined organic layers were dried (MgSO₄), filtered, and concentrated. Chromatography (5-25% EtOAc/hexanes) provided 14A (0.483 g, 55%).

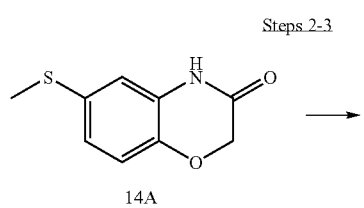

14A

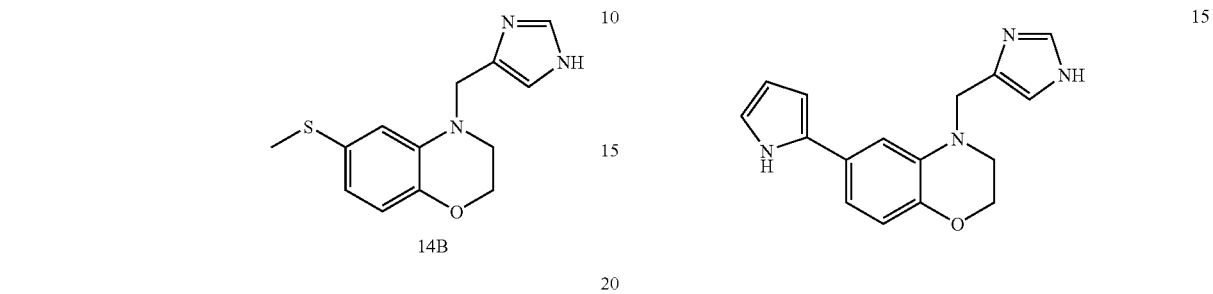

In a manner similar to that found in Example 3, Steps 2-3, 14A was reduced with BH$_3$—SMe$_2$ and treated with imidazole-4-carboxaldehyde to provide 14B. MS m/z 262(MH+).

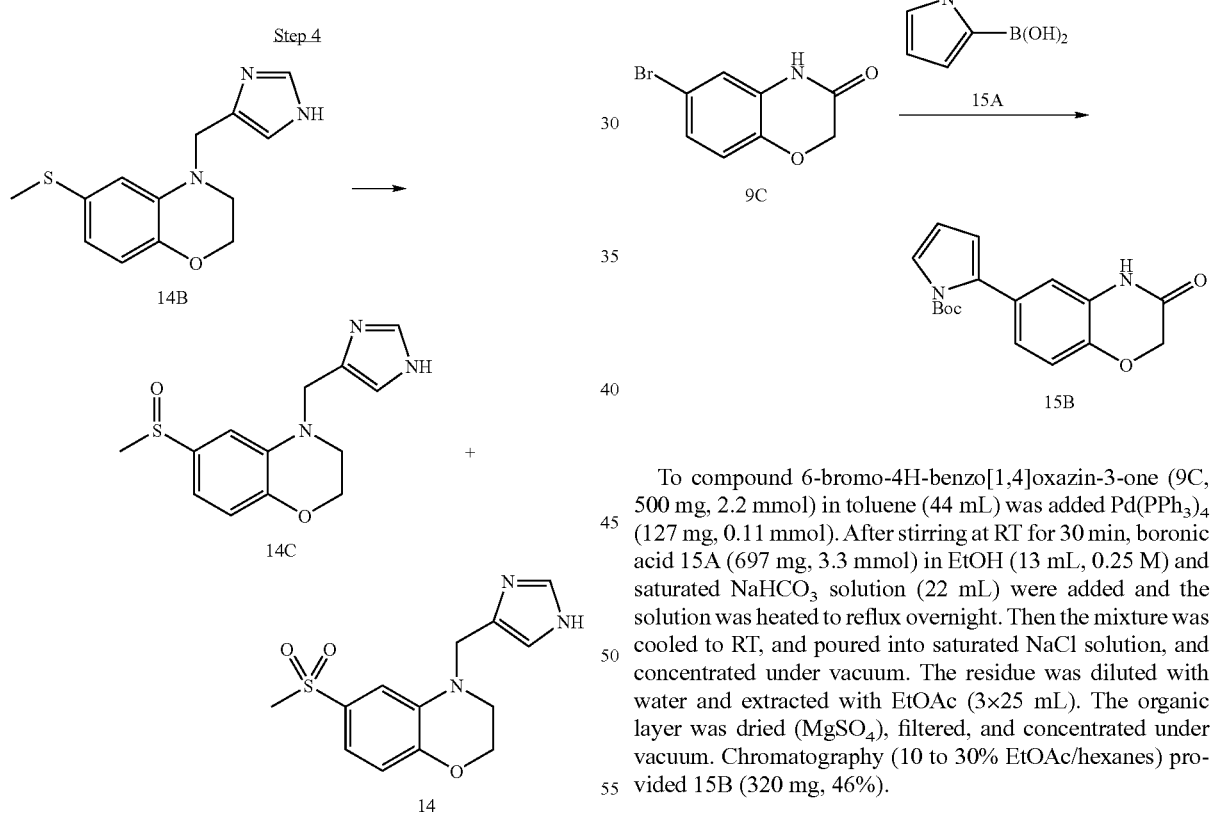

To compound 14B (0.447 g, 1.71 mmol) in anhydrous DCM (10 mL) was added MCPBA (77%, 0.85 g, 3.77 mmol), and the mixture was stirred at RT overnight. The reaction was quenched with sat. Na$_2$CO$_3$ solution and the solvent was removed under vacuum. The concentrated solution was extracted with EtOAc (3×10 mL). The organic layer was dried (MgSO$_4$), filtered, and concentrated under vacuum. Chromatography (DCM containing 1-7% of 7N NH$_3$-MeOH) provided the title compound 14 (67 mg, 13%, MS m/z 294 MH+) and a mixture of 14C and 14, which was purified by Ranin-preparative HPLC to provided 14C (39 mg, 8%, MS m/z 278 MH+).

Preparative Example 15

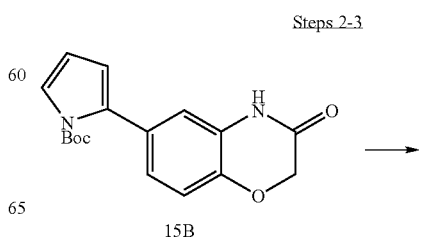

To compound 6-bromo-4H-benzo[1,4]oxazin-3-one (9C, 500 mg, 2.2 mmol) in toluene (44 mL) was added Pd(PPh$_3$)$_4$ (127 mg, 0.11 mmol). After stirring at RT for 30 min, boronic acid 15A (697 mg, 3.3 mmol) in EtOH (13 mL, 0.25 M) and saturated NaHCO$_3$ solution (22 mL) were added and the solution was heated to reflux overnight. Then the mixture was cooled to RT, and poured into saturated NaCl solution, and concentrated under vacuum. The residue was diluted with water and extracted with EtOAc (3×25 mL). The organic layer was dried (MgSO$_4$), filtered, and concentrated under vacuum. Chromatography (10 to 30% EtOAc/hexanes) provided 15B (320 mg, 46%).

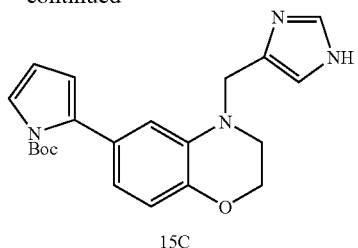

15C

In a manner similar to that found in Example 3, Steps 2-3, 15B was reduced with BH$_3$—SMe$_2$ and treated with imidazole-4-carboxaldehyde to provide 15C. MS m/z 381 (MH+).

Step 4

A mixture of 15C (143 mg, 0.37 mmol) in 4.0M HCl-dioxane (1.5 mL, 0.56 mmol) was stirred at RT overnight. The reaction was neutralized with 7N NH$_3$-MeOH and concentrated. The residue was purified by preparative TLC (DCM containing 10% of 7N NH$_3$-MeOH) to provide the title compound 15 (28 mg, 26%). MS m/z 281 (MH+).

Preparative Example 16

16

Step 1

9C

16A

To a stirred solution of Pd (OAc)$_2$ (3 mg, 0.0125 mmol) and PPh$_3$ (13 mg, 0.05 mmol) in anhydrous THF (2 mL) under argon was added 6-bromo-4H-benzo[1,4]oxazin-3-one (9C, 57 mg, 0.25 mmol). The mixture was stirred at RT for 10 min and treated sequentially with a solution of 3-pyridine boronic acid (62 mg, 0.5 mmol) in EtOH (1 mL) and aqueous NaHCO$_3$ solution (2 M, 2 mL). The mixture was heated to reflux for 2 h and then cooled to RT. The solution was poured into saturated NaCl solution, and then concentrated under vacuum. The residue was diluted with water (5 mL) and extracted with EtOAC (3×10 mL). The organic layer was dried (MgSO$_4$), filtered, and concentrated under vacuum. Chromatography (10-30% EtOAc/hexanes) provided 16A (21 mg, 37%).

Steps 2-3

Compound 16A was converted to compound 16 by reduction with BH$_3$-SMe$_2$ and reductive alkylation with imidazole-4-carboxaldehyde as described in Example 3, Steps 2-3. MS m/z 293(MH+).

Preparative Example 17

17

Step 1

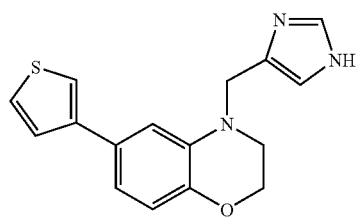

9C

17A

A Smith process vial (2-5 mL) was charged with a stir bar, 6-bromo-4H-benzo[1,4]oxazin-3-one (9C, 23 mg, 0.1 mmol), thiophen-3-ylboronic acid (17 mg, 0.13 mmol) and EtOH (2 mL). Aqueous K$_2$CO$_3$ (1 M, 0.12 mL) and polymer-supported Pd (40 mg, 3 mol % Pd, FiberCat. 1000-D32, Pd % 4.26) were then added sequentially. The reaction vessel was sealed and heated to 110° C. for 1 h under microwave irradiation. After cooling, the reaction mixture was transferred to a prepacked column of Si-carbonate (2 g, 0.79 mmol/g), which had been conditioned with MeOH/DCM (1:1). The product was eluted with MeOH/DCM (1:1, 3×3 mL, gravity filtration) and concentrated to give compound 17A (18 mg, 80%).

Steps 2-3

Compound 17A was converted to 17 in a manner similar to that found in Example 3, Steps 2-3. MS m/z 298 (MH+).

Preparative Example 18

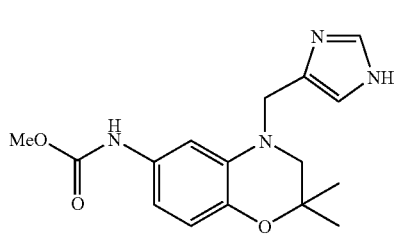

Step 1

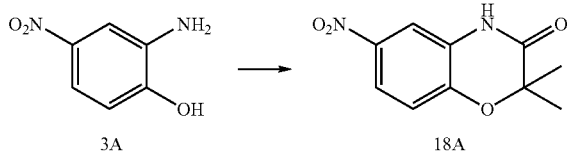

A Smith process vial (20 mL) was charged with a stir bar, compound 3A (1 g, 6.49 mmol), ethyl 2-bromo-2-methylpropanoate (1 mL, 6.81 mmol), KF (1.13 g, 19.5 mmol) and DMF (10 mL). The reaction vessel was sealed and heated to 160° C. for 1 h under microwave irradiation. After cooling, the reaction mixture was poured into ice-water and extracted with EtOAc (3×50 mL). The organic layer was dried (MgSO₄), filtered, and concentrated under vacuum. Chromatography (10-30% EtOAc/hexanes) gave 18A (0.245 g, 17%).

Step 2-3

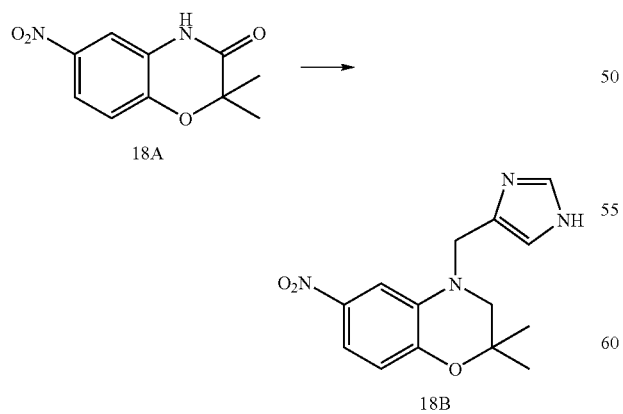

In a manner similar to that found in Example 3, Steps 2-3, 18A was reduced with BH₃-SMe₂ and reacted with imidazole-4-carboxaldehyde to provide 18B. MS m/z 289 (MH+).

Step 4-5

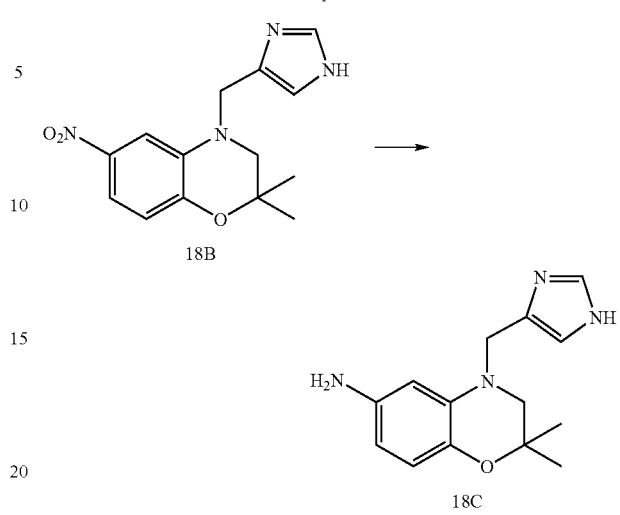

Following the procedure found in Example 3, Step 4, 18B was hydrogenated to give compound 18C. In a manner similar to that found in Example 3, Step 5, 18C was further reacted with ClCO₂Me to provide the title compound 18. MS m/z 317 (MH+).

Preparative Example 19

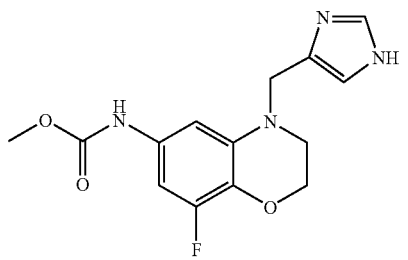

Step 1

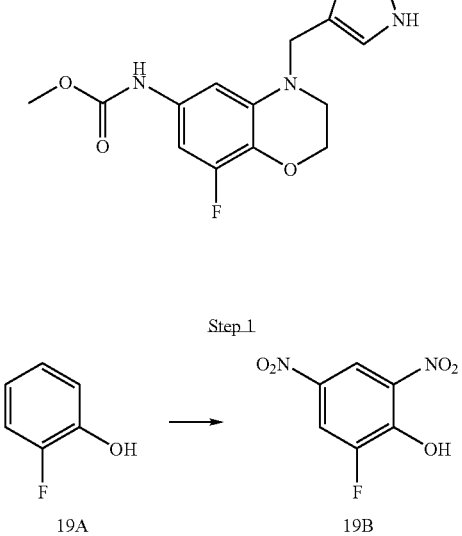

To 2-fluorophenol (19A, 8 mL, 86.4 mmol) in anhydrous DCM (70 mL) at 0° C. was added fuming HNO₃ (0.34 mL, 0.008 mmol) dropwise through an addition funnel. The mixture was warmed to RT and stirred for 2 h, then cooled to 0° C. again and quenched with 2N NaOH solution to pH 5. The mixture was concentrated under vacuum, diluted with water, extracted with EtOAc (3×100 mL). The combined organic layer was dried (MgSO₄), filtered, and concentrated under vacuum to give compound 19B (15.07 g, yield: 86.4%).

Step 2

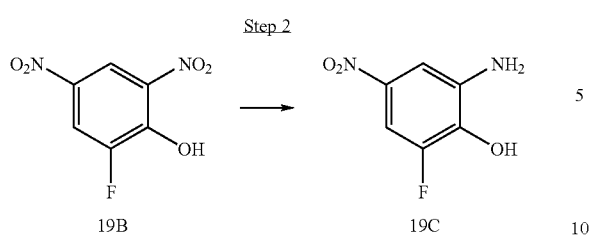

A solution of 19B (15.07 g, 74.6 mmol) in EtOH (300 mL) was treated with SnCl$_2$-2H$_2$O (50.5 g, 224 mmol) and heated to reflux for 2 h. The mixture was concentrated, poured into ice, and neutralized to pH 7 with 2N NaOH solution. The solid was filtered off and washed with EtOAc (5×500 mL). The filtrate was separated and the aqueous was extracted with EtOAc (3×100 mL). The organic layer was dried (MgSO$_4$), filtered and concentrated under afford 19C (12.59 g, 98%).

Steps 3-5

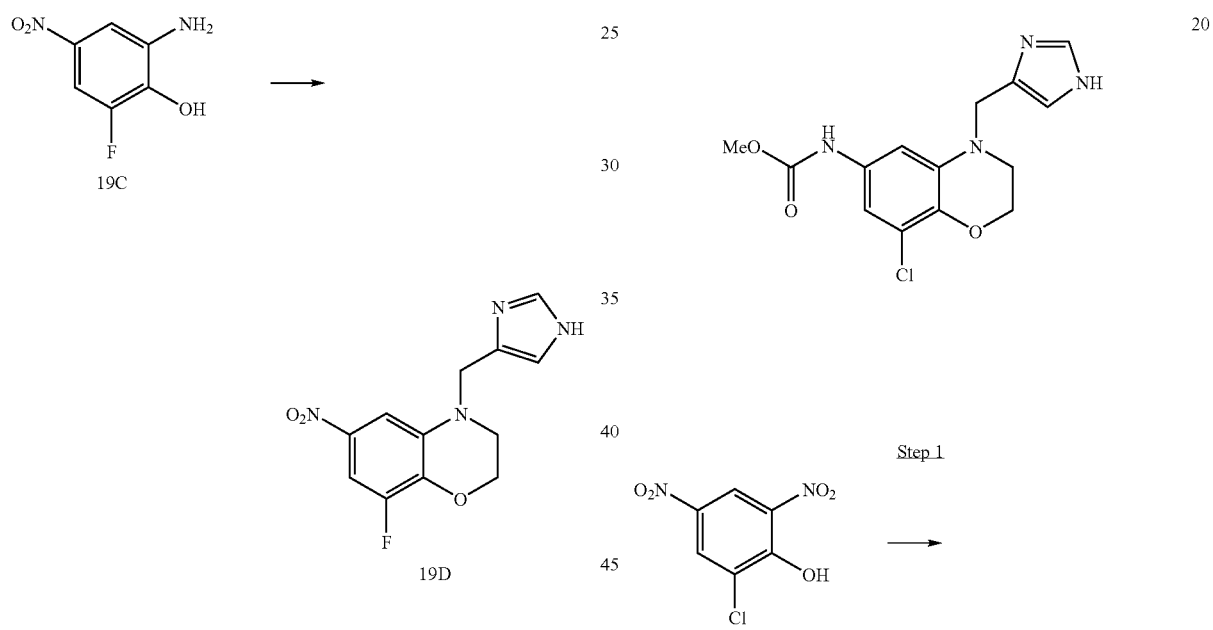

In a manner similar to that found in Example 3, Steps 1-3, 19C was reacted with chloroacetyl chloride, reduced with BH$_3$—SMe$_2$, and treated with imidazole-4-carboxaldehyde to provide compound 19D. MS m/z 279 (MH+).

Steps 6-7

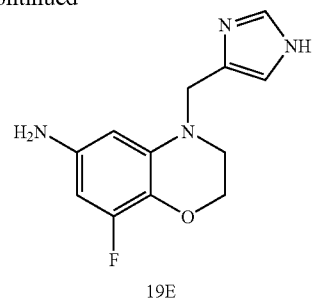

In a manner similar to that found in Example 3, Step 4, 19D was hydrogenated to afford compound 19E. MS m/z 249 (MH+). Compound 19E was further reacted with ClCO$_2$Me as described in Example 3, Step 5, to provide the title compound 19. MS m/z 307 (MH+).

Preparative Example 20

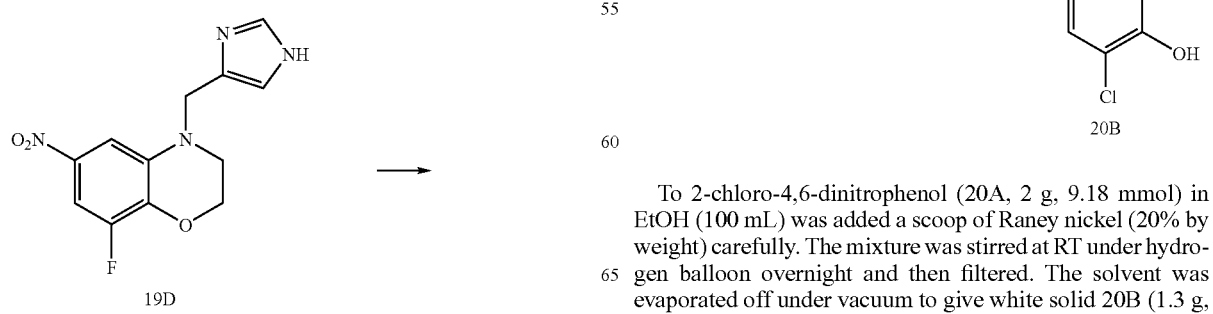

To 2-chloro-4,6-dinitrophenol (20A, 2 g, 9.18 mmol) in EtOH (100 mL) was added a scoop of Raney nickel (20% by weight) carefully. The mixture was stirred at RT under hydrogen balloon overnight and then filtered. The solvent was evaporated off under vacuum to give white solid 20B (1.3 g, 89%) and used directly in the next reaction.

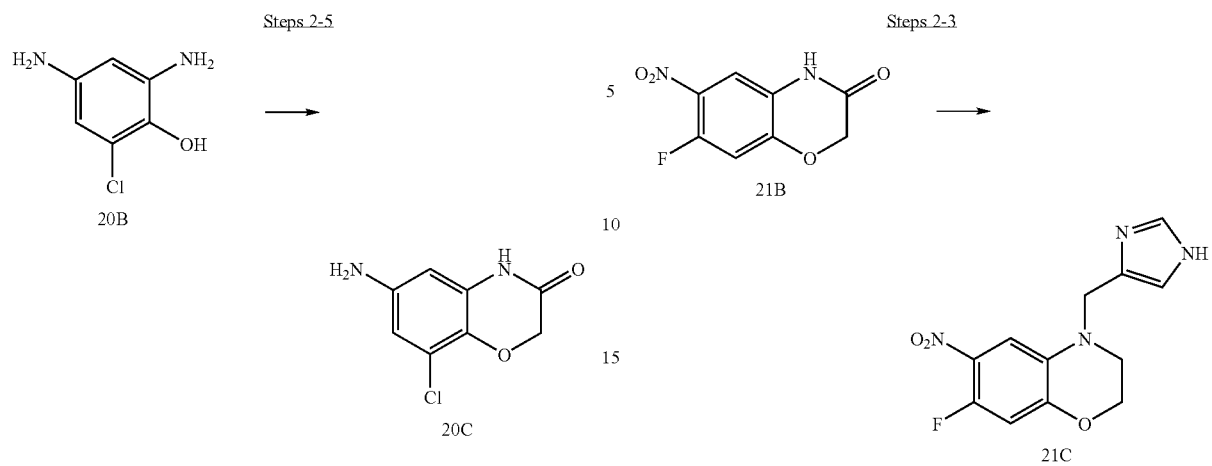

Following the procedure described in example 3, Step 1, 20B was reacted with chloroacetyl chloride to provide 20C (5%). Compound 20C was treated with ClCO$_2$Me, reduced with BH$_3$—SMe$_2$, and reductively alkylated in a manner similar to that found in Example 8 and Example 3 (Steps 2-3) to afford the title compound 20. MS m/z 323 (MH+).

Preparative Example 21

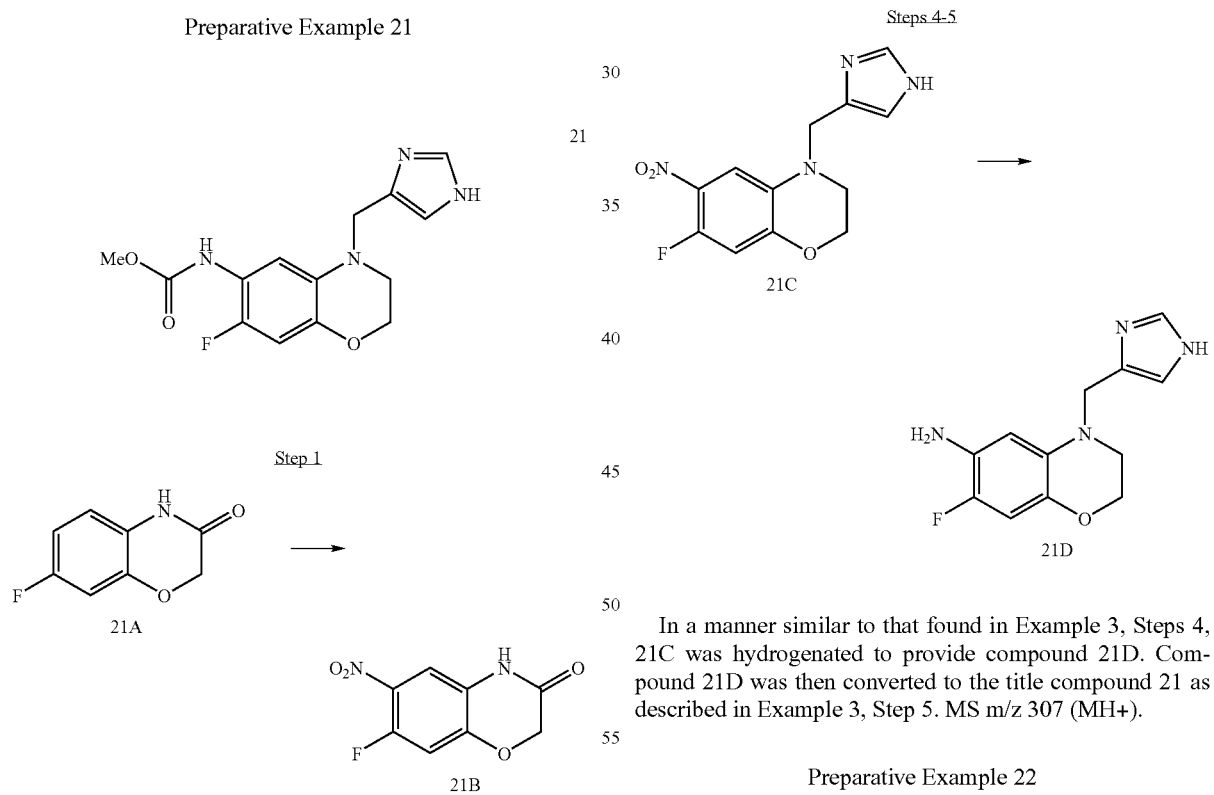

To compound 21A (5 g, 30 mmol) in concentrated H$_2$SO$_4$ (17 mL) was added a 1:1 mixture of fuming HNO$_3$ and conc. H$_2$SO$_4$ (7 mL) over 15 min. The mixture was stirred for additional 30 min at RT and was slowly poured into ice water (500 mL). The mixture was filtered to collect solid and washed with water (4x). The solid was placed under high vacuum in an 80° C. oil bath for 5 h to provide 21 B (3.82 g, 60%).

In a manner similar to that found in Example 3, Steps 2-3, 21 B was reduced with BH$_3$—SMe$_2$ and then treated with imidazole-4-carboxaldehye to afford compound 21C. MS m/z 279 (MH+).

In a manner similar to that found in Example 3, Steps 4, 21C was hydrogenated to provide compound 21D. Compound 21D was then converted to the title compound 21 as described in Example 3, Step 5. MS m/z 307 (MH+).

Preparative Example 22

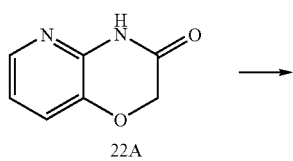

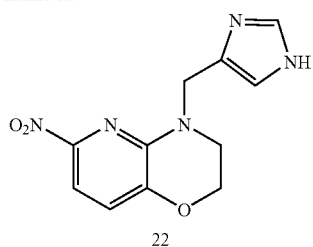

22

Following the procedures described in Example 21 (Step 1) and Example 3 (Steps 2-3), 22A was nitrated with $HNO_3$, reduced with $BH_3$—$SMe_2$, and reacted with imidazle-4-carboxaldehyde to provide compound 22. MS m/z 262 (MH+).

Preparative Example 23

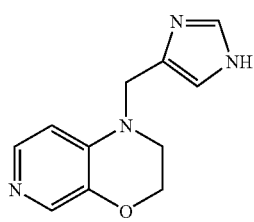

23

Step 1

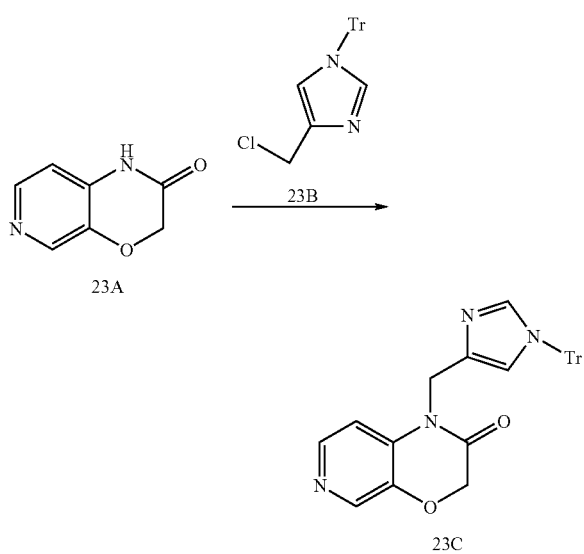

A solution of compound 23A (330 mg, 2.2 mmol, U.S. Pat. No. 5,652,363) in DMF (4 mL) was treated with NaH (60% in mineral oil, 88 mg, 2.2 mmol) at RT. The mixture was stirred for 20 min, followed by addition of a solution of compound 23B (0.79 g, 2.2 mmol, J. Med. Chem., 2002, 45, 533) in DMF (4 mL). The mixture was stirred at 45° C. for 3 days, and then quenched with water and concentrated under vacuum. The residue was dissolved in EtOAc (50 mL), washed with water (2×10 mL). The organic layer was dried ($Na_2SO_4$), filtered, and concentrated under vacuum. Chromatography (DCM with 2-3% 7 N $NH_3$-MeOH) provided 23C (519 mg, 50%). MS m/z 473 (MH+).

Steps 2-3

In a manner similar to that found in Example 2 (Step 2) and Example 15 (Step 4), 23C was reduced with $BH_2$—$SMe_2$ (18 h at reflux) and then deprotected with HCl-dioxane (1 h at 60° C.) to provide the title compound 23. MS m/z 217 (MH+).

Preparative Example 24

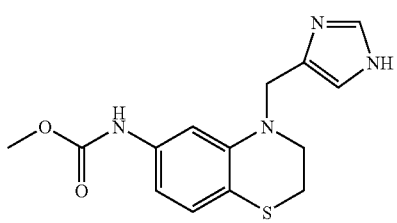

24

Step 1

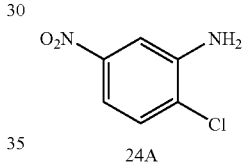

24A

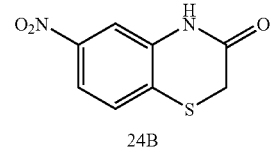

24B

A stirred solution of 2-chloro-5-nitroaniline 24A (34.4 g, 0.2 mol) in absolute EtOH (200 mL) at 70° C. was treated gradually with a solution of sodium sulfide nonahydrate (48 g, 0.2 mol) and sulfur (9.6 g, 0.3 mol), which had been preheated to melting. The mixture was refluxed for 30 min and cooled to RT. The mixture was filtered to collect the solid, wash with water. The solid was dried under vacuum at 100° C. for 5 h. The resulting solid was taken up in water (200 mL) and treated with NaOH (8 g, 0.2 mol) and $ClCH_2COOH$ (18.9 g, 0.2 mol). The mixture was then heated to reflux for 1.5 h. After cooling down, the mixture was acidified with 10% HCl solution and filtered to collect brown-yellow solid, and washed with water to give compound 24B (25 g, 60%).

Steps 2-3

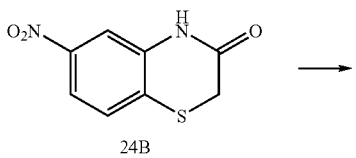

24B

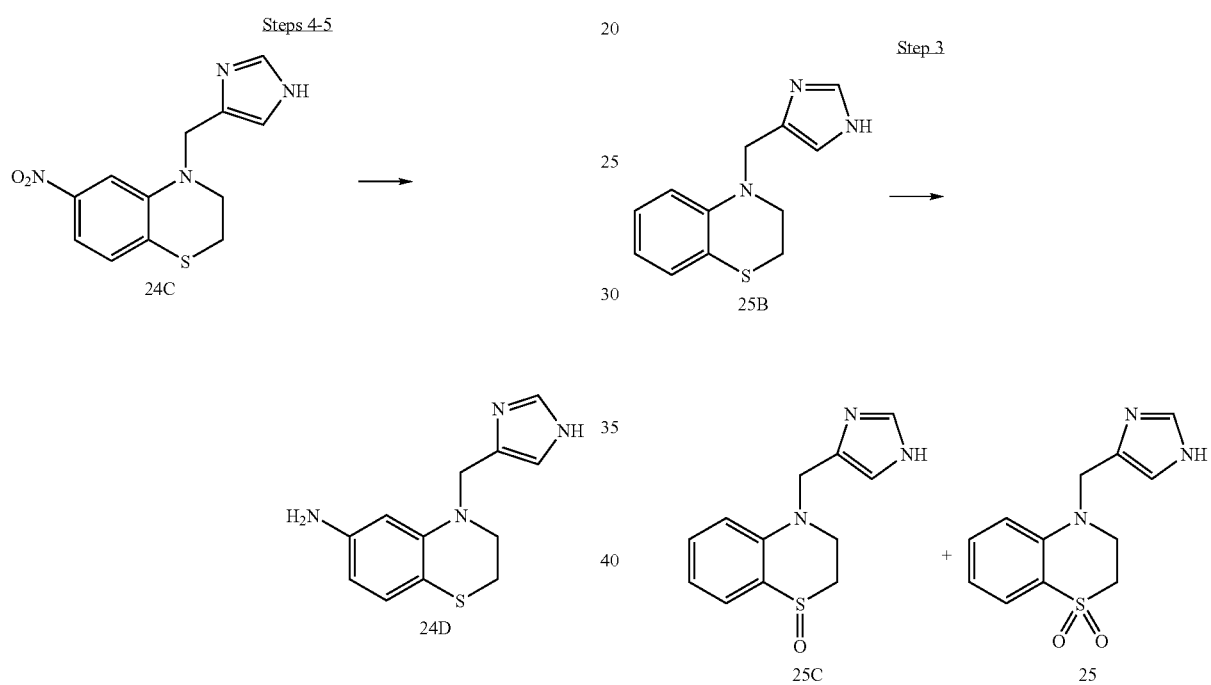

Following the procedure described in Example 3, Steps 2-3, 24B was reduced with $BH_3$—$SMe_2$ and treated with imidazole-4-carboxaldehyde to provide 24C. MS m/z 277 (MH+).

Following procedures described in Example 3 (Steps 2-3), compound 25A was subjected to reduction with $BH_3$—$SMe_2$ and then reductive amination with imidazole-4-carboxaldehyde to provide compound 25B. MS m/z 232 (MH+).

In a manner similar to that found in Example 3, Step 4, 24C was hydrogenated to provide 24D. MS m/z 247 (MH+). Compound 24D was further treated with $ClCO_2Me$ as described in Example 3, Step 5, to provide the title compound 24. MS m/z 305 (MH+).

In a manner similar to that found in Example 14, Step 4, 25B was oxidized with MCPBA to the afford compounds 25C (MS m/z 248 MH+) and 25 (MS m/z 264 MH+).

Preparative Example 25

Preparative Example 26

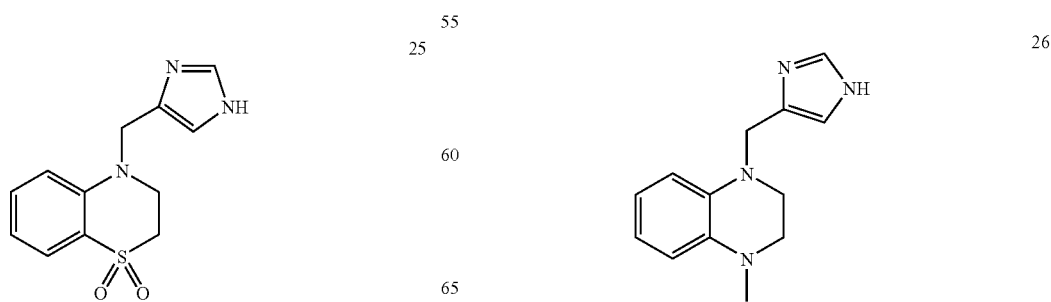

Step 1

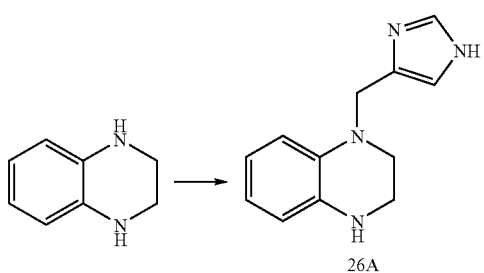

In a manner similar to that found in Example 1, 1,2,3,4-tetrahydro-quinoxaline and imidazole-4-carboxaldehye 1B underwent reductive amination to provide 26A. LMCS m/z 215 (MH+).

Step 2

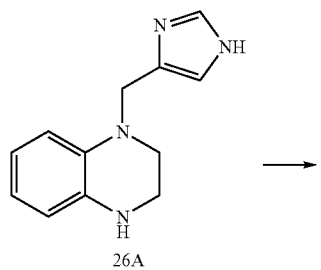

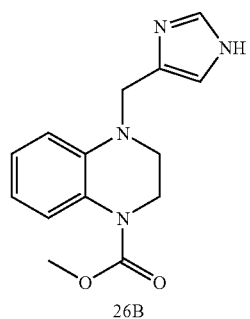

In a manner similar to that found in Example 3, Step 5, 26A was converted to 26B. LMCS m/z 273 (MH+).

Step 3

Compound 26B (120 mg) was added portionwise to a stirred slurry of LAH powder (500 mg) in Et$_2$O (15 mL) at 0° C. The mixture was refluxed for 1 h and then cooled to 0° C. The reaction was treated sequentially with H$_2$O (0.5 mL), 1 N NaOH (0.5 mL), and H$_2$O (1.5 mL). and then concentrated. Chromatography (DCM with 2 to 5% of 7N NH$_3$-MeOH) provided the title compound 26. MS m/z 229(MH+). Alternatively, compounds in this class may be synthesized by a solid phase approach as described in the following Example 27.

Preparative Example 27

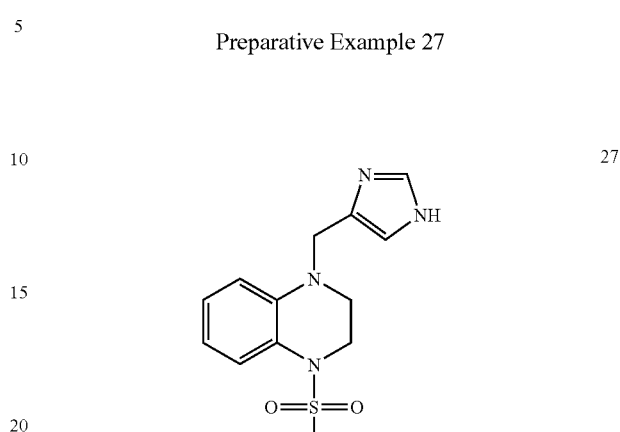

Steps 1-2

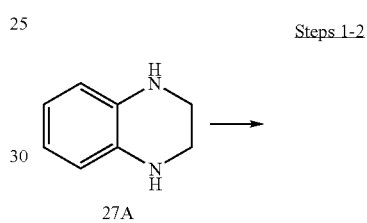

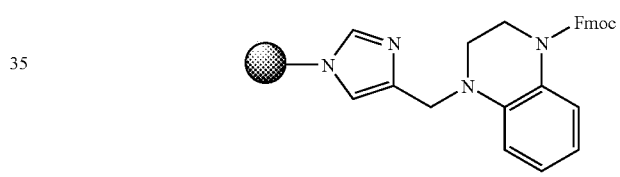

A mixture of 1,2,3,4-tetrahydroquinoxaline (27A, 2 g, 14.9 mmol) in dioxane (15 mL) and water (24 mL) at 0° C. was sequentially treated with Na$_2$CO$_3$ (1.58 g, 14.9 mmol) and FmocCl (3.84 g, 14.9 mmol) in dioxane (20 mL, added dropwise). The mixture was warmed to RT gradually and stirred overnight. The reaction mixture was diluted with water (50 mL) and extracted with DCM (2×70 mL). The combined organic layers were dried (Na$_2$SO$_4$), concentrated, and subjected to chromatography (30-40% EtOAc/hexanes, yields 0.75 g, 14%). Subsequent reaction with resin 1D as described in Example 1 provided 27B.

Steps 3-5

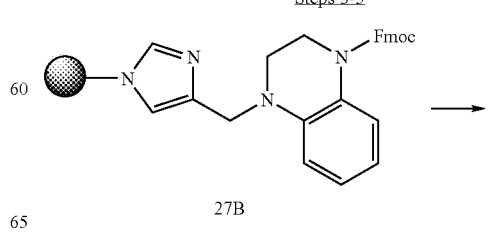

67

-continued

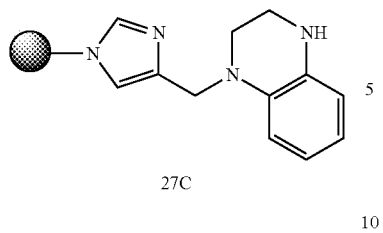

27C

Compound 27B (0.5 g, 1.4 mmol/g) was stirred in 30% piperidine/DMF overnight. The resin was washed with DMF (3×), MeOH (3×) and DCM and then dried in vacuo to provide 27C. Resin 27C (125 mg, 1.4 mmol/g) was suspended in DCM (5 mL) and treated with pyridine (0.283 mL, 3.5 mmol) and MeSO$_2$Cl (0.135 mL, 1.75 mmol). The reaction was shaken overnight, then washed with MeOH (2×), DMF (2×), DCM (2×), MeOH (2×) and DCM (3×). Subsequent cleavage from the resin with TFA, as described in Example 1, provided the title compound 27. MS m/z 293 (MH+).

Compounds in Table 4 can be prepared from Resin 27C by reaction with the various reagents shown followed by TFA cleavage.

TABLE 4

| Cpd | Reagent | R | MS (MH+) |
|---|---|---|---|
| 27D | Me$_2$NSO$_2$Cl/ pyridine | ![S(=O)(=O)N(Me)Me] | 322 |
| 27E | Ac$_2$O/ pyridine | ![C(=O)Me] | 257 |
| 27F | MeNCO | ![C(=O)NHMe] | 272 |

68

Preparative Example 28

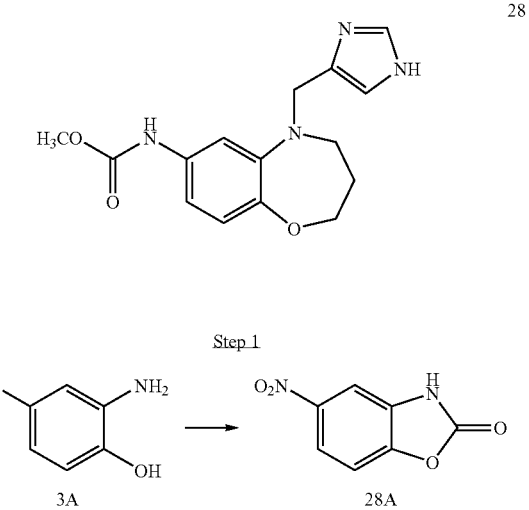

28

Step 1

O$_2$N–[benzene]–NH$_2$, OH (3A) → O$_2$N–[benzoxazolone] (28A)

To 6-nitro-2-aminophenol (3A, 3.03 g, 19.7 mmol) in anhydrous DCM (50 mL) was added dipyridylcarbonate (4.25 g, 19.7 mmol). The mixture was stirred at RT overnight, and then concentrated under vacuum. Chromatography (1-6% MeOH/DCM) afforded the solid 28A (2.77 g, 78%).

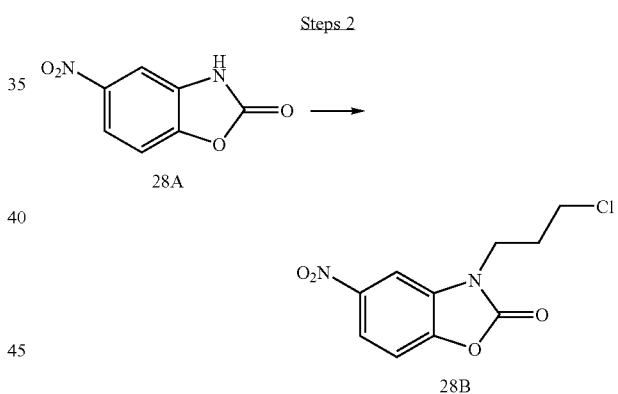

A solution of 28A (0.69 g, 3.83 mmol) in 2-ethoxyethanol (10 mL) was treated with KOH (0.22 g, 3.83 mmol) and stirred at RT for 1 h. The mixture was then heated to reflux and treated with 1-bromo-3-chloropropane (0.75 mL, 7.67 mmol). After refluxing for 4 h, the solution was filtered and concentrated to provide 28B, which was taken on to Step 3 without further purification.

Step 3

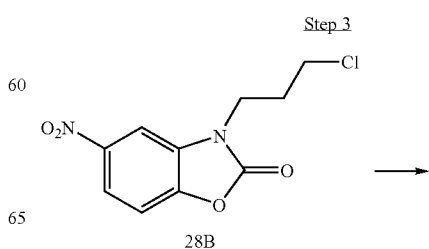

28B

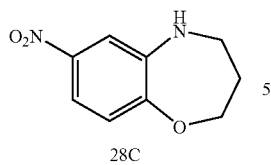

A solution of 28B in 2-ethoxyethanol and DMF (10 mL, 1:1) was transferred into a Smith process vial (20 mL) with a stir bar, and treated with KOH (0.86 g, 15.32 mmol). The reaction vessel was sealed and heated to 220° C. for 1 h under microwave irradiation. After cooling, the reaction mixture was filtered and concentrated. The residue was diluted with water and extracted with EtOAc (3×10 L). The combined organic layers were dried (MgSO$_4$), filtered, and concentrated under vacuum. Chromatography (DCM containing 1-5% 7N NH$_3$-MeOH) provided 28C (124 mg, 17% for 2 steps).

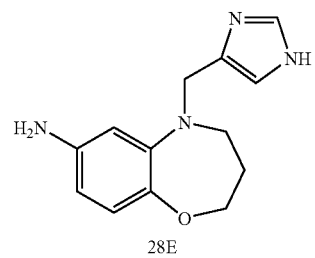

In a manner similar to that found in Example 3 (Step 4), 28D was hydrogenated to afford compound 28E. MS m/z 245 (MH+). Following the procedure found in Example 3 (Step 5), 28E was further reacted with ClCO$_2$Me to provide the title compound 28. MS m/z 303 (MH+).

Preparative Example 29

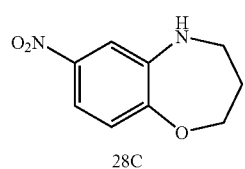

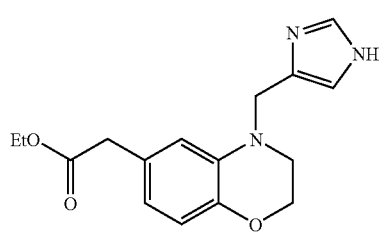

In a manner similar to that found in Example 3 (Step 3), 28C was reacted with imidazole-4-carboxyaldehyde to provide compound 28D. MS m/z 275 (MH+).

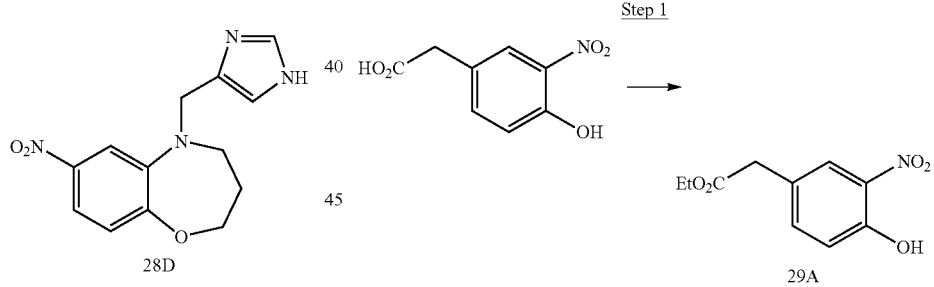

A mixture of 4-hydroxy-3-nitrophenylacetic acid (10 g, 51 mmol) and 4M HCl-dioxane (40 mL) in EtOH (150 mL) was refluxed for 2 h and concentrated. The residue was then taken up in 1 N NaOH (50 mL) and extracted with CH$_2$Cl$_2$ (8×). The combined organic layers were dried over Na$_2$SO$_4$, and concentrated to provide 29A (8.39 g, 73%) as a yellow oil.

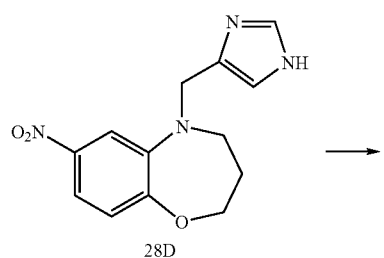

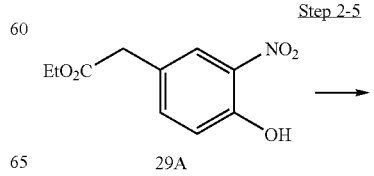

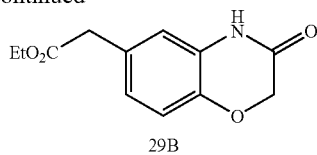

29B

In a manner similar to that described in Example 20 (Step 1) and Example 3 (Step 1), 29A was hydrogenated with Raney Ni (50 psi $H_2$) and then cyclized with chloroacetyl chloride to provide 29B. Compound 29B could be further elaborated to the title compound 29 following the procedure detailed in Example 3 (Steps 2-3). LMCS m/z 302 (MH+).

Preparative Example 30

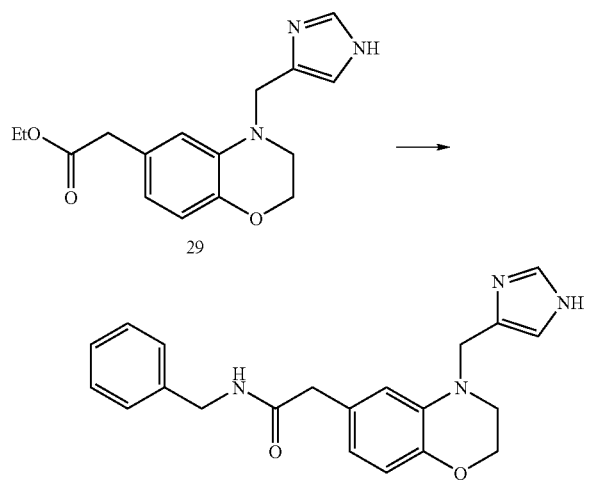

A stirred solution of benyzlamine (0.070 mL, 0.66 mmol) in $CH_2Cl_2$ (10 mL) was treated dropwise with $AlMe_3$ (2M/toluene, 0.33 mL, 0.66 mmol) at 20° C. After 20 min, a solution of 29 (0.10 g, 0.33 mmol) in $CH_2Cl_2$ (3 mL) was added slowly. The mixture was then heated at reflux overnight and cooled to 20° C. The reaction was quenched with $H_2O$ (0.5 mL), and stirred 1 h. The mixture was then dried with $Na_2SO_4$, filtered, and concentrated. Chromatography (2-5% 1 N $NH_3$-MeOH/$CH_2Cl_2$) provided 30 as a white film (0.115 g, 96%). LMCS m/z 363 (MH+).

Preparative Example 31

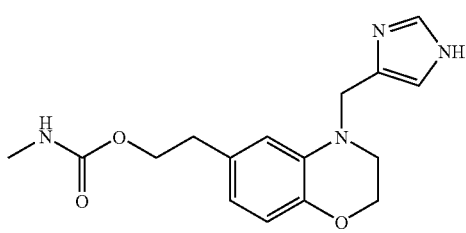

31

Steps 1-2

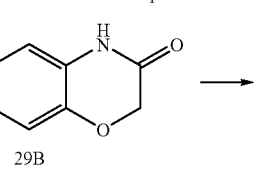

29B

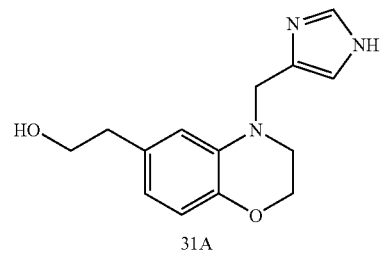

31A

In a manner similar to that found in Example 26 (Step 3) and Example 1, 29B was reduced with LAH and then treated with imidazole-4-carboxaldehyde to provide 31A. LMCS m/z 260 (MH+).

Step 3

A solution of 31A (0.20 g, 77 mmol) in 1,2-dichloroethane (10 mL) was treated with $Et_3N$ (0.20 mL, 1.5 mmol) and MeNCO (0.050 mL, 0.85 mmol) and stirred for 3 h at 20° C. The mixture was treated with $H_2O$ (10 mL), extracted with $CH_2Cl_2$ (2×), and concentrated. The residue was subjected to chromatography (2-5% MeoH/$CH_2Cl_2$) and then stirred in $Et_2NH$ (5 mL) at 20° C. overnight. The mixture was concentrated, treated with 1 N NaOH, and extracted with $CH_2Cl_2$ (3×). The combined organic extracts were dried with $Na_2SO_4$, and concentrated. Chromatography (5% MeOH/$CH_2Cl_2$) provided 31 as a white film (0.080 g, 33%). LMCS m/z 317 (MH+).

Preparative Example 32

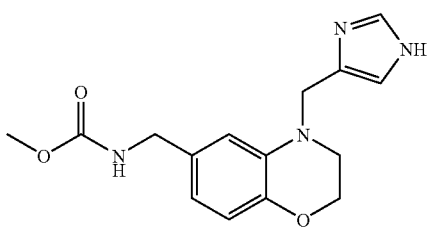

32

Steps 1-2

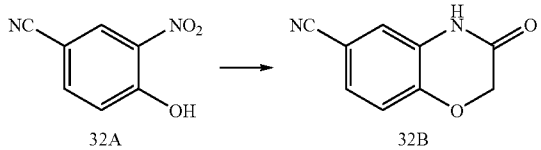

32A          32B

Following the procedures found in Example 20 (Step 1) and Example 3 (Step 1), 32A was hydrogenated with Raney Ni (50 psi $H_2$) and then cyclized with chloroacetyl chloride to provide 32B.

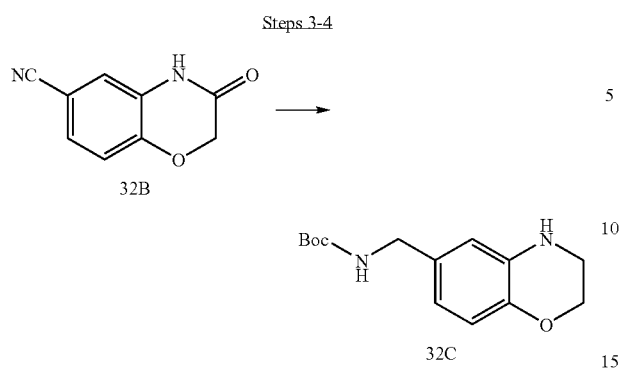

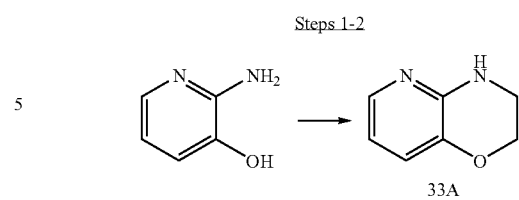

In a manner similar to that found in Example 3 (Step 1) and Example 26 (Step 3), 2-amino-3-hydroxypyridine was cyclized with chloroacetyl chloride and then reduced with LAH to afford 33A.

Following the procedure found in Example 26 (Step 3), the nitrile and amide found in compound 32B were concomitantly reduced with LAH. The resultant product (0.83 g, 5.1 mmol) in $CH_2Cl_2$ (50 mL) was treated with $BOC_2O$ (1.07 g, 5.1 mmol), stirred at 20° C. for 0.5 h and then concentrated. Chromatography (20-50% EtOAc/hexanes) provided 32C as a white sticky foam (1.19 g, 89%)

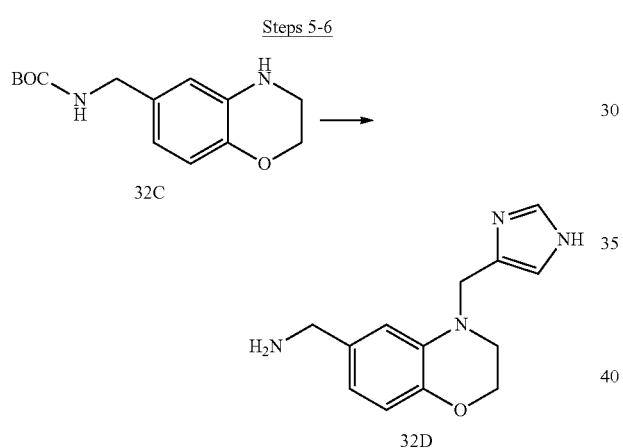

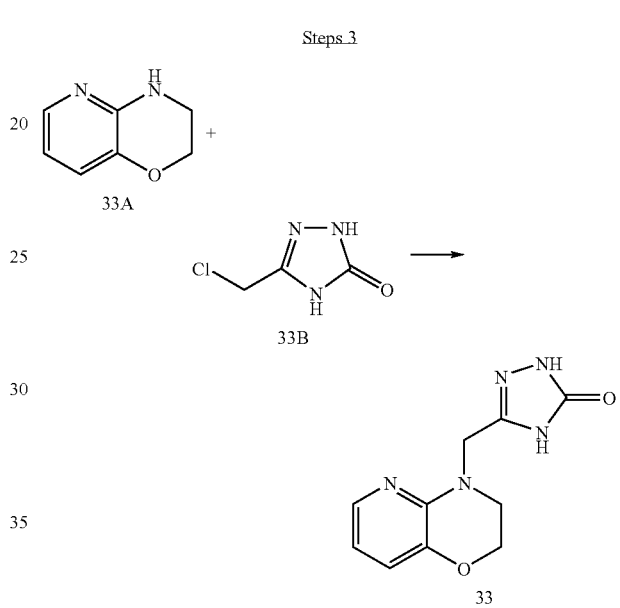

In a manner similar to that found in Example 1 and Example 15 (Step 4), 32C was treated with imidazole-4-carboxaldehyde and then deprotected to afford 32D. LMCS m/z 245 (MH+). Following the procedure described Example 3, Step 5, 32D was treated with $ClCO_2Me$ and converted to the title compound 32. LMCS m/z 303 (MH+).

A solution of 33A (0.105 g 0.77 mmol) in DMF (5 mL) was treated with $KN(SiMe_3)_2$ (0.5 M/toluene, 1.8 mL, 0.93 mmol), stirred at 0° C. for 20 min, and then treated with 33B (0.155 g 1.16 mmol, Tetrahedron Letters 2000, 41, 8661). The reaction was warmed to 20° C., stirred 2 h, and concentrated. The residue was then treated with 0.5 N NaOH (10 mL) and washed with $CH_2Cl_2$ (3×). The aqueous layer was concentrated and subjected to chromatography (20-80% EtOAc/hexanes) to provide 33 as a white solid (0.065 g, 36%). LMCS m/z 234 (MH+).

Preparative Example 33

Preparative Example 34

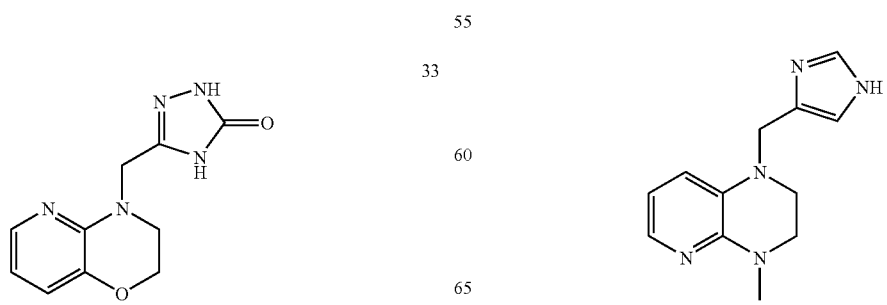

Step 1

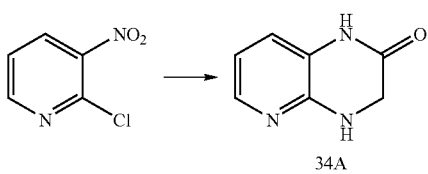

34A

A mixture of 2-chloro-3-nitropyridine (9.4 g, 59 mmol), glycine ethyl ester hydrochloride (10.8 g, 77 mmol), and K$_2$CO$_3$ (21.3 g, 154 mmol) in toluene (100 mL) was refluxed overnight. The mixture was then filtered, concentrated, and subjected to chromatography (20% EtOAc/hexanes). The resulting yellow solid was dissolved in EtOH (300 mL), treated with Raney Ni (2 g) and hydrogenated at 40 psi H$_2$ overnight. The mixture was filtered, concentrated and chromatographed (2-5% MeOH/CH$_2$Cl$_2$) to provide 34A (1.25 g, 14%) and N-(3-amino-2-pyridinyl)glycine ethyl ester (8.2 g, 71%).

Step 2

34A → 34B

In a manner similar to that found in Example 5 (Step 1), 34A was converted to 34B (BOC$_2$O, DMAP and Et$_3$N in refluxing DCM).

Step 3-4

34B → 34C

In a manner similar to that found in Example 26 (Step 3), 34B was treated with LAH to provide 34C as a white solid (0.040 g, 48%). Following the procedure found in Example 1, 34C was then treated with imidazole-4-carboxaldehyde to provide the title compound 34. LMCS m/z 230 (MH+).

Preparative Example 35

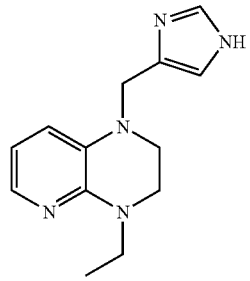

35

Step 1-3

34A → 35A

A solution of 34A (0.260 g, 1.74 mmol) in THF (15 mL) was treated with Et$_3$N (1.2 mL, 8.7 mmol) and Ac$_2$O (0.33 mL, 3.5 mmol) and stirred overnight at 20° C. The reaction was treated diluted with H$_2$O (10 mL) and extracted with 10% MeOH/CH$_2$Cl$_2$ (3×). The combined organic extracts were dried with Na$_2$SO$_4$ and concentrated. Chromatography (20-50% EtOAc/hexanes) provided 35A as a white solid (0.140 g, 42%).

In a manner similar to that found in Example 26 (Step 3) and Example 1, 35A was reduced with LAH and then treated with imidazole-4-carboxaldehyde to provide the title compound 35. LMCS m/z 244 (MH+).

Preparative Example 36

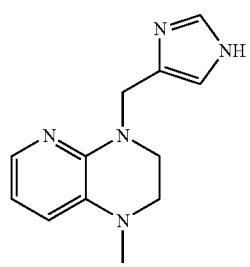

36

Step 1-3

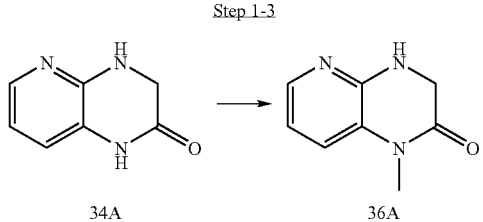

A solution of 34A (0.200 g 1.33 mmol) in DMF (15 mL) was treated with KN(SiMe$_3$)$_2$ (0.5M/toluene, 3.2 mL, 0.93 mmol), stirred at 0° C. for 30 min, and then treated with CH$_3$I (0.12 mL, 2.00 mmol). The reaction was warmed to 20° C., stirred overnight, and concentrated. The residue was then treated with 0.5 N NaOH (10 mL) and extracted with CH$_2$Cl$_2$ (3×). The combined organic layers were concentrated and subjected to chromatography (2-5% MeOH/CH$_2$Cl$_2$) to provide 36A (0.120 g, 55%).

In a manner similar to that found in Example 26 (Step 3) and Example 1, 36A was reduced with LAH and then reacted with imidazole-4-carboxaldehyde to provide 36. LMCS m/z 230 (MH+).

Preparative Example 37

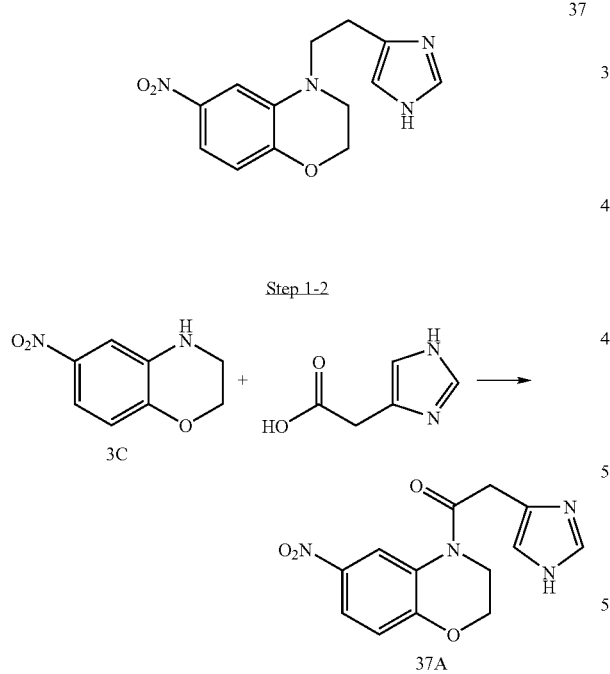

A mixture of 3C (2 g, 11.1 mmol) in anhydrous DMF (20 mL) was treated with 2-(1H-imidazol-4-yl)acetic acid (2 g, 17.5 mmol), HATU (6.2 g, 16.3 mmol) and DIEA (0.4 mL, 2.3 mmol) at 25° C. The mixture was stirred at room temperature overnight and then concentrated under vacuum. Column chromatography (DCM containing 1-6% of 7N NH$_3$/MeOH) provided 37A (1.2 g, yield: 38%). In a manner similar to Example 2, Step 2, compound 37A was reduced with BH$_3$—SMe$_2$ to provide compound 37. MS m/z 275 (MH+).

Preparative Example 38

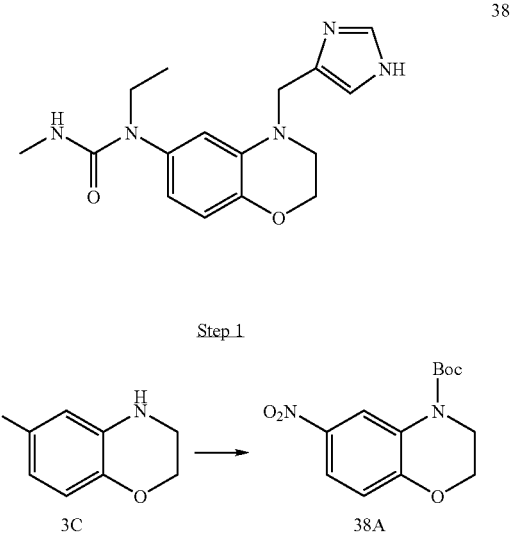

Step 1

A solution of compound 3C (14.1 g, 78 mmol) in MeCN (200 mL) was treated with (BOC)$_2$O (20.5 g, 94 mmol) and DMAP (0.5 g) and then refluxed overnight. The reaction mixture was concentrated and chromatographed (10%-50% EtOAc/hexanes) to give compound 38A (16.1 g, 74%, typically 70-90%) and recovered starting material 3C.

Steps 2-3

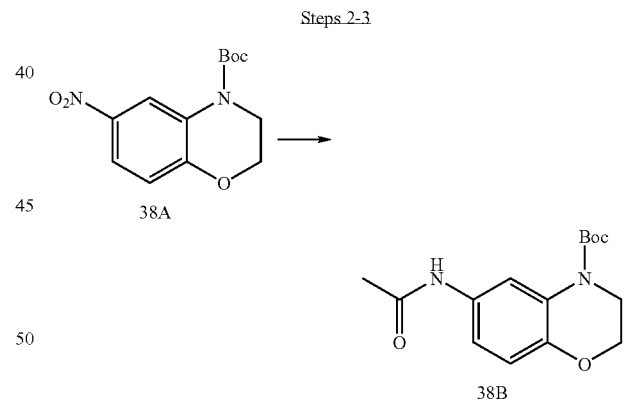

A mixture of compound 38A (16.1 g, 58 mmol) in EtOH (300 ml) was treated with Raney Ni (~5 g) and hydrogenated (40 psi H$_2$) overnight. The reaction mixture was filtered and concentrated.

The resulting white solid (~15.3 g, 61 mmol) was suspended in anhydrous THF (200 mL) and treated slowly with Ac$_2$O (~18 mL, 173 mmol). After stirring for 2 h at 20° C., the reaction mixture was concentrated in vacuo and taken up in 25% aqueous NaOH (100 mL) and CH$_2$Cl$_2$. The layers were separated. The aqueous layer was further extracted with CH$_2$Cl$_2$ (3×). The organic layers were combined, dried with Na$_2$SO$_4$, and filtered to give 38B as a gray solid (17.6 g, quantitative yield).

Steps 4-5

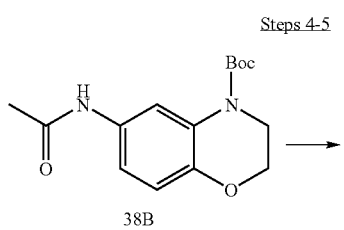

A solution of compound 38B (21 g, 72 mmol) in THF (300 ml) at 0° C. was slowly treated with BH₃-DMS (60 ml, 2M/THF) and then heated to reflux overnight. The mixture was concentrated, treated with K₂CO₃ (9.9 g) and EtOH (300 mL) and then refluxed for 45 min. The reaction mixture was filtered, concentrated, added to H₂O and extracted with CH₂Cl₂ (4×). The combined organic layers were dried with Na₂SO₄, filtered and concentrated.

The resulting clear oil (21.9 g) was dissolved in anhydrous CH₂Cl₂ (300 ml), treated slowly with MeNCO (~5 g, 86 mmol), and then stirred at RT for 30 min. The reaction mixture was concentrated and chromatographed (50%-80% EtOAc/hexanes) to give the product 38C as a white solid (21.65 g, 90% yield for two steps).

Steps 6-7

A solution of compound 38C (21.65 g, 65 mmol) in of CH₂Cl₂ (300 ml) was treated with TFA (100 mL) and refluxed for 0.5 h. The reaction mixture was concentrated, treated with 20% NaOH (150 mL) and extracted with CH₂Cl₂ (4×). The combined organic layers were dried with Na₂SO₄, filtered and concentrated to give a white solid (14.23 g, ~93%).

The crude product (16.2 g, 68.9 mmol) was combined with 4-imidazolecarboxaldehyde (1B, 6.6 g, 68.9 mmol) and Ti(O-iPr)₄ (25 mL, 86 mmol) in CH₂Cl₂ (15 ml) and stirred at RT until the reaction mixture became clear (~1 h). Following the addition of NaBH₄ (3.3 g, 86 mmol) and EtOH (200 mL), the reaction was stirred at RT overnight and concentrated. The residue was taken up in 0.5 N NaOH and extracted with CH₂Cl₂ (4×). The combined organic layers were dried with Na₂SO₄, filtered, and concentrated. Chromatography (5-10% of 7N NH₃-MeOH in CH₂Cl₂) provided compound 38 (14.13 g, 68%) as a white solid.

Preparative Example 39

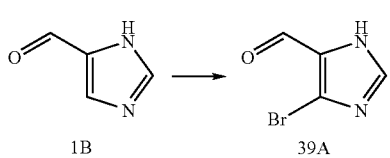

Bromine (8.0 g, 50 mmol, 2.3 eq) in anhydrous Ac₂O (40 mL) was added dropwise to a solution of 1B (2.08 g, 21.7 mmol) and NaOAc (18.7 g, 228 mmol, 10.5 eq) in anhydrous HOAc (200 mL) over a period of 1 h at RT. The resulting mixture was stirred at RT for 2.5 h and then concentrated. The residue was partitioned between Et₂O (200 mL) and water (200 mL), the layers were separated and the aqueous layer was extracted with Et₂O (200 mL). The combined organic phase was dried, concentrated and chromatographed (EtOAc) to afford 5-bromo-4-formyl imidazole 39A (1.00 g, 26%) as white crystals.

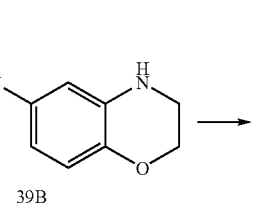

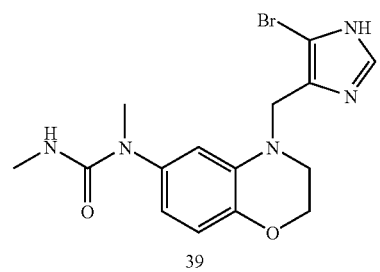

In a manner similar to that found in Example 1, 39A was treated with 39B (Example 6) to afford the title compound 39. LCMS m/z 280 (MH+).

Preparative Example 40

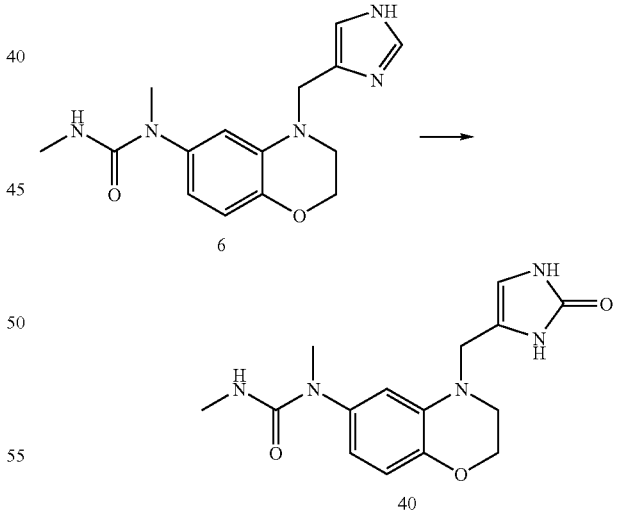

A mixture of 6 (0.25 g, 0.83 mmol) and NaHCO₃ (0.7 g, 8.3 mmol) in 1:1 THF—H₂O (20 mL) was stirred vigorously for 10 min and then treated with phenyl chloroformate (PhOC-OCl, 0.26 mL, 2.1 mmol). The reaction was stirred at RT for 2 h and then diluted with EtOAc. The organic layer was isolated, dried over Na₂SO₄ and concentrated. The resulting residue was dissolved in MeOH, treated with Et₃N (0.6 mL, 4.3 mmol) and stirred overnight. The solution was concen- Preparative Example 41

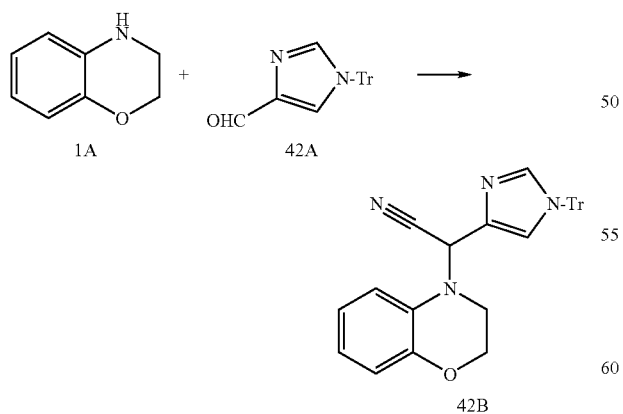

1A → 41

A mixture of 1A (0.2 g, 1.5 mmol) and imidazole-4-carboxaldehyde (1B, 0.16 g, 1.6 mmol) in $CH_2Cl_2$ (5 mL) was treated with $Ti(OiPr)_4$ (0.55 mL, 1.88 mmol), stirred at RT overnight, and then treated with $Et_2AlCN$ (2 mL, 1M/toluene). After 18 h, EtOAc, $H_2O$, and celite were added. Filtration and subsequent chromatography (0-10% of 7N $NH_3$-MeOH in $CH_2Cl_2$) provided 41 as a yellow solid (0.178 g, 50%). LCMS m/z 241 (MH+).

Preparative Example 42

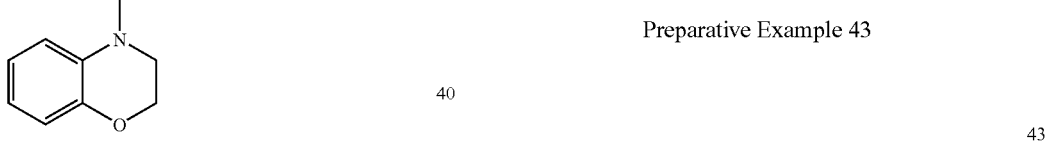

41

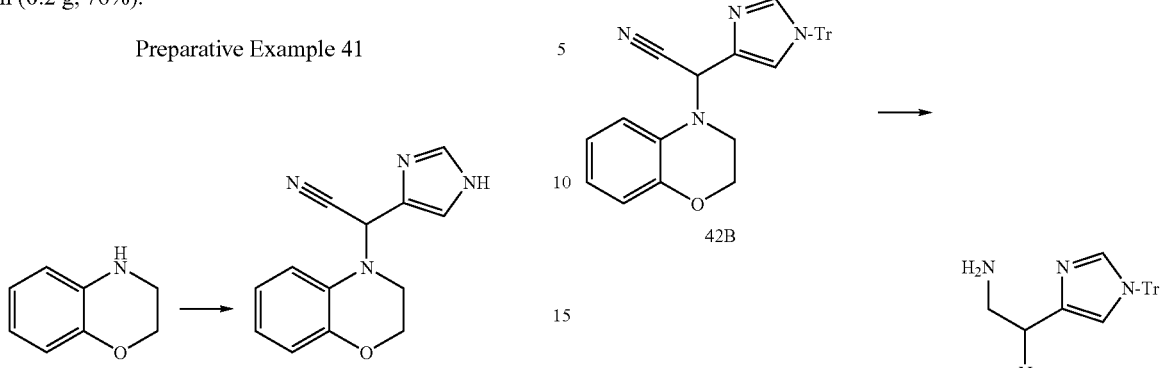

1A + 42A → 42B

In a manner similar to that found in Example 41, a mixture of 1A and 42A (Journal of Medicinal Chemistry, 1971, 14, 883) was treated sequentially with $Ti(OiPr)_4$ and $Et_2AlCN$ to provide the compound 42B.

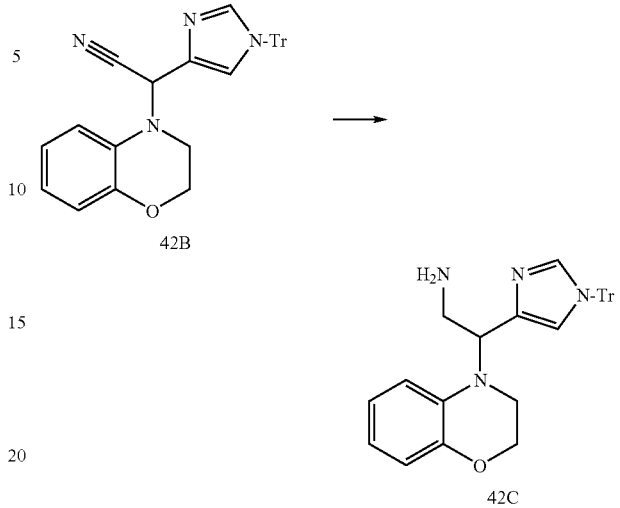

42B → 42C

A solution of 42B (0.2 g, 0.41 mmol) in 1N $NH_3$-MeOH (50 mL) was treated with
Raney Ni and hydrogenated (50 psi $H_2$) overnight at RT. Filtration and subsequent chromatography (0-7% of 7N $NH_3$-MeOH in $CH_2Cl_2$) provided 42C as a yellow film (0.15 g, 74%).

A mixture of 42C (145 mg, 0.3 mmol) in $CH_2Cl_2$ (2 mL) was treated with TFA (0.5 mL) and $Et_3SiH$ (0.05 mL). The reaction mixture was stirred at RT overnight and then concentrated. Chromatography (2-15% of 7 N $NH_3$-MeOH in $CH_2Cl_2$) provided the title compound 42 (69 mg, 95%) as a yellow oil. LCMS m/z 245 (MH+).

Preparative Example 43

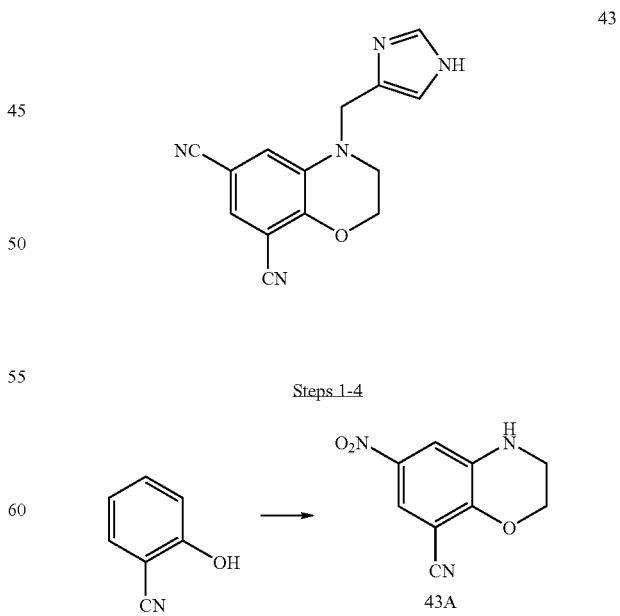

43A

In a manner similar to that described in Examples 19 and 3,2-cyanophenol was subjected to bis-nitration with $HNO_3$, selective reduction with SnCl$_2$, cyclization with chloroacetyl chloride, and reduction with BH$_3$—SMe$_2$ to provide 43A.

Step 5

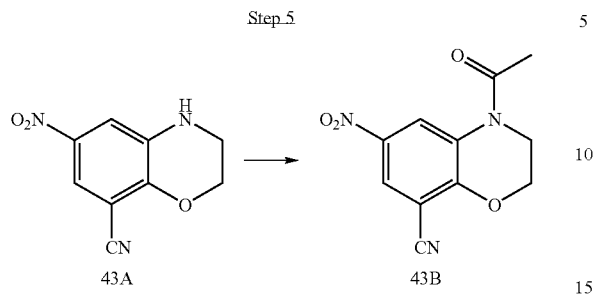

A mixture of 43A (0.65 g, 3.2 mmol) and Et$_3$N (0.9 mL, 6.3 mmol) in CH$_2$Cl$_2$ (60 mL) was treated with Ac$_2$O (6 mL) and DMAP (0.15 g) and then refluxed for 2 d. The reaction was then cooled, washed with 1N HCl (2×), washed with brine, dried over Na$_2$SO$_4$, and concentrated. Chromatography (10-100% of EtOAc/hexanes) provided 43B as a yellow solid (0.688 g, 88%).

Steps 5-8

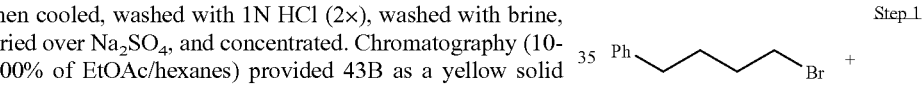

In a manner similar to that described in Example 3 (Step 4), 43B was hydrogenated with Pd/C.

A mixture of the aniline product (0.080 g, 0.38 mmol) in 6M HCl (0.5 mL) was treated with a solution of NaNO$_2$ (27 mg, 0.39 mmol) at 0° C. After 0.5 h, the solution was neutralized with sat. aq. Na$_2$CO$_3$ and then added dropwise to solution of CuCN (37 mg, 0.41 mmol) and NaCN (40 mg, 0.82 mmol). The resulting mixture was stirred at 60° C. overnight and then filtered.

The brown precipitate (44 mg) was collected and then treated with 10% aq. NaOH (0.5 mL) for 2 h at RT. The reaction was then diluted with H$_2$O and extracted with CH$_2$Cl$_2$ (3×). The combined organic layers were washed with brine, dried over Na$_2$SO$_4$, and concentrated. Chromatography (20-100% of EtOAc/hexanes) provided 43C as a beige solid (0.0.15 g).

In a manner similar to that described in Example 3 (Step 3), 43C was converted to the title compound 43. LCMS m/z 266 (MH+).

Preparative Example 44

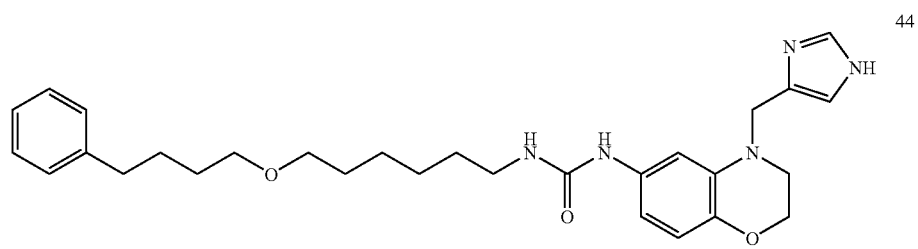

Step 1

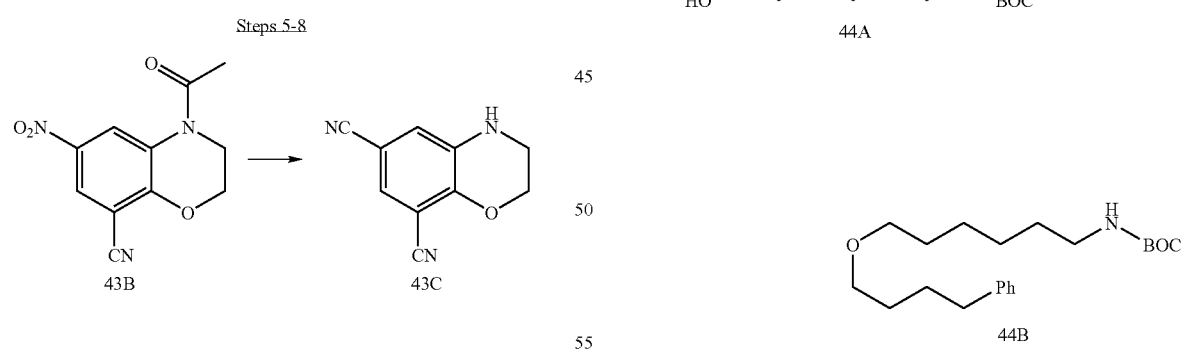

A solution of 4-phenylbutyl bromide (0.98 g, 4.6 mmol) and 44A (1.0 g, 4.6 mmol) in 10 mL of benzene was treated sequentially with Bu$_4$NHSO$_4$ (0.16 g, 0.46 mmol) and 50% aqueous NaOH (2.4 mL, 46 mmol, added slowly). After stirring at RT under N$_2$ for 20 h, the solvent was removed. The reaction mixture was then diluted with H$_2$O, extracted with EtOAc, washed with H$_2$O (3×) and brine, dried over Na$_2$SO$_4$, and filtered. The filtrate was concentrated and chromatographed (5-10% EtOAc/hexanes) to provide 44B (0.7 g, 44%).

Steps 2-3

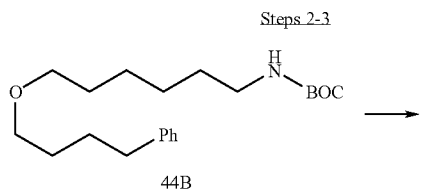

Step 1

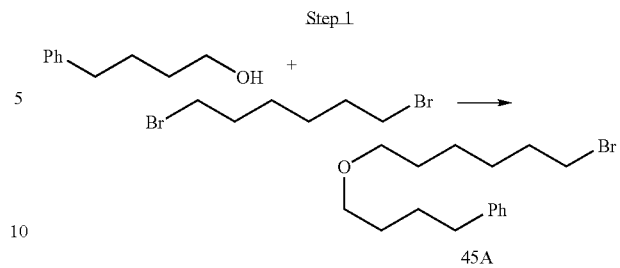

A solution of 4-phenylbutanol (2.50 g, 16.6 mmol) and 1,6-dibromohexane (8.12 g, 33.2 mmol) in anhydrous THF (30 mL) was treated slowly with NaH (1.0 g, 24.9 mmol) at RT. After refluxing under $N_2$ for 20 h, the mixture was cooled to RT, and quenched with $H_2O$. The products were extracted with ether, washed with brine, dried over $Na_2SO_4$, and filtered. The filtrate was concentrated and chromatographed (2% EtOAc/hexanes) to give 45A (3.3 g, 63%).

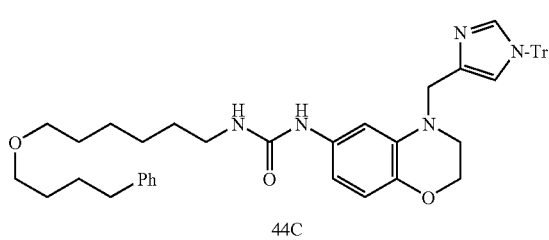

Steps 2-4

To a solution of 44B (0.2 g, 0.57 mmol) in 5 mL of $CH_2Cl_2$ (5 mL) was added TFA (1.5 mL). After stirring at RT for 1.5 h, the solution was cooled to 0° C. and treated with concentrated aqueous $NH_3$ (until pH=10-11). The mixture was extracted with $CH_2Cl_2$, dried over $Na_2SO_4$, and filtered. The filtrate was concentrated to give an unstable amine (0.12 g, 84%) which was immediately taken up in $CH_2Cl_2$ (8 mL) and treated with compound 7B (0.21 g, 0.44 mmol) and $Et_3N$ (0.17 mL, 1.2 mmol). After the mixture was cooled to -50° C., triphosgene (0.04 g, 0.13 mmol) was added to the solution. The mixture was stirred at -50° C. under $N_2$ for 1 h, then slowly warmed up to RT, and stirred under $N_2$ overnight. After adding 5% aqueous NaOH (10 mL), the products were extracted with $CH_2Cl_2$, dried over $Na_2SO_4$, and filtered. Chromatography (2% MeOH/EtOAc) provided 44C (0.2 g, 67%).

Step 4

A mixture of 44C (0.13 g) in 3N HCl-MeOH (8 mL) was heated at 60° C. under $N_2$ for 1.5 h, cooled to 0° C. and neutralized with concentrated aqueous $NH_3$. The solution was concentrated, taken up in $H_2O$ and extracted with $CH_2Cl_2$. The organic extract was dried over $Na_2SO_4$, filtered and chromatographed (5% $NH_3$-MeOH in $CH_2Cl_2$) to give the title compound 44 (0.05 g, 62%). LCMS m/z 506 (MH+).

Preparative Example 45

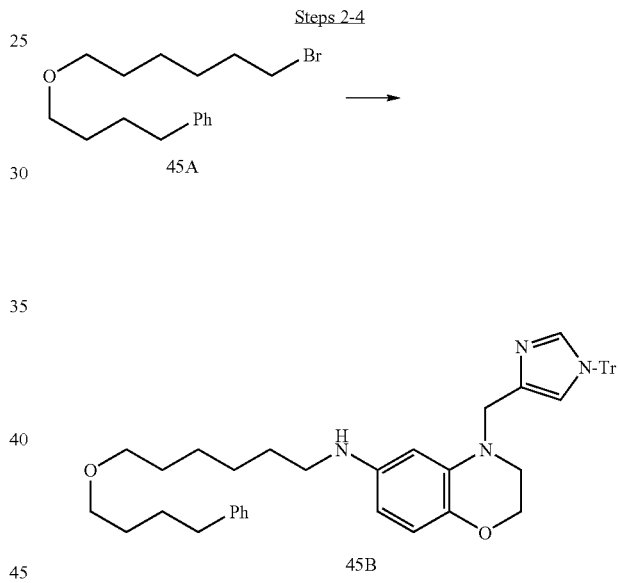

To a solution of 45A (0.07 g, 0.21 mmol) and 7B (0.1 g, 0.21 mmol) in toluene (3 mL) and DMF (0.5 mL) was added DIPEA (0.07 mL, 0.42 mmol) at RT. After heating at 80° C. under $N_2$ for 20 h, the mixture was concentrated, taken up in $CH_2Cl_2$, washed with $H_2O$ (3×) and brine, dried over $Na_2SO_4$, and filtered. Chromatography (60% EtOAc/hexanes) provided 45B (0.04 g, 27%).

45

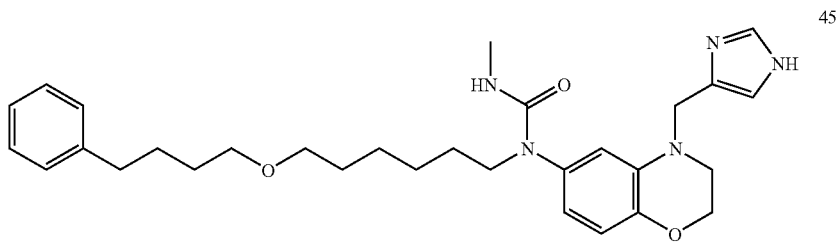

In a manner similar to that described in Example 5 (Step 3) and Example 44 (Step 4), 45B was sequentially treated with MeNCO and HCl to provide the title compound 45. LCMS m/z 520 (MH+).

Preparative Example 46

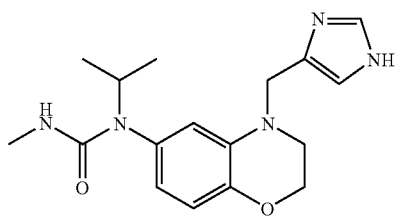

Compound 46A (from Example 38, Step 2, 250 mg, 1 mmol) was taken up in DCE (10 mL) and treated sequentially with 2-methoxypropene (0.14 mL, 1.5 mmol), HOAc (0.06 mL, 1.1 mmol), and NaBH(OAc)₃ (424 mg, 2.0 mmol). The reaction mixture was stirred at RT overnight, quenched with 1.0 N NaOH and extracted with CH₂Cl₂ (3×20 mL). The combined organic layers were washed with brine, dried, and then concentrated. Chromatography (EtOAc/hexanes) afforded 46B (190 mg, 65%).

Steps 1-2

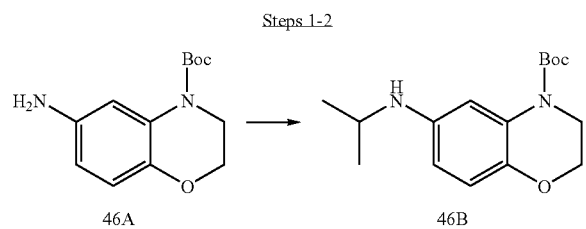

Steps 3-5

In a manner similar to that described in Example 38 (Steps 5-7), 46B was sequentially treated with MeNCO, deprotected with TFA, and treated with 4-imdazolecarboxaldehyde to provide the title compound 46. LCMS m/z 330 (MH+).

Preparative Example 47

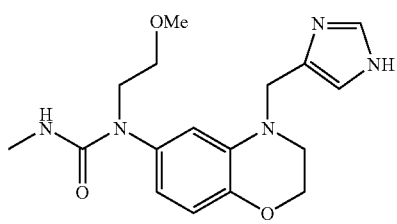

Step 1

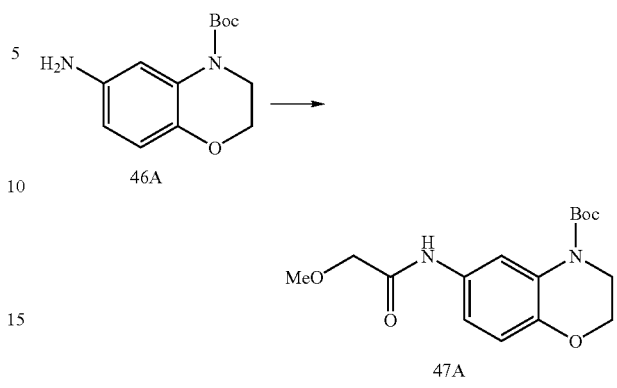

A mixture of 46A (500 mg, 2 mmol) in CH₂Cl₂ (10 mL) was sequentially treated with methoxyacetyl chloride (0.22 mL, 2.4 mmol) and TEA (0.56 mL, 4.0 mmol). The reaction mixture was stirred at RT overnight, quenched with sat. NaHCO₃, and extracted with CH₂Cl₂ (2×20 mL). The combined organic layers were washed with brine, dried, and concentrated. Chromatography (EtOAc/hexanes) afforded 47A (610 mg, 95%).

Steps 2-5

In a manner similar to that described in Example 38 (Steps 4-7), 47A was reduced with BH₃—SMe$_e$, treated with MeNCO, deprotected with TFA, and treated with 4-imdazolecarboxaldehyde to provide the title compound 47. LCMS m/z 346 (MH+)

Preparative Example 48

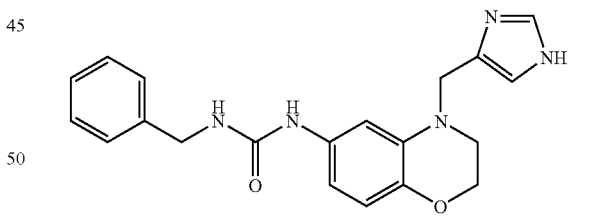

Steps 1-2

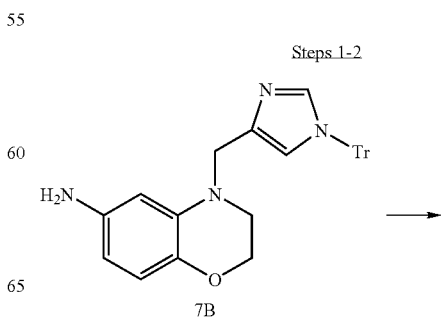

-continued

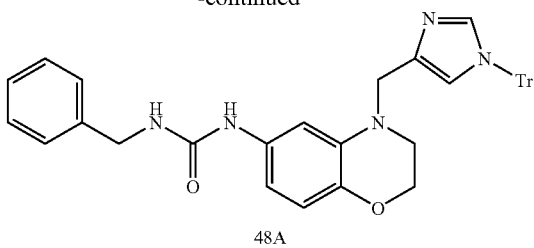

48A

A solution of 7B (140 mg, 0.3 mmol) in anhydrous CH$_2$Cl$_2$ (5 mL) was treated with benzyl isocyanate (48 mg, 0.36 mmol). The reaction mixture was stirred at RT overnight and then concentrated. Chromatography afforded 48A (130 mg, 72%).

In a manner similar to that described in Example 42 (Step 3), 48A was deprotected with with TFA and Et$_3$SiH to provide the title compound 48. LCMS m/z 364 (MH+).

Preparative Example 49

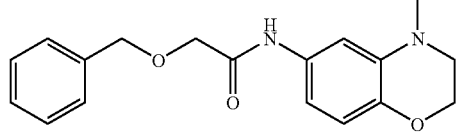

49

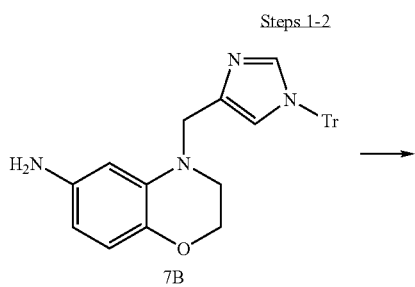

Steps 1-2

7B

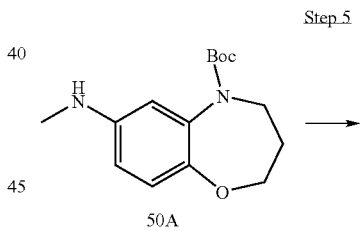

49A

A mixture of 7B (1.0 g, 2.12 mmol), benzyloxyacetic acid (0.46 g, 2.75 mmol), EDCl (0.61 g, 3.18 mmol) and HOBt (0.42 g, 3.18 mmol) in DMF were stirred at RT for 1 d. The reaction was quenched with 0.5 N aq. NaOH (50 mL) and extracted with CH$_2$Cl$_2$. The combined extracts were washed with brine, dried (Na$_2$SO$_4$) and concentrated. Preparative TLC chromatography (5% NH$_3$-MeOH in CH$_2$Cl$_2$) provided 49A (0.52 g).

In a manner similar to that described in Example 42 (Step 3), 49A was deprotected with TFA and Et$_3$SiH to provide the title compound 49. LCMS m/z 379 (MH+).

Preparative Example 50

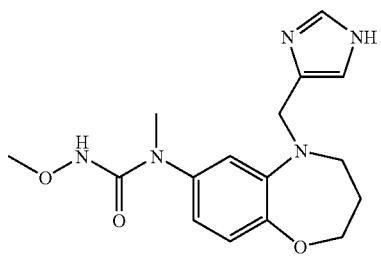

50

Steps 1-4

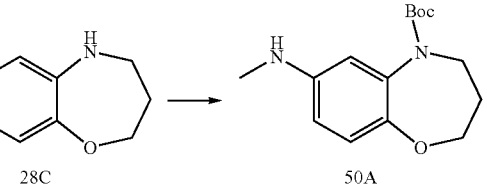

28C → 50A

In a manner similar to that described in Example 5 (Steps 1-2) and Example 6 (Steps 1-2), compound 28C was converted to 50A.

Step 5

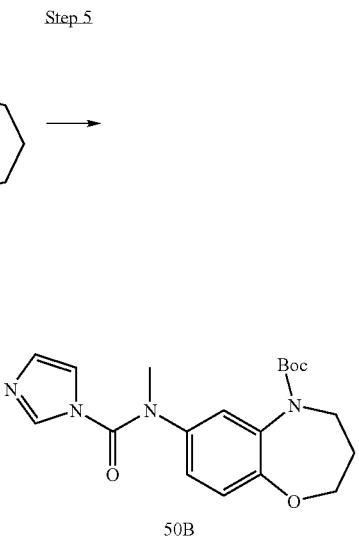

50A

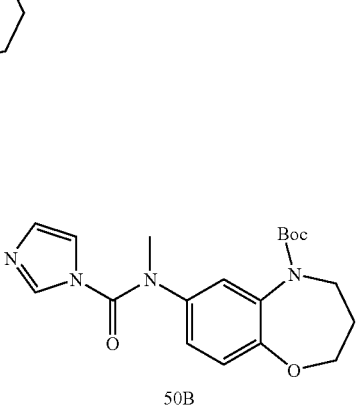

50B

A mixture of 50A (0.247 g, 0.99 mmol) in anhydrous DCM (5 mL) was treated with carbonyldiimidazole (0.32 g, 1.97 mmol) and Et$_3$N (0.28 mL, 1.97 mmol) and then stirred at RT overnight. The reaction was washed with water and extracted with DCM (3×10 mL). The combined organic layer was dried (MgSO$_4$), filtered, and concentrated under vacuum to give compound 50B.

Steps 6-8

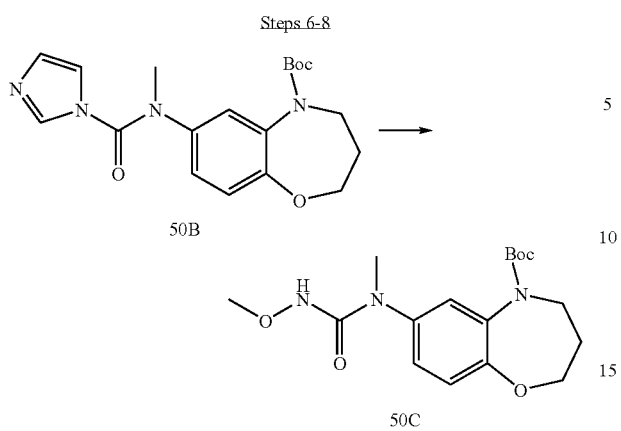

A solution of 50B was in anhydrous MeCN (5 mL) in a sealed tube was treated with MeI (2 mL). The sealed reaction mixture was heated to 55° C. for 3 h, cooled to RT and concentrated. The residue was dissolved in anhydrous THF (5 mL) and then treated with MeONH$_2$—HCl (0.25 g, 2.97 mmol) and DIEA (0.53 mL, 2.97 mmol). After stirring at RT overnight, the reaction was quenched with saturated NH$_4$Cl solution and concentrated under vacuum. The residue was diluted with water and extracted with EtOAc (3×10 mL). The combined organic layer was dried (MgSO$_4$), filtered, and concentrated under vacuum to afford crude compound 50C (279 mg, 80% for 3 steps).

In a manner similar to that found in Example 5 (Step 4) and Example 3 (Step 3), compound 50C was deprotected and converted to the title compound 50. MS m/z=332 (MH+).

Preparative Example 51

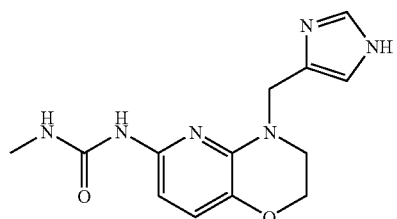

Steps 1-4

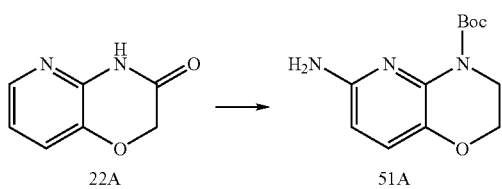

In a manner similar to that described in Example 21 (Step 1), Example 3 (Step 2), Example 5 (Step 1) and Example 3 (Step 4), compound 22A was sequentially nitrated, reduced with BH$_3$—SMe$_2$, treated with Boc$_2$O, and hydrogenated to yield compound 51A.

Steps 5-7

In a manner similar to that described in Example 5 (Steps 3-5), 51A was treated with MeNCO, deprotected with TFA, and converted to the title compound 51. MS m/z=289 (MH+).

Preparative Example 52

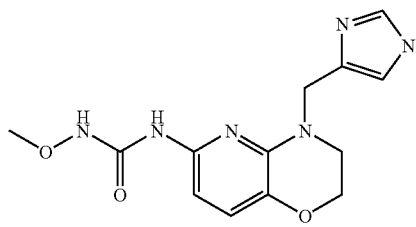

Steps 1-3

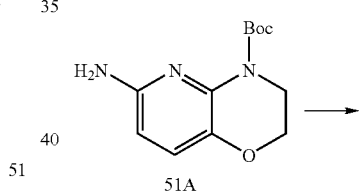

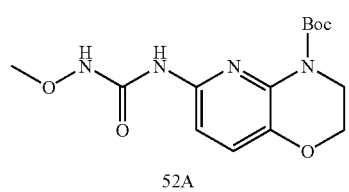

To a solution of 51A (740 mg, 2.95 mmol) in DCM (30 ml) was added 4-nitrophenylchloroformate (891 mg, 4.42 mmol) and pyridine (0.48 ml, 5.90 mmol). After stirring overnight at RT, TLC indicated consumption of the starting material. MeONH$_2$—HCl salt (739 mg, 8.84 mmol) in anhydrous THF (10 ml) and DIEA (1.57 mL, 8.84 mmol) were then sequentially added. After stirring at RT overnight, the reaction was quenched by water, concentrated, diluted with water and extracted with EtOAc. The organic phase was dried (MgSO$_4$), filtered, and concentrated. Flash chromatography (20-50% of EtOAc/hexanes) provided 52A (650 mg, 68%).

In a manner similar to that found in Example 5 (Step 4) and Example 3 (Step 3), 52A was converted to 52. MS m/z=305 (MH+).

Preparative Example 53

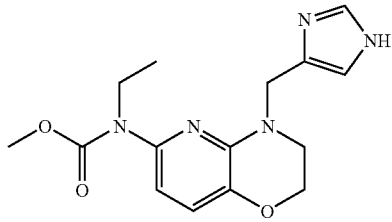
53

Steps 1-3

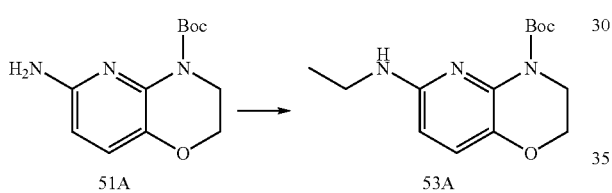

To compound 51A (100 mg, 0.40 mmol) in DCE (5 mL) was added acetaldehyde (0.045 mL, 0.80 mmol). The mixture was stirred at RT for 1 h and then treated with MeOH (3 mL) and NaBH$_4$ (45.5 mg, 1.2 mmol). After stirring at RT overnight, the reaction was quenched by 2N NaOH solution, concentrated, diluted with water and extracted with EtOAc. The organic phase was dried (MgSO4), filtered, and concentrated under vacuum to give a residue 53A (40 mg, 36%).

In a manner similar to that found in Example 3 (Step 5), Example 5 (Step 4) and Example 3 (Step 3), 53A was treated with ClCO$_2$Me/pyridine, deprotected with TFA and converted to the title compound 53. MS m/z=318 (MH+).

Preparative Example 54

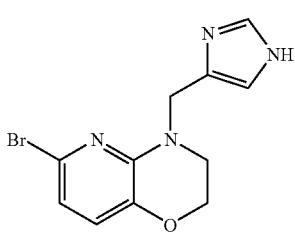
54

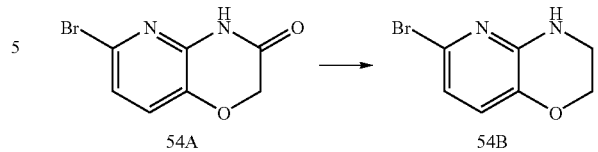

In a manner similar to that found in Example 3 (Step 2), compound 54A (see WO 2006/020561) was reduced with BH$_3$—SMe$_2$ to provide 54B.

Compound 54B was then elaborated into 54 (MS m/z=295, MH+) as previously described in Example 3 (Step 3).

Preparative Example 55

55

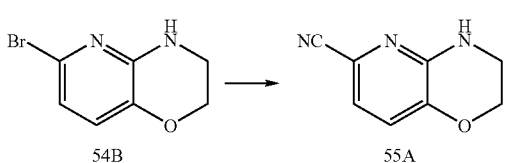

Steps 1-2

A Smith process vial was charged with a stir bar, compound 54B (0.33 g, 1.54 mmol), CuCN (0.276 g, 3.08 mmol) and DMF (3 mL). The reaction vessel was sealed and heated to 120° C. for 3 h under microwave irradiation. After cooling, the reaction mixture was transferred to a round bottom flask and concentrated under vacuum. Compound 55A was obtained quantitatively by continuous extraction with EtOAc in a Soxlet apparatus.

Compound 55A was then elaborated into 55 (MS m/z=242, MH+) as previously described in Example 3 (Step 3).

Preparative Example 56

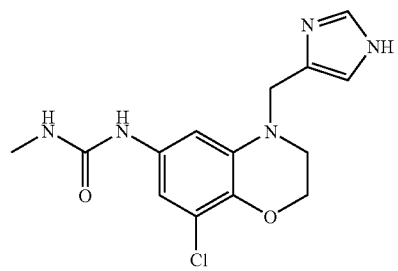

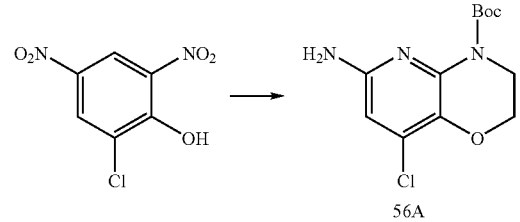

In a manner similar to that previously described, 2-chloro-4,6-dinitrophenol was sequentially reduced with SnCl$_2$ (Example 19, Step 2), treated with chloroacetyl chloride, reduced with BH$_3$—SMe$_2$ (Example 3, Steps 1-2), protected with Boc$_2$O (Example 5, Step 1), and reduced again with SnCl$_2$ to yield compound 56A.

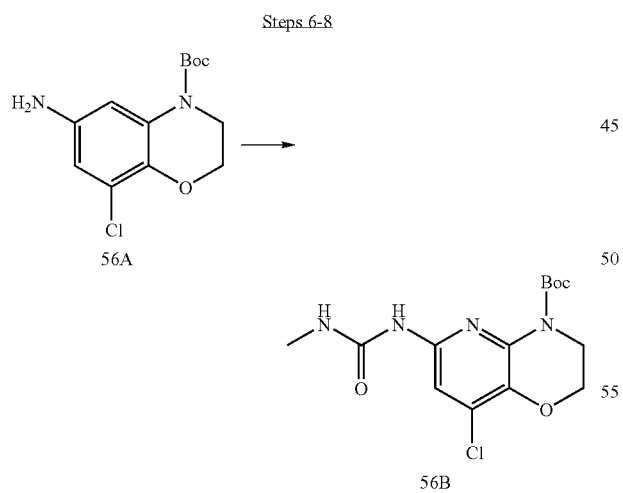

To a solution of compound 56A (0.29 g, 1 mmol) in anhydrous DCM (3 ml) was added 4-nitrophenylchloroformate (0.24 g, 1.2 mmol) and pyridine (0.13 ml, 1.57 mmol). After stirring overnight at RT, the reaction was quenched with sat. NH$_4$Cl solution and extracted with DCM. The organic phase was then concentrated. A solution of this residue in CH$_3$CN (5 mL) was treated with 40% MeNH$_2$ in H$_2$O (20 mL) and heated in a sealed tube at 90° C. overnight. The mixture was cooled, stirred at RT overnight, and then quenched with water. The reaction was concentrated, diluted with water and extracted with EtOAc. The organic phase was dried (MgSO$_4$), filtered, and concentrated to give 56B.

As described previously in Example 5 (Step 4) and Example 3 (Step 3), 56B was deprotected and converted to 56. MS m/z=322 (MH+).

Preparative Example 57

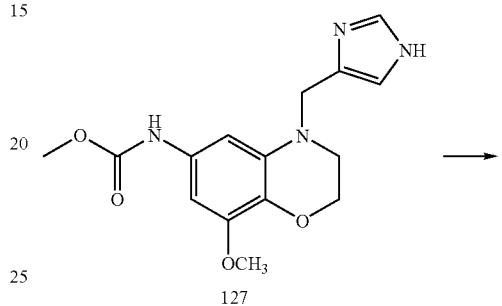

Compound 127 (0.388 g, 1.22 mmol) was dissolved in anhydrous DCM (10 mL) and cooled to −78° C. To this solution was added 1.0M BBr$_3$ in DCM (6.1 mL) dropwise. The reaction mixture was stirred at −78° C. for 30 min and then at RT for 3 h. The reaction was quenched with water and neutralized with 2N NaOH solution. The mixture was separated and the aqueous phase was extracted with DCM (3×10 mL). The organic phase was dried (MgSO$_4$), filtered, and concentrated under vacuum. The residue was purified by flash column chromatography (DCM containing 2 to 8% of 7N NH$_3$ in MeOH) to afford compound 57 in 30% yield. MS m/z=305 (MH+).

Preparative Example 58

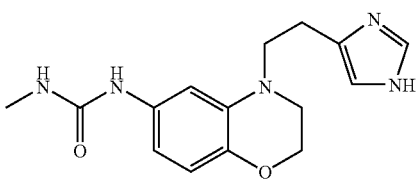

Step 1

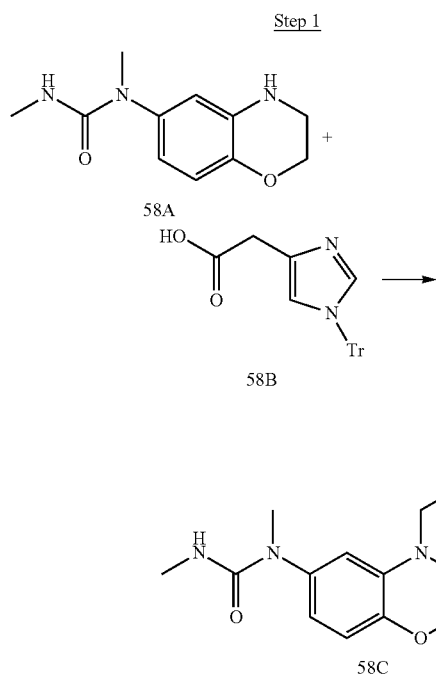

In a manner similar to that described in Example 37, compound 58A (prepared in Example 6) and 58B (Bioconjugate Chemistry, 13, 333-350, 2002) were reacted with HATU to provide 58C. MS m/z=572 (MH+)

Steps 2-3

A solution of 58C (720 mg, 1.3 mmol) in THF (50 mL) was treated with $BH_3$—$SMe_2$ (5 mL, 2 M in THF) and heated at 80° C. for 12 h. After it was cooled to 25° C., MeOH (15 mL) was added dropwise until bubbling ceased. The solvent was removed and partitioned between EtOAc and water. The organic phase was dried over $Na_2SO_4$ and concentrated. The crude residue was stirred in DCM/TFA (1:3, 5 mL) at 25° C. for 4 h. Solvent was removed and the residue was partitioned between EtOAc and water. The organic phase was dried and concentrated. Column chromatography and preparative TLC (DCM containing 5% of 7N $NH_3$/MeOH) gave 58. MS m/z=316 (MH+).

Preparative Example 59

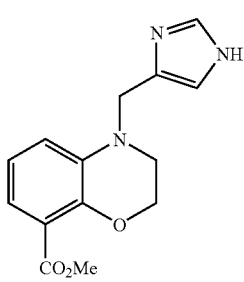

Steps 1-3

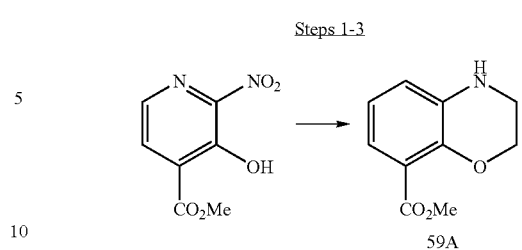

In a manner similar to that described in Example 3 (Step 4 then Steps 1-2), methyl 2-hydroxy-3-nitrobenzoate was sequentially hydrogenated, treated with chloroacetylchloride, and reduced with $BH_3$—$SMe_2$ to yield compound 59A.

Step 4

Compound 59A was treated with 4-imidazolecarboxaldehyde to afford the title compound 59 in a manner similar to that described in Example 3 (Step 3). MS m/z=274 (MH+).

Preparative Example 60

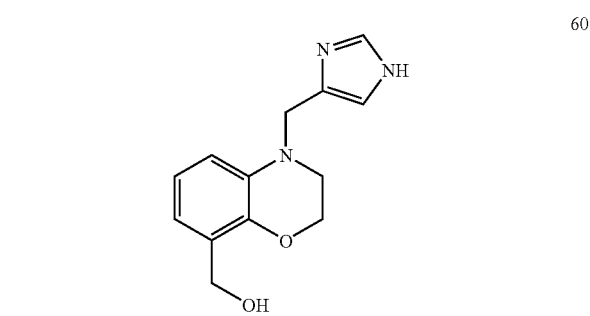

Steps 1-2

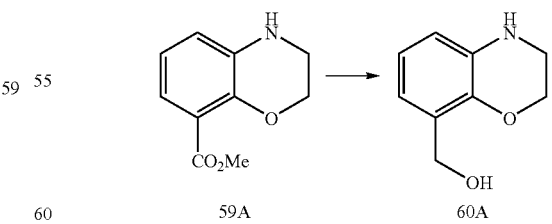

A mixture of $LiBH_4$ (44 mg, 2 mmol) and 59A (400 mg, 2 mmol) in THF (50 mL) was stirred at RT for 4 h and then concentrated. The residue was partitioned between EtOAc and water. The organic phase was dried and concentrated to give 60A (300 mg, 91%).

Compound 60A was converted to 60 in a manner similar to that described in Example 3 (Step 3). MS m/z=246 (MH+).

Preparative Example 61

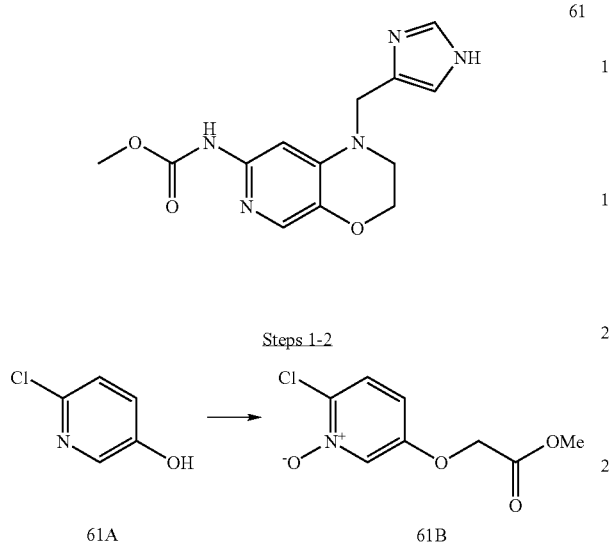

To 2-chloro-5-hydroxypyridine (61A) in acetone (80 mL) was added K$_2$CO$_3$ (8.96 g, 65 mmol) and methylchloroacetate (2.54 mL, 29 mmol). The mixture was heated at 60° C. for 4 h. After cooling to RT, the mixture was filtered, and the solids were washed with acetone (50 mL). The filtrate was concentrated in vacuo to give 4.3 g intermediate (92% yield). The intermediate (4.3 g, 21.3 mmol) was dissolved in CHCl$_3$ (75 mL) and treated with m-chloroperbenzoic acid (4.78 g, 27.7 mmol). The resulting solution was heated at 50° C. for 4 h, then stirred at RT overnight. The mixture was treated with sodium sulfate, filtered and concentrated in vacuo. Flash column chromatography (5%-10% MeOH in DCM) provided 61B (3.46 g, 75%).

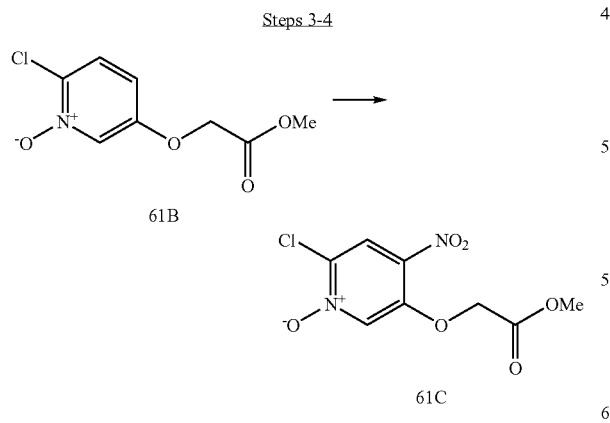

The N-oxide 61 B (1.0 g, 4.61 mmol) was dissolved in H$_2$SO$_4$ (2 mL) at 0° C. HNO$_3$ (1 mL) was added slowly over several minutes. The reaction mixture was then placed in an oil bath heated to 40° C. The temperature was slowly raised to 75° C. over 1 h and then maintained there for 2 h. The mixture was then poured over ice and adjusted to pH 9 by the addition of 50% NaOH. Water was removed in vacuo, and the resultant solids were washed with MeOH to yield crude nitro pyridine N-oxide intermediate (2.6 g). A portion of this intermediate (1.33 g, 5.3 mmol) was dissolved in MeOH (50 mL) and treated with H$_2$SO$_4$ (1 mL). The mixture was heated at 70° C. for 2 h and then concentrated. The residue was treated with 1N NaOH (20 mL) and EtOAc (50 mL). The solution was extracted with EtOAc (2×50 mL). The combined organic extracts were dried over sodium sulfate, filtered and concentrated in vacuo to give compound 61C (1.4 g, 100%).

A mixture of 61C (0.06 g, 0.23 mmol) in MeOH (2 mL) was treated with iron powder (0.09 g, 1.61 mmol) and HOAc (0.08 mL). The resulting solution was heated at 70° C. for 4 h. The hot solution was filtered through a pad of celite and concentrated. The residue was taken up in MeOH (2 mL) and treated with K$_2$CO$_3$ (0.073 g, 0.53 mmol). After heating at 65° C. for 2 h, the solvent was removed in vacuo and the product purified by preparative TLC (5% MeOH in DCM) to give compound 61D (0.032 g, 76%).

In a manner similar to that found in Example 3 (Step 2) and Example 5 (Step 1), compound 61D was reduced and protected to give compound 61E.

A mixture of 61E (0.250 g, 0.91 mmol), benzophenoneimine (0.152 mL, 0.91 mmol), tris(dibenzylideneacetone dipalladium(0) (0.004 g, 0.0045 mmol), rac-2,2'-Bis(diphenylphosphino)-1,1'-binaphthalene (0.004 g, 0.007 mmol), and NaOtBu (0.088 g, 0.91 mmol) in toluene (8 mL) in a culture tube was heated in a rotating oven at 80° C. overnight.

After cooling to RT, the contents were transferred to a round-bottomed flask and treated with several scoops of silica gel. The solvent was removed in vacuo and the product purified by flash column chromatography (10% to 50% EtOAc-hexanes) to give 61F (0.205 g, 54%).

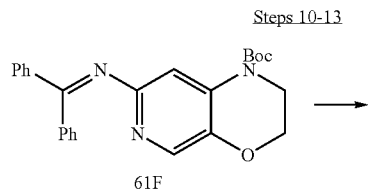

Steps 10-13

61F

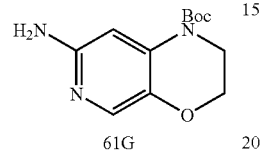

61G

A mixture of 61F (0.205 g, 0.5 mmol) in THF (4 mL) was treated with 15% aqueous citric acid solution (4 mL). The resulting solution was stirred at RT overnight. Saturated aqueous NaHCO$_3$ (5 mL) was added and the solution was extracted with EtOAc (2×25 mL). The organic extracts were dried over sodium sulfate, filtered and concentrated in vacuo. The product was purified by flash column chromatography (10% to 50% EtOAc-hexanes) to give 61G (0.114 g, 91%).

In a manner similar to that found in Example 3 (Step 5), Example 5 (Step 4) and Example 3 (Step 3), compound 61G was sequentially treated with ClCO$_2$Me, deprotected and converted the title compound 61. MS m/z=290 (MH+).

Preparative Example 62

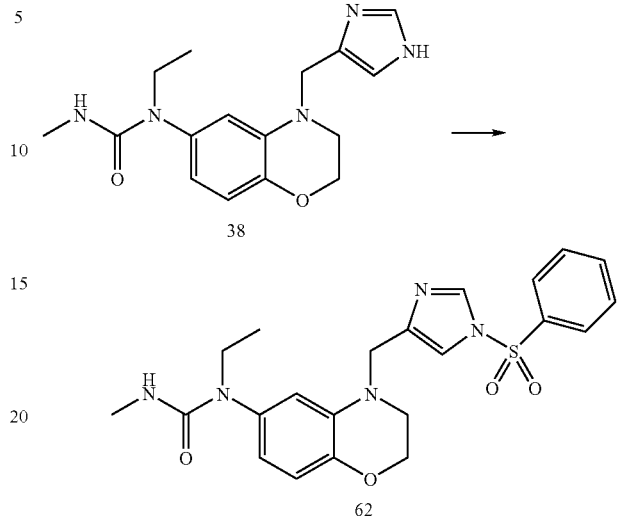

38

62

A slurry of 38 in anhydrous DCE (4 ml) and anhydrous THF (4 ml) was treated with anhydrous TEA (0.2 ml) followed by benzenesulfonyl chloride (0.070 mL). After 2 h at RT, additional benzenesulfonyl (0.2 mL) was added. The mixture was stirred for 1 h, then diluted with CH$_2$Cl$_2$, washed with brine, dried (Na$_2$SO$_4$), and concentrated. Preparative TLC chromatography (9% MeOH/CH$_2$Cl$_2$) afforded 62 (43 mg). The following compounds were prepared following essentially the same procedure as described above.

| Cpd | Structure | MS (MH+) |
|---|---|---|
| 100 | 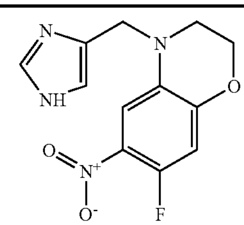 | 230 |
| 101 | 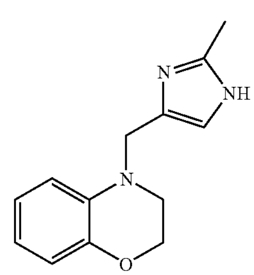 | 230 |
| 102 | 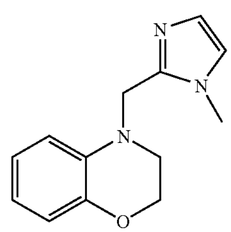 | 230 |

-continued

| Cpd | Structure | MS (MH+) |
|---|---|---|
| 103 | 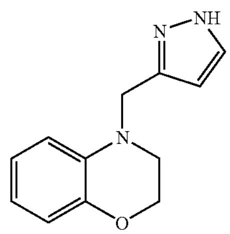 | 216 |
| 104 | 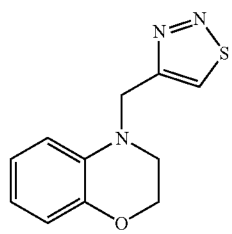 | 234 |
| 105 | 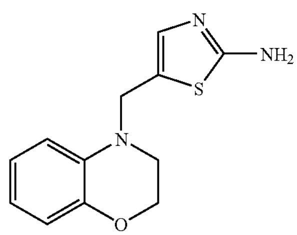 | 248 |
| 106 | 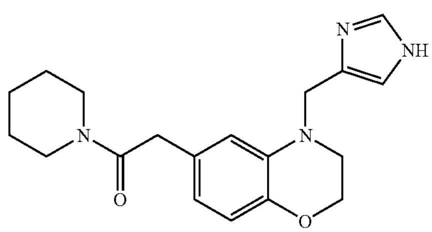 | 341 |
| 107 | 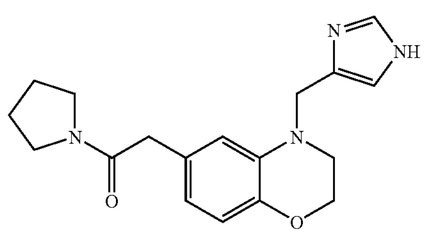 | 327 |
| 108 | 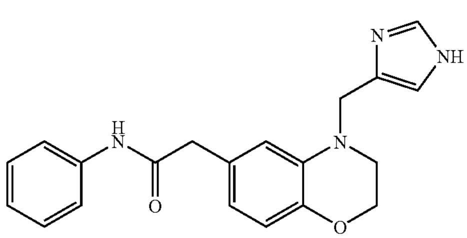 | 349 |

-continued

| Cpd | Structure | MS (MH+) |
|---|---|---|
| 109 | 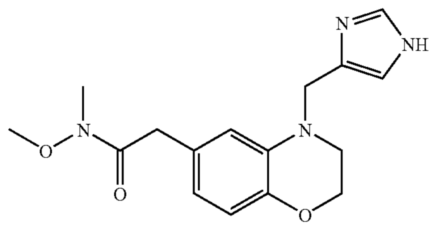 | 317 |
| 110 | 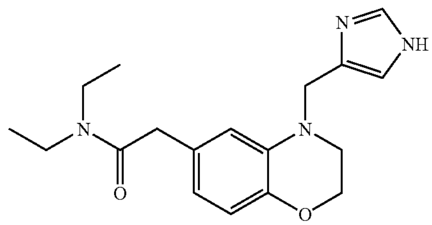 | 329 |
| 111 | 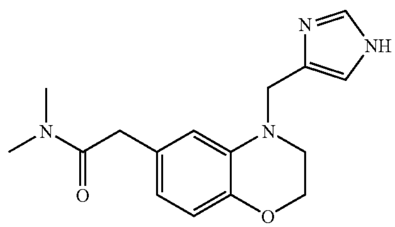 | 301 |
| 112 | 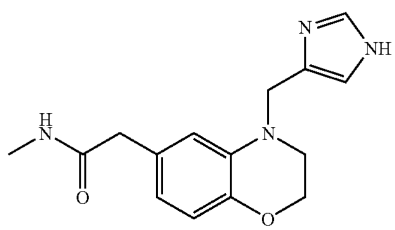 | 287 |
| 113 | 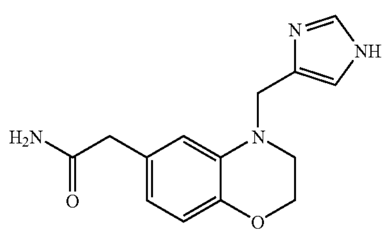 | 273 |
| 114 | 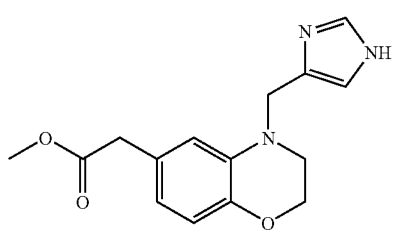 | 288 |

| Cpd | Structure | MS (MH+) |
|---|---|---|
| 115 | 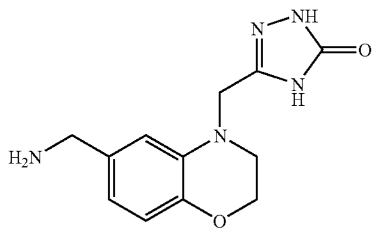 | 262 |
| 116 | 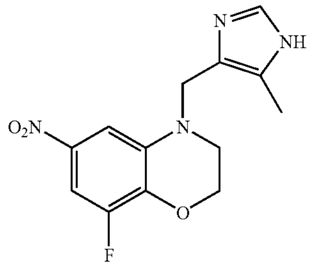 | 293 |
| 117 | 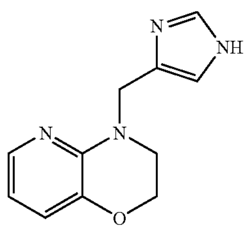 | 217 |
| 118 | 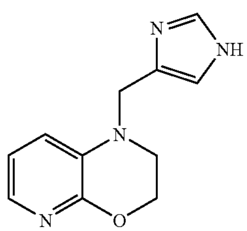 | 217 |
| 119 | 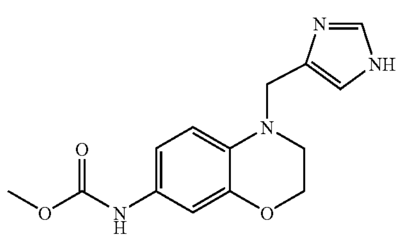 | 289 |
| 120 | 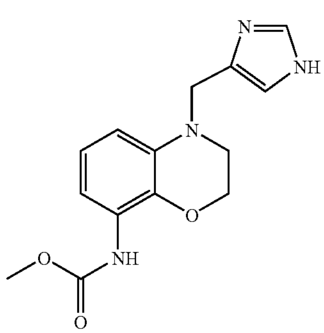 | 289 |

-continued
| Cpd | Structure | MS (MH+) |
|---|---|---|
| 121 | 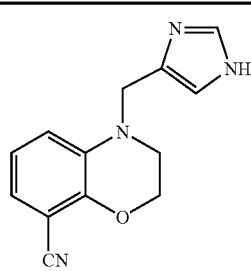 | 241 |
| 122 | 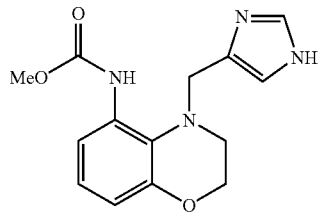 | 289 |
| 123 | 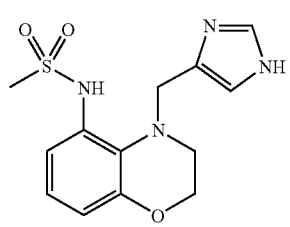 | 309 |
| 124 | 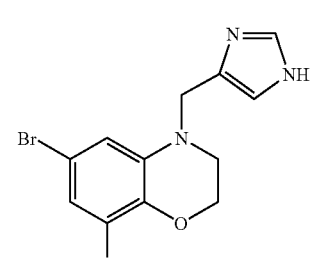 | 312 |
| 125 | 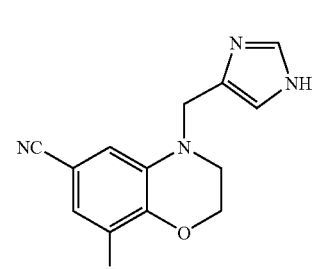 | 259 |
| 126 | 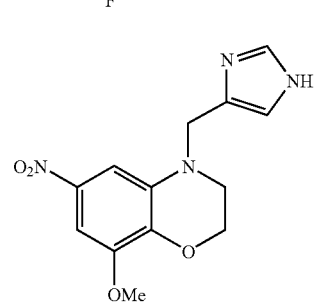 | 291 |

-continued

| Cpd | Structure | MS (MH+) |
|---|---|---|
| 127 | 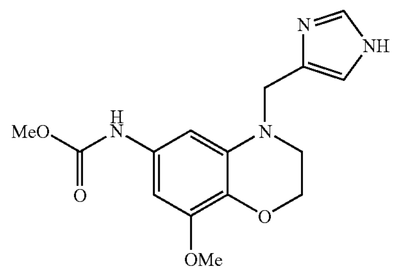 | 319 |
| 128 | 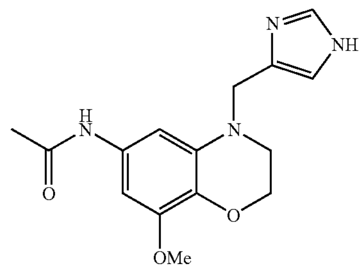 | 303 |
| 129 | 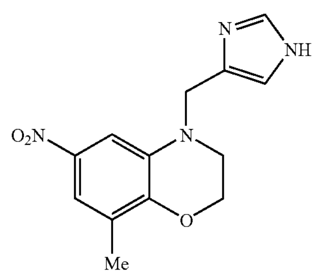 | 275 |
| 130 | 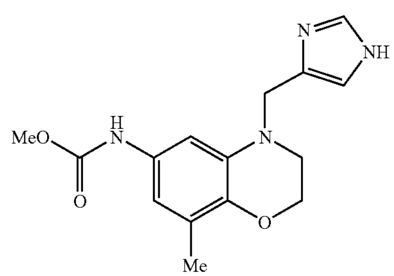 | 303 |
| 131 | 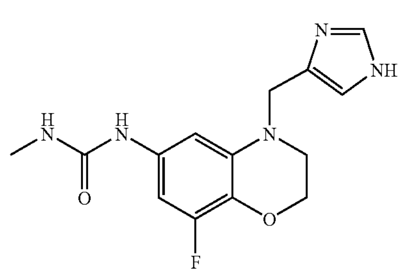 | 306 |

-continued

| Cpd | Structure | MS (MH+) |
|---|---|---|
| 132 | 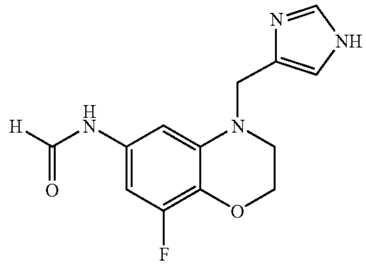 | 277 |
| 133 | 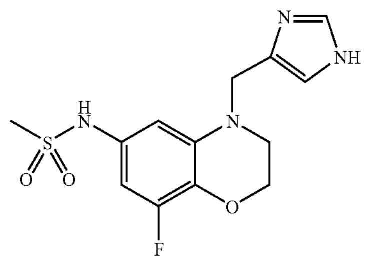 | 327 |
| 134 | 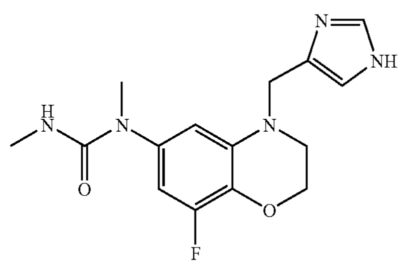 | 320 |
| 135 | 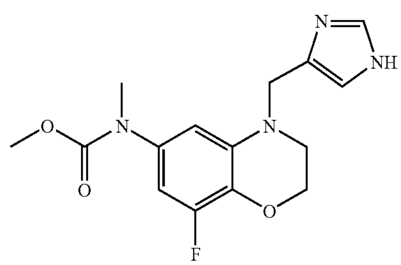 | 321 |
| 136 | 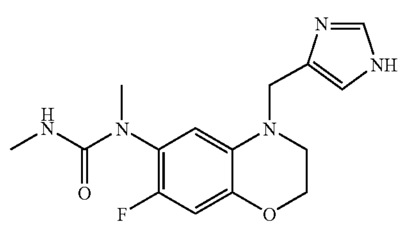 | 320 |
| 137 | 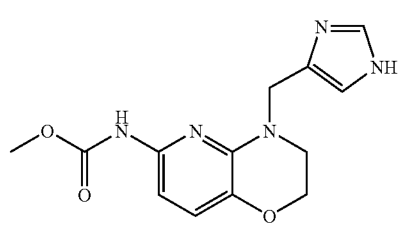 | 290 |

-continued

| Cpd | Structure | MS (MH+) |
|---|---|---|
| 138 | 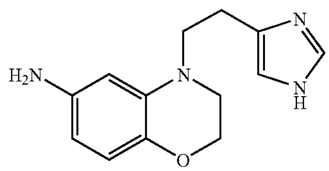 | 245 |
| 139 | 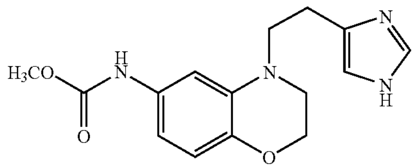 | 303 |
| 140 | 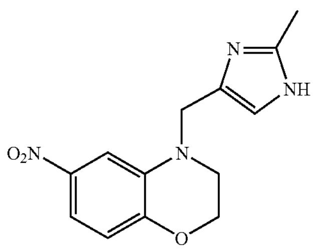 | 275 |
| 141 | 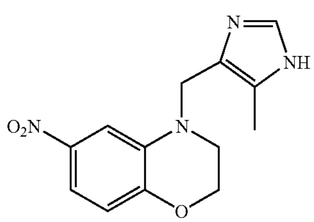 | 275 |
| 142 | 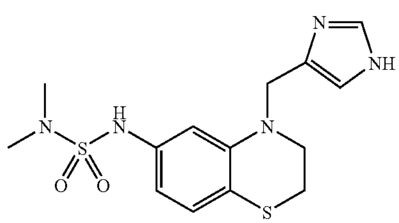 | 354 |
| 143 | 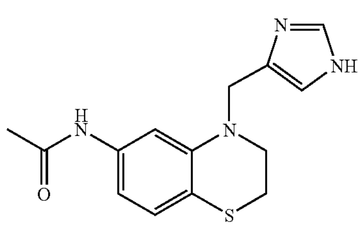 | 289 |
| 144 | 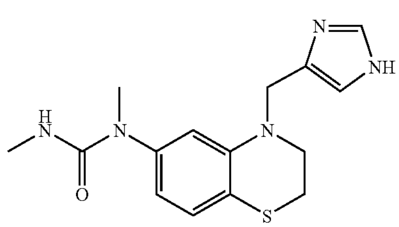 | 318 |

-continued

| Cpd | Structure | MS (MH+) |
|---|---|---|
| 145 | 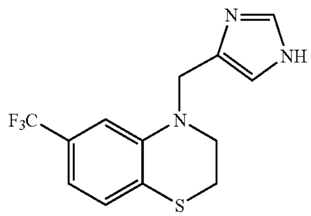 | 300 |
| 146 | 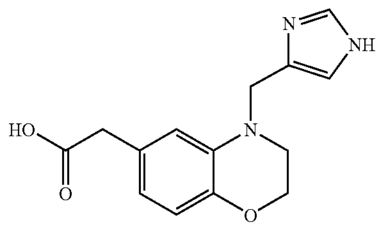 | 274 |
| 147 | 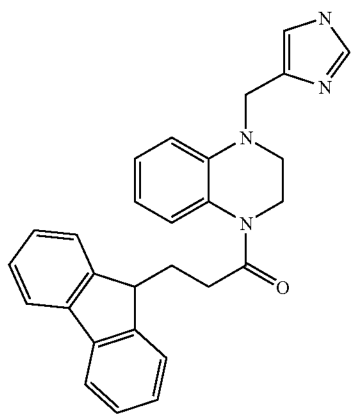 | 437 |
| 148 | 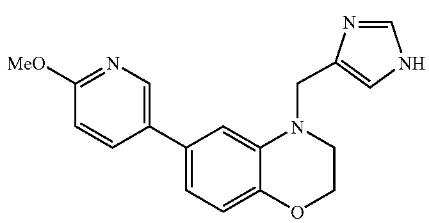 | 323 |
| 149 | 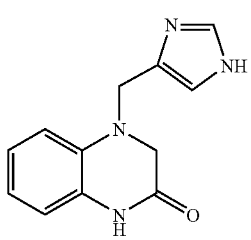 | 229 |
| 150 | 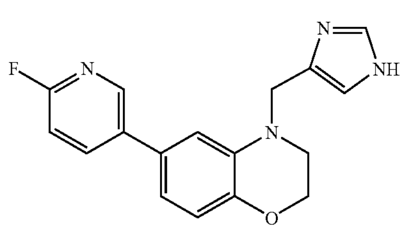 | 311 |

-continued

| Cpd | Structure | MS (MH+) |
|---|---|---|
| 151 | 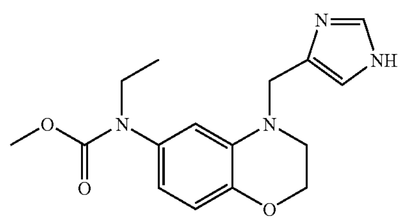 | 317 |
| 152 | 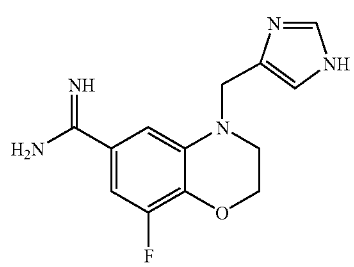 | 276 |
| 153 | 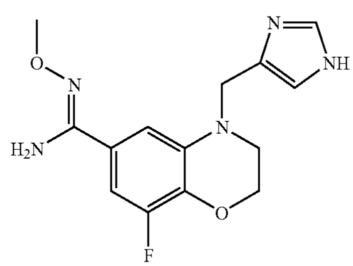 | 306 |
| 154 | 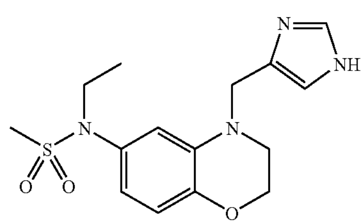 | 337 |
| 155 | 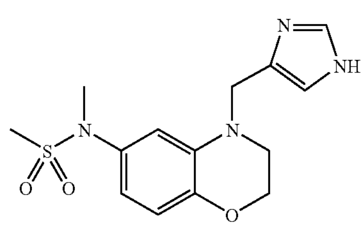 | 323 |
| 156 | 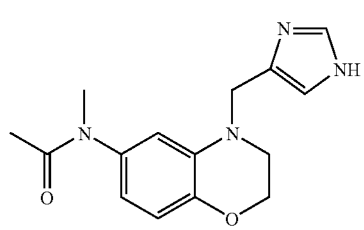 | 287 |

| Cpd | Structure | MS (MH+) |
|---|---|---|
| 157 | 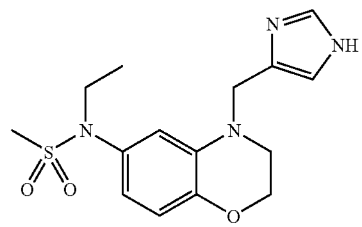 | 301 |
| 158 | 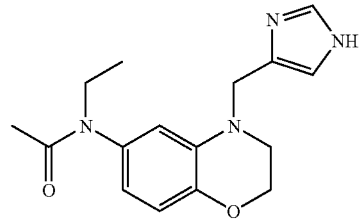 | 301 |
| 159 | 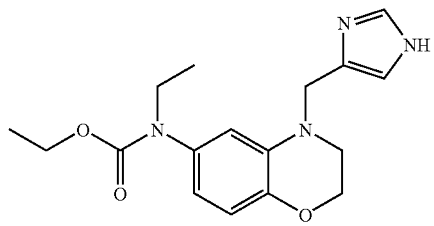 | 331 |
| 160 | 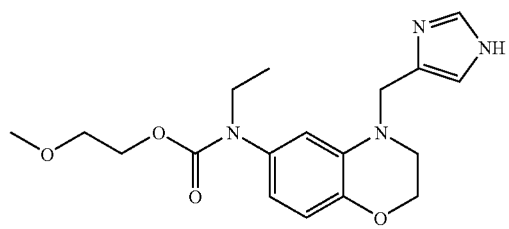 | 361 |
| 161 | 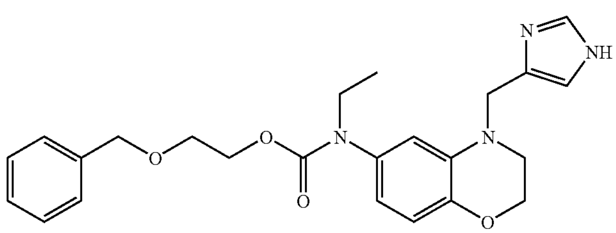 | 436 |
| 162 | 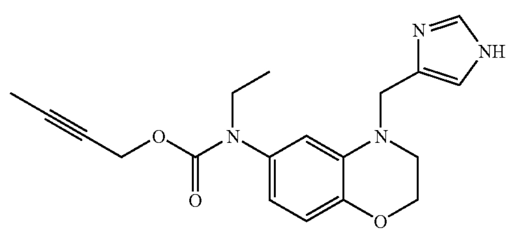 | 355 |

-continued

| Cpd | Structure | MS (MH+) |
|---|---|---|
| 163 | 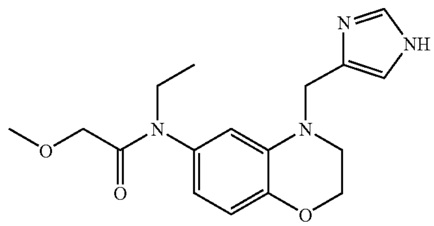 | 331 |
| 164 | 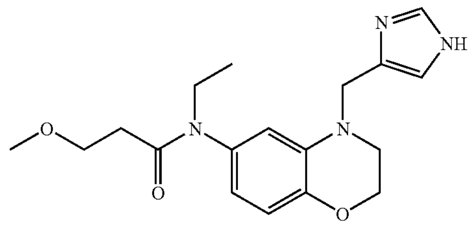 | 345 |
| 165 | 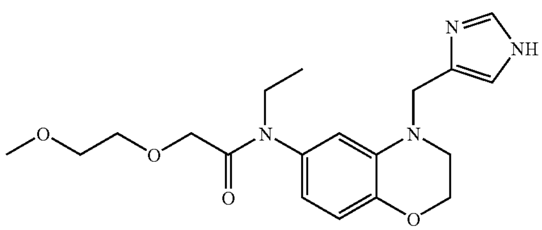 | 375 |
| 166 | 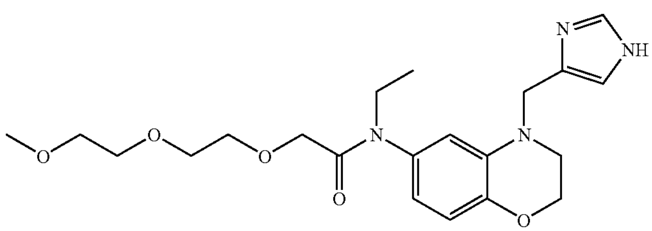 | 419 |
| 167 | 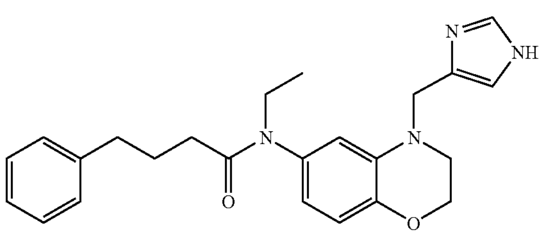 | 405 |
| 168 | 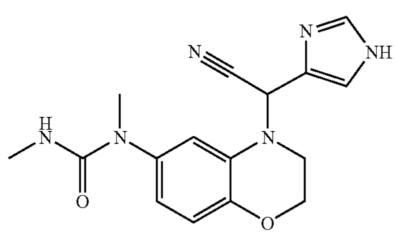 | 327 |

| Cpd | Structure | MS (MH+) |
|---|---|---|
| 169 | 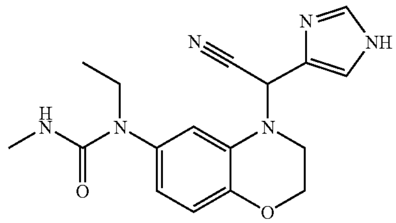 | 341 |
| 170 | 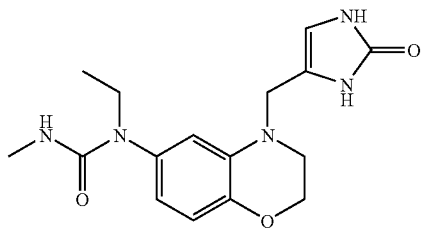 | 332 |
| 171 | 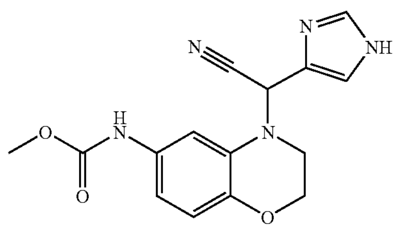 | 314 |
| 172 | 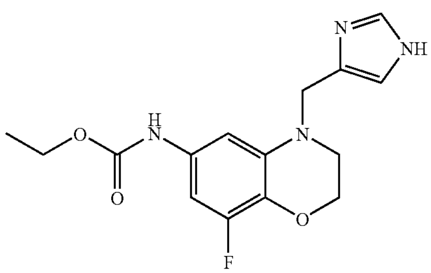 | 321 |
| 173 | 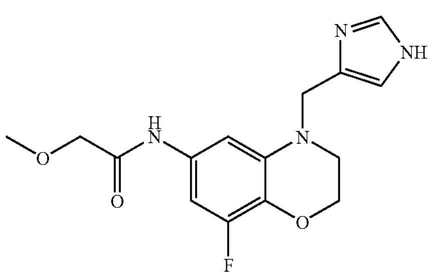 | 321 |
| 174 | 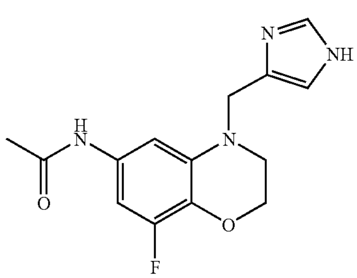 | 291 |

-continued

| Cpd | Structure | MS (MH+) |
|---|---|---|
| 175 | 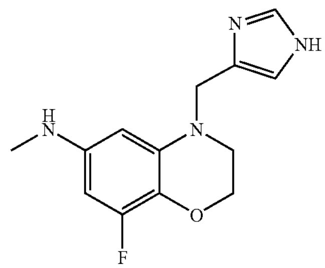 | 263 |
| 176 | 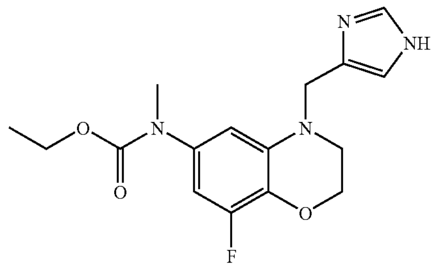 | 335 |
| 177 | 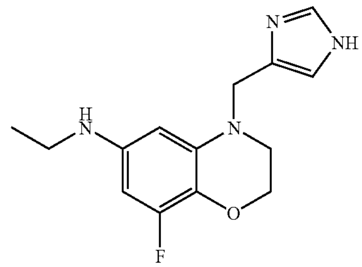 | 277 |
| 178 | 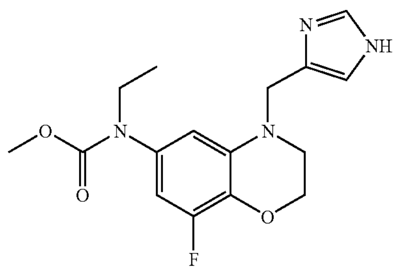 | 335 |
| 179 | 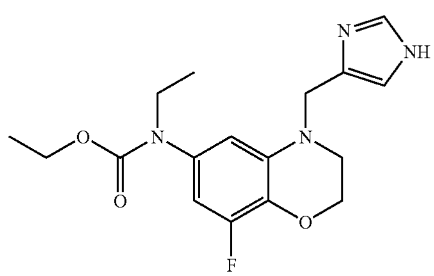 | 349 |

-continued

| Cpd | Structure | MS (MH+) |
|---|---|---|
| 180 | 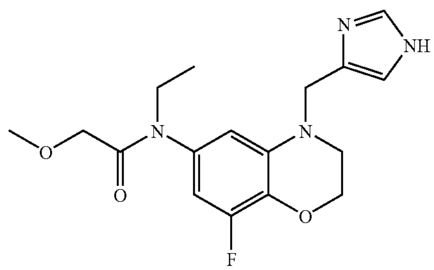 | 349 |
| 181 | 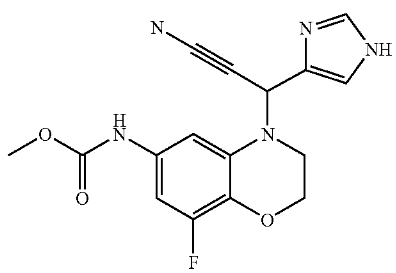 | 332 |
| 182 | 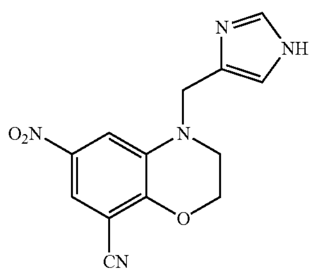 | 286 |
| 183 | 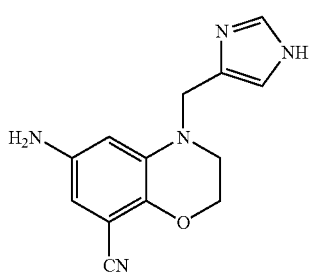 | 256 |
| 184 | 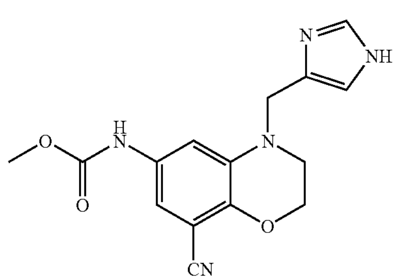 | 314 |

-continued

| Cpd | Structure | MS (MH+) |
|-----|-----------|----------|
| 185 | 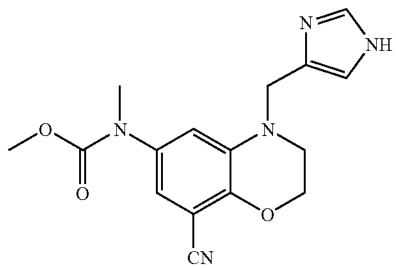 | 328 |
| 186 | 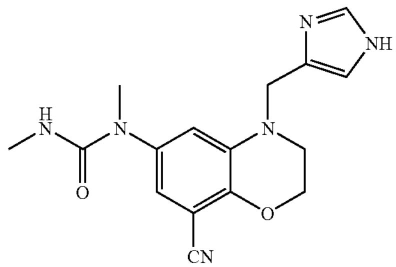 | 327 |
| 187 | 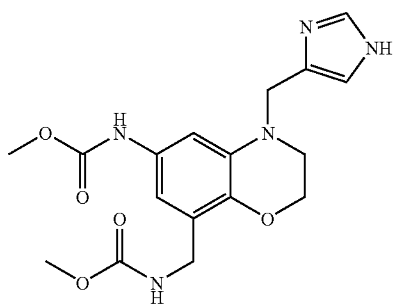 | 376 |
| 188 | 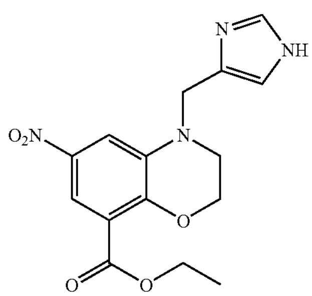 | 333 |
| 189 | 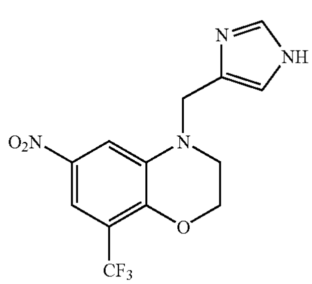 | 329 |

| Cpd | Structure | MS (MH+) |
|---|---|---|
| 190 | 6-amino-4-((1H-imidazol-5-yl)methyl)-8-(trifluoromethyl)-3,4-dihydro-2H-benzo[b][1,4]oxazine | 299 |
| 191 | methyl (4-((1H-imidazol-5-yl)methyl)-8-(trifluoromethyl)-3,4-dihydro-2H-benzo[b][1,4]oxazin-6-yl)carbamate | 357 |
| 192 | ethyl (4-((1H-imidazol-5-yl)methyl)-8-(trifluoromethyl)-3,4-dihydro-2H-benzo[b][1,4]oxazin-6-yl)carbamate | 371 |
| 193 | methyl (4-((1H-imidazol-5-yl)methyl)-8-(trifluoromethyl)-3,4-dihydro-2H-benzo[b][1,4]oxazin-6-yl)(methyl)carbamate | 371 |
| 194 | methyl (4-((1H-imidazol-5-yl)methyl)-8-(trifluoromethyl)-3,4-dihydro-2H-benzo[b][1,4]oxazin-6-yl)(ethyl)carbamate | 385 |

-continued

| Cpd | Structure | MS (MH+) |
|---|---|---|
| 195 | 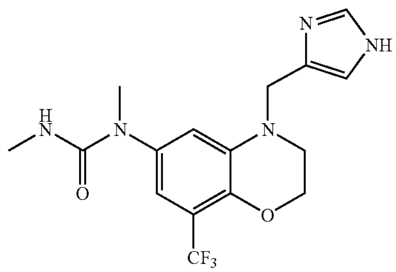 | 370 |
| 196 | 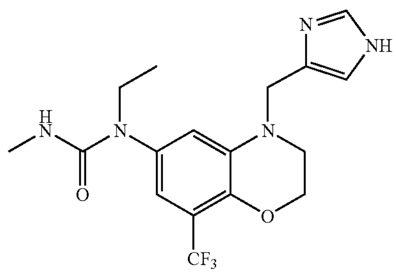 | 384 |
| 197 | 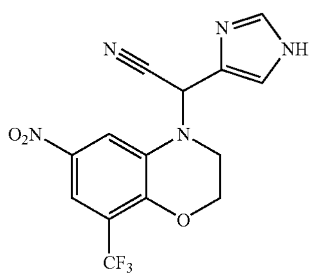 | 354 |
| 198 | 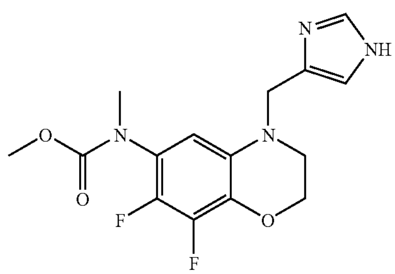 | 339 |
| 199 | 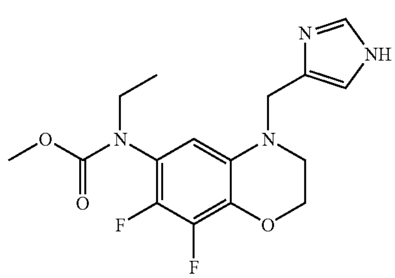 | 353 |

-continued

| Cpd | Structure | MS (MH+) |
|---|---|---|
| 200 | 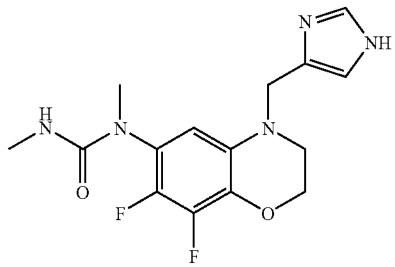 | 338 |
| 201 | 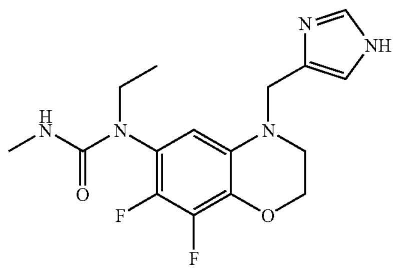 | 352 |
| 202 | 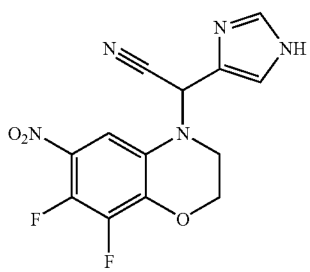 | 322 |
| 203 | 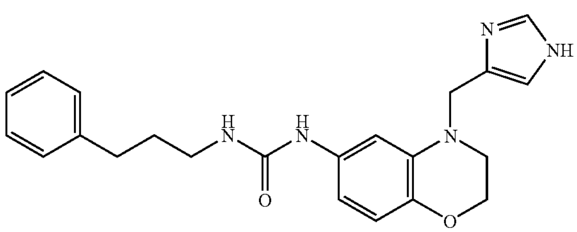 | 392 |
| 204 | 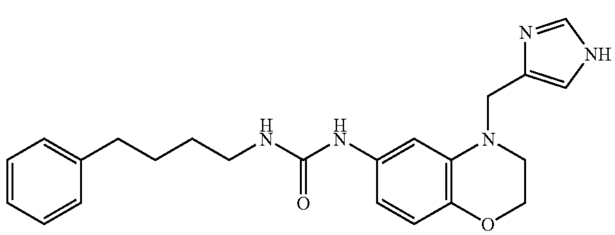 | 406 |
| 205 | 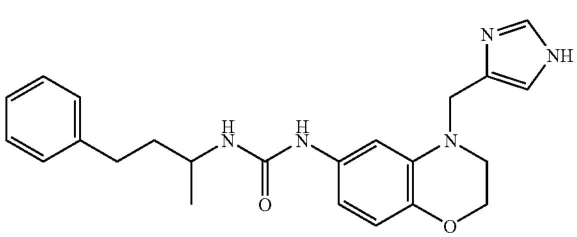 | 406 |

-continued

| Cpd | Structure | MS (MH+) |
|---|---|---|
| 206 | 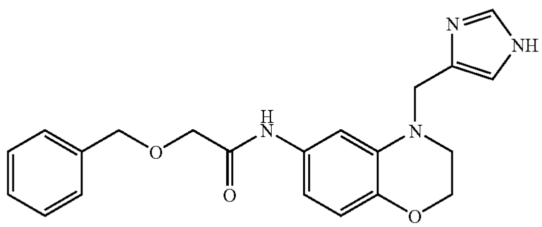 | 389 |
| 207 | 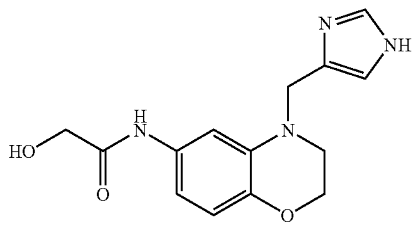 | 289 |
| 208 | 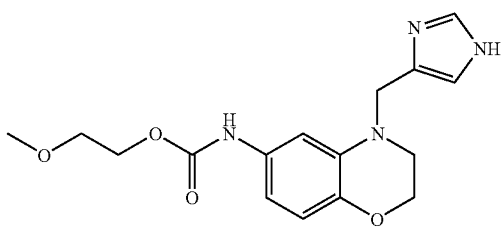 | 333 |
| 209 | 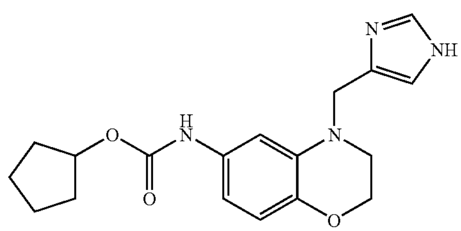 | 343 |
| 210 | 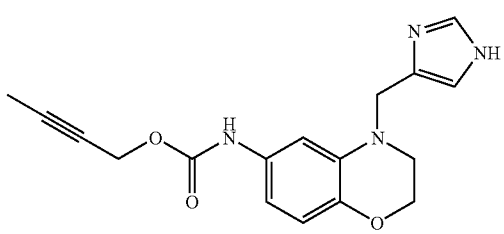 | 327 |
| 211 | 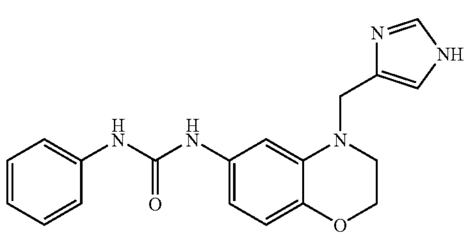 | 350 |

-continued

| Cpd | Structure | MS (MH+) |
|---|---|---|
| 212 | 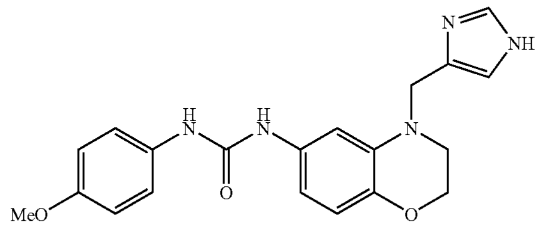 | 380 |
| 213 | 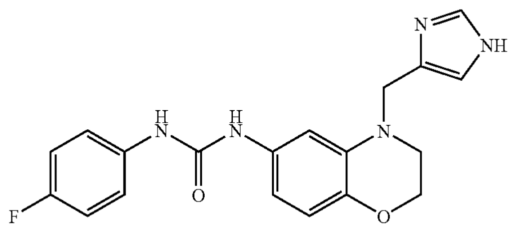 | 368 |
| 214 | 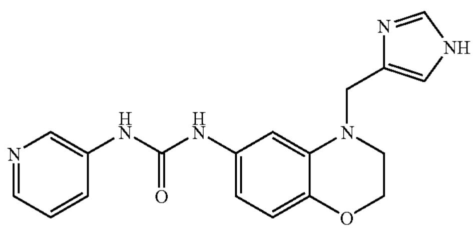 | 351 |
| 215 | 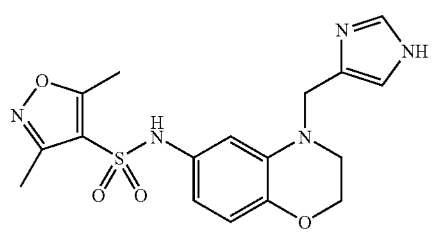 | 390 |
| 216 | 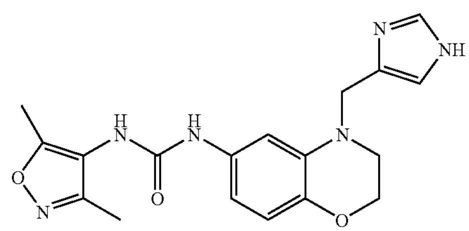 | 369 |
| 217 | 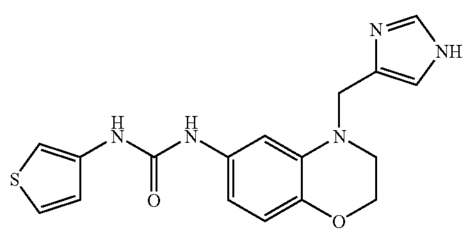 | 356 |

-continued

| Cpd | Structure | MS (MH+) |
|---|---|---|
| 218 | 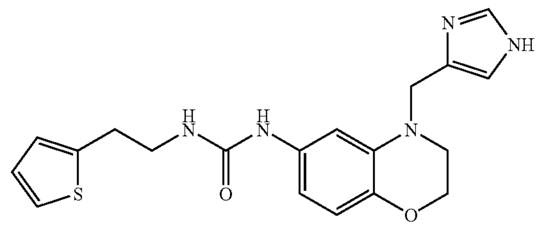 | 384 |
| 219 | 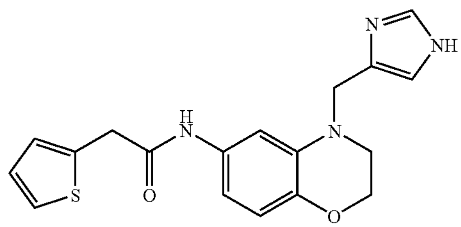 | 355 |
| 220 | 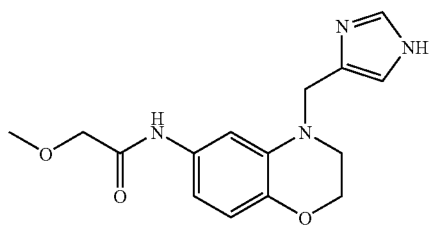 | 303 |
| 221 | 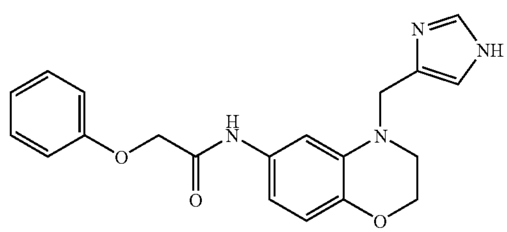 | 365 |
| 222 | 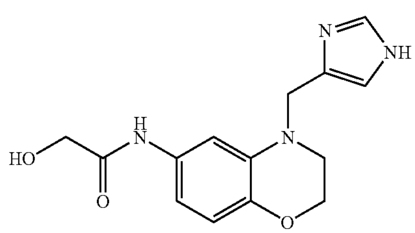 | 289 |
| 223 | 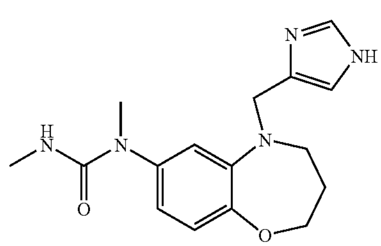 | 316 |

-continued

| Cpd | Structure | MS (MH+) |
|---|---|---|
| 224 | 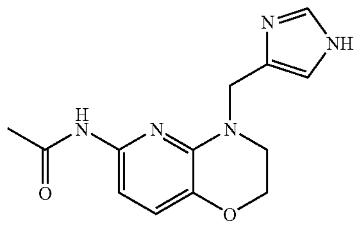 | 274 |
| 225 | 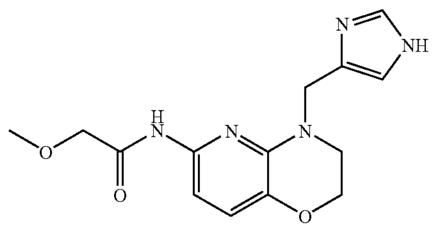 | 304 |
| 226 | 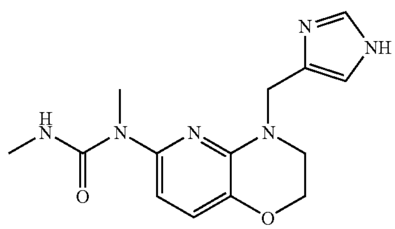 | 303 |
| 227 | 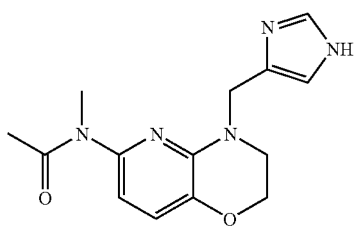 | 288 |
| 228 | 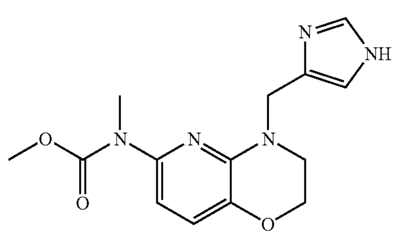 | 304 |
| 229 | 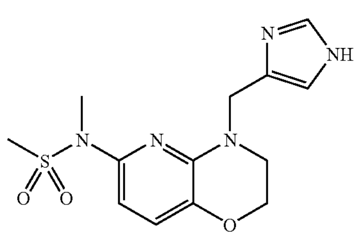 | 324 |

-continued

| Cpd | Structure | MS (MH+) |
|---|---|---|
| 230 | 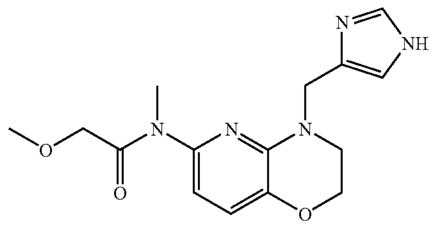 | 318 |
| 231 | 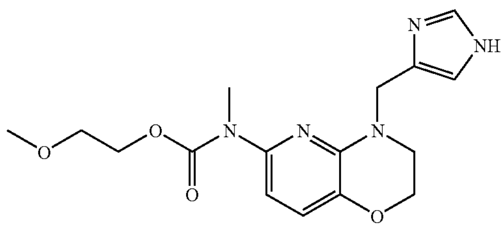 | 348 |
| 232 | 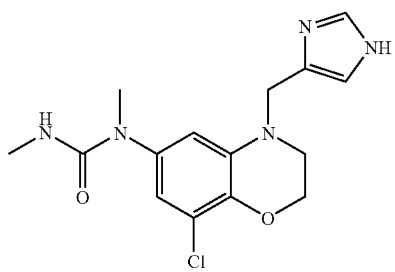 | 336 |
| 233 | 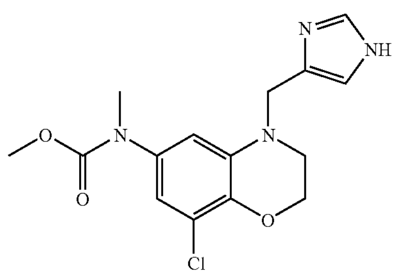 | 337 |
| 234 | 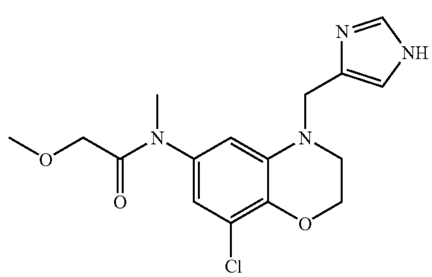 | 351 |
| 235 | 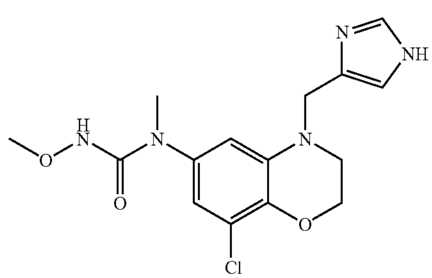 | 352 |

| Cpd | Structure | MS (MH+) |
|---|---|---|
| 236 | 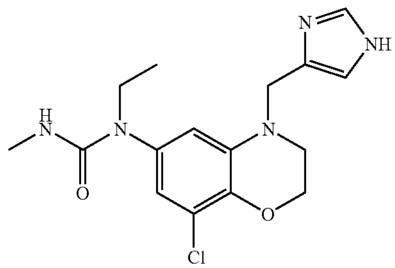 | 350 |
| 237 | 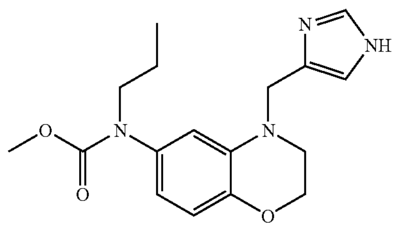 | 331 |
| 238 | 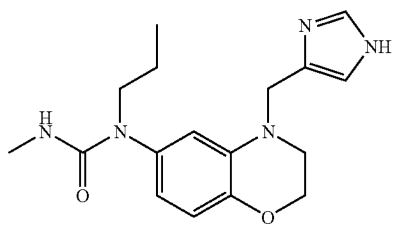 | 330 |
| 239 | 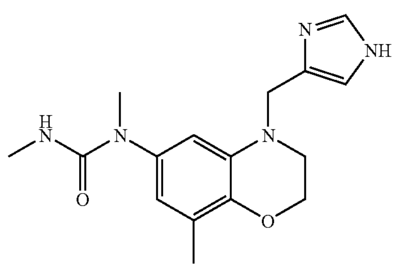 | 316 |
| 240 | 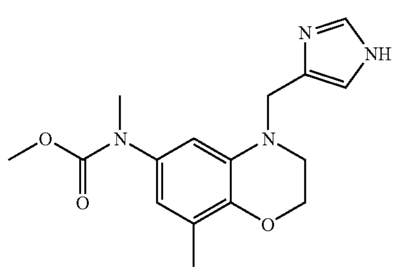 | 317 |
| 241 | 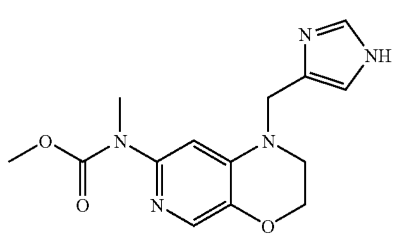 | 304 |

-continued

| Cpd | Structure | MS (MH+) |
|---|---|---|
| 242 | 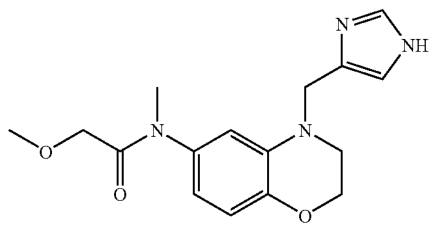 | 317 |
| 243 | 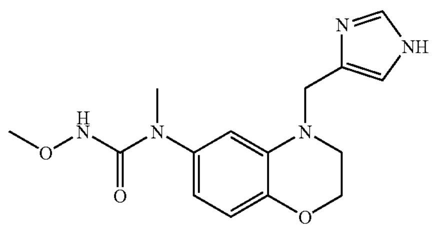 | 318 |
| 244 | 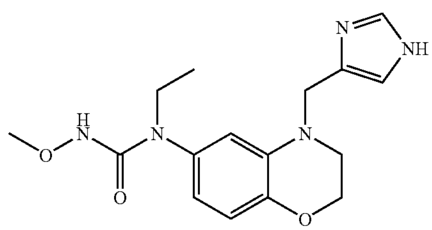 | 332 |
| 245 | 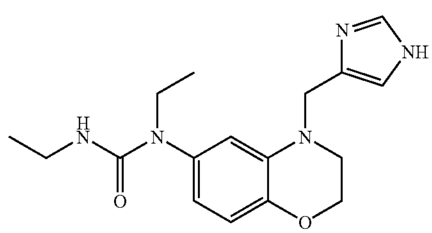 | 330 |
| 246 | 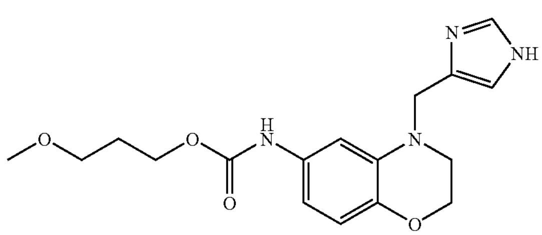 | 347 |
| 247 | 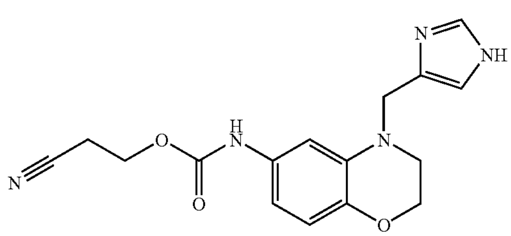 | 328 |

-continued

| Cpd | Structure | MS (MH+) |
|---|---|---|
| 248 | 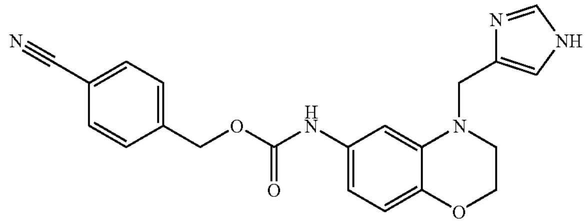 | 390 |
| 249 | 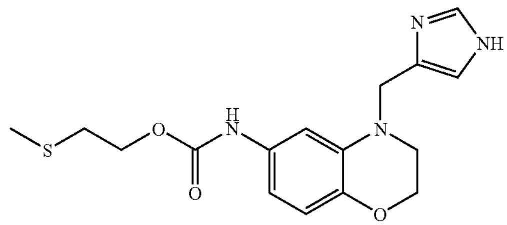 | 349 |
| 250 | 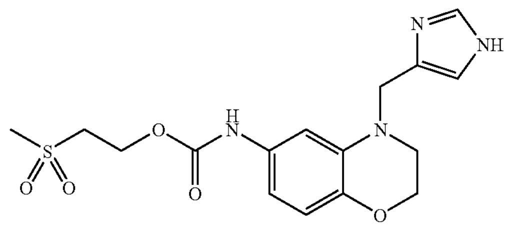 | 381 |
| 251 | 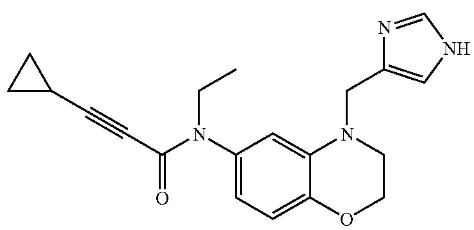 | 351 |
| 252 | 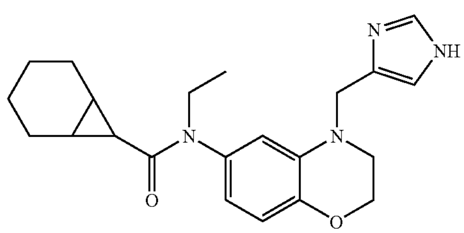 | 381 |
| 253 | 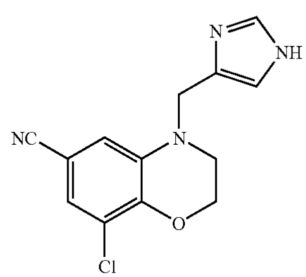 | 275 |

| Cpd | Structure | MS (MH+) |
|-----|-----------|----------|
| 254 | 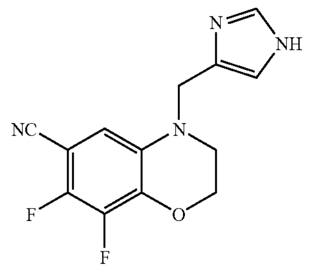 | 277 |
| 255 | 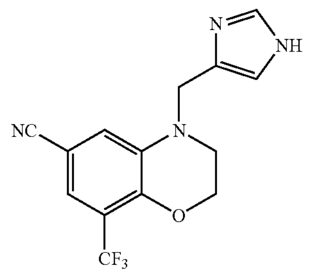 | 309 |
| 256 | 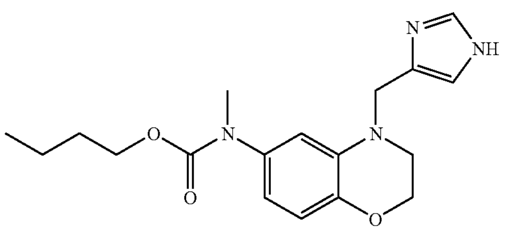 | 345 |
| 257 | 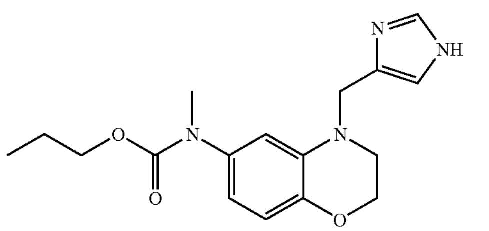 | 331 |
| 258 | 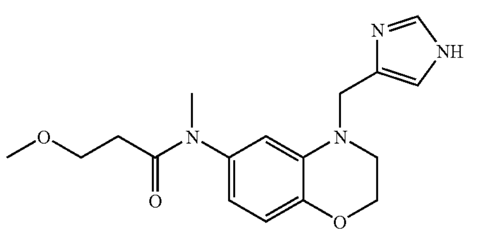 | 331 |
| 259 | 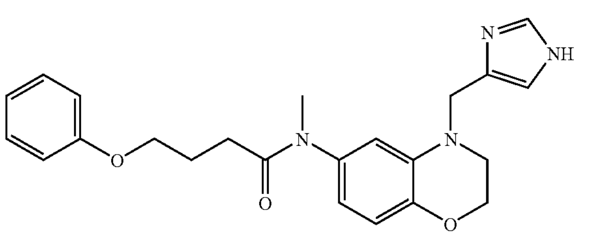 | 407 |

| Cpd | Structure | MS (MH+) |
|---|---|---|
| 260 | 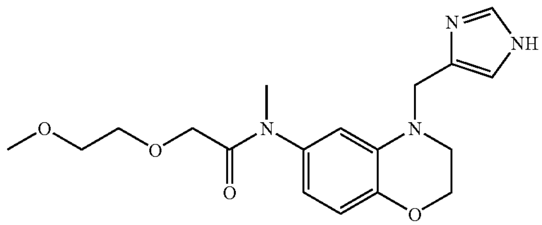 | 361 |
| 261 | 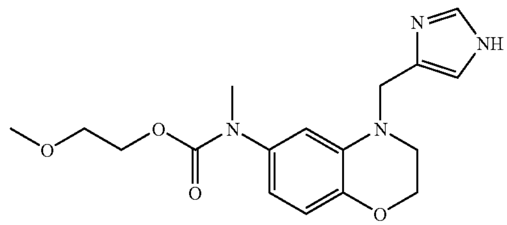 | 247 |
| 262 | 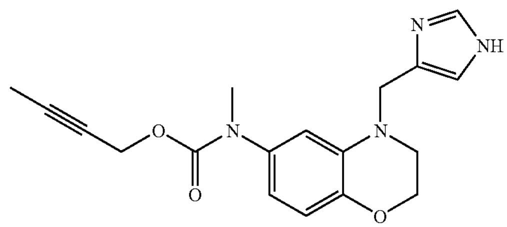 | 341 |
| 263 | 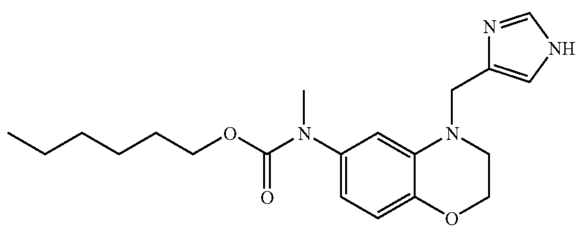 | 373 |
| 264 | 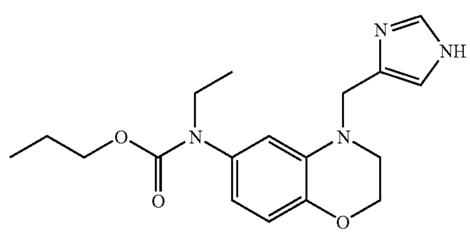 | 345 |
| 265 | 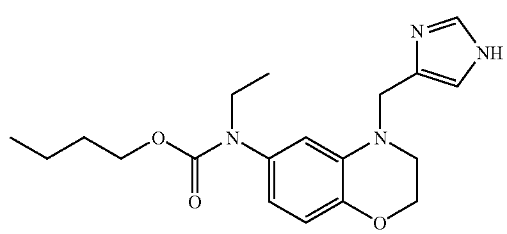 | 359 |

| Cpd | Structure | MS (MH+) |
|---|---|---|
| 266 | 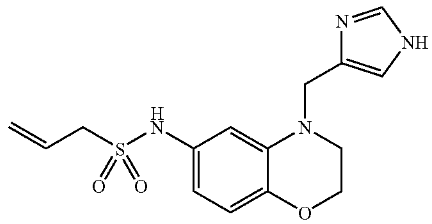 | 335 |
| 267 | 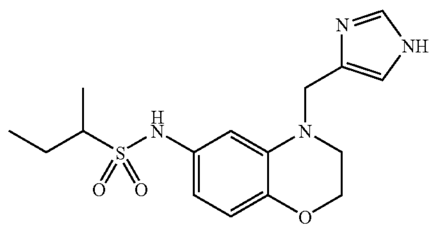 | 351 |
| 268 | 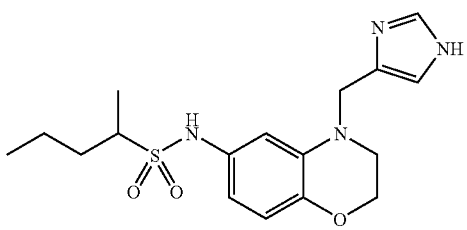 | 365 |
| 269 | 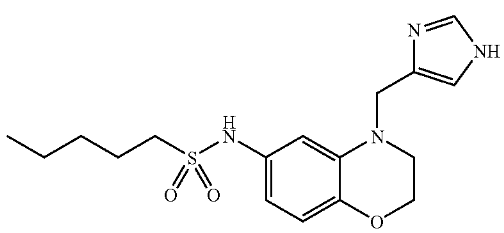 | 365 |
| 270 | 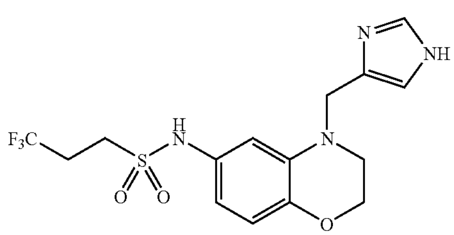 | 391 |
| 271 | 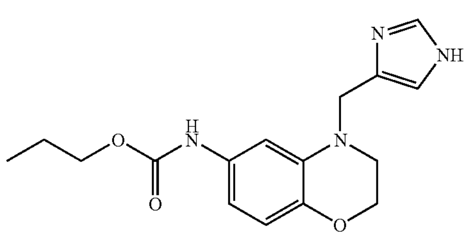 | 317 |

| Cpd | Structure | MS (MH+) |
|---|---|---|
| 272 | 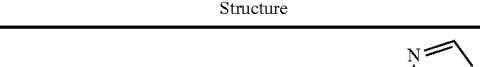 | 331 |

Assay:

Efficacy agonist activity values ($E_{max}$, GTPγS assay) for α2C were determined by following the general procedure detailed by Umland et. al ("Receptor reserve analysis of the human $α_{2c}$-adrenoceptor using [$^{35}$S]GTPγS and cAMP functional assays" European Journal of Pharmacology 2001, 411, 211-221). For the purposes of the present invention, a compound is defined to be an active agonist of the α2C receptor subtype if the compound's efficacy at the α2C receptor is $≧30\%$ $E_{max}$ (GTPγS assay). A compound is a functionally selective agonist of the α2C receptor subtype over the α2A receptor subtype if the compound's efficacy at the α2C receptor is $≧30\%$ $E_{max}$ (GTPγS assay) and its efficacy at the α2A receptor is $≧30\%$ $E_{max}$ (GTPγS assay).

The following compounds were evaluated to be active or functionally selective agonists of the α2C receptor subtype based on the previously defined definition: 1, 3, 3D, 3E, 5, 6, 6E, 7, 8, 9E, 9G, 9I, 9K, 9L, 9M, 9N, 9P, 9Q, 9R, 9S, 12, 13, 14, 14B 15, 19, 19D, 20, 21, 22, 24, 24D, 25B, 26, 26A, 26B, 27E, 28, 28D, 29, 30, 37, 38, 46, 51, 53, 54, 55, 57, 58, 114, 117, 124, 125, 129, 130, 132, 134, 135, 137, 139, 142, 144, 145, 148, 151, 152, 158, 159, 160, 162, 163, 164, 165, 167, 168, 169, 171, 178, 181, 218, 223, 231, 232, 235, 236, 238, 239, 240, 242, 243, 244, 245, 246, 247, 248, 249, and 250.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound represented by the structural formula:

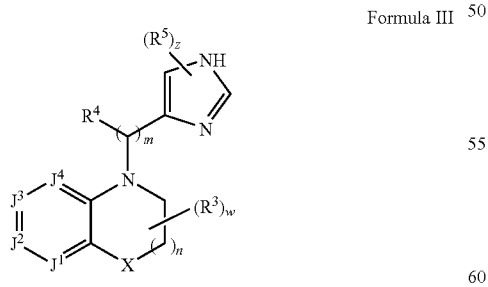

Formula III or a pharmaceutically acceptable salt of said compound, wherein:
X is —O—;
$J^1$, $J^2$, $J^3$, and $J^4$ are independently —C($R^2$)—;
$R^2$ is independently selected from the group consisting of H, —OH, halo, —CN, —NO$_2$, —(CH$_2$)$_q$YR$^7$, —(CH$_2$)$_q$NR$^7$YR$^{7'}$, —(CH$_2$)$_q$OR$^7$, —(CH$_2$)$_q$ON=CR$^7$R$^{7'}$, —P(=O)(OR$^7$)(O R$^{7'}$), —P(=O)(NR$^7$R$^{7'}$)$_2$, —P(=O)R$^8$$_2$, and alkyl, alkoxy, alkenyl, alkynyl, cycloalkyl, aryl, arylalkyl, heteroaryl, heteroarylalkyl, and heterocyclyl groups optionally substituted with at least one $R^5$;

Y is selected from the group consisting of a bond, —C(=O)—, —C(=O)NR$^7$—, —C(=O)O—, —C(=NR$^7$)—, —C(=NOR$^7$)—, —C(=NR$^7$)NR$^7$—, —C(=NR$^7$)NR$^7$O—, —S(O)$_p$—, SO$_2$NR$^7$—, and —C(S)NR$^7$—;

$R^3$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^4$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^5$ is independently selected from the group consisting of H, halo, —OH, —CN, —NO$_2$, —NR$^7$R$^{7'}$, —SR$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents;

$R^7$ is independently selected from the group consisting of H and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —SR$^{11}$ substituents;

$R^{7'}$ is independently selected from the group consisting of selected from the group consisting of H and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —SR$^{11}$ substituents; or $R^7$ and $R^{7'}$ together with the nitrogen atom to which they are attached form a 3- to 8-membered heterocyclyl, heterocyclenyl or heteroaryl ring having, in addition to the N atom, 1 or 2 additional hetero atoms selected from the group consisting of O, N, —N(R$^9$)— and S, wherein said rings are optionally substituted by 1 to 5 independently selected $R^5$ moieties, R[8] is independently selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R[11])$_2$, and —SR[11] substituents;

R[9] is independently selected from the group consisting of H, —C(O)—R[10], —C(O)—OR[10], and —S(O)$_p$—OR[10] and alkyl, alkenyl, alkynyl, cycloalkyl, aryl, arylalkyl, heteroaryl, nd heteroarylalkyl groups, each of which is optionally substituted with at least one of halo, —OH, —CN, —NO$_2$, —N(R[11])$_2$, and —SR[11] substituents; and R[10] is selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R[11])$_2$, and —SR[11] substituents;

R[11] is a moiety independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

m is 1;
n is 1;
p is 0-2;
q is 0-6;
z is 0-3; and
w is 0-4.

2. The Compound of claim 1 wherein J$^1$, J$^2$, and J$^4$ are C—H, J$^3$ is —CR$^1$ and R$^1$ is selected from the group consisting of H, —OH, halo, —CN, —NO$_2$, —SR$^7$—(CH$_2$)$_q$YR$^7$, —(CH$_2$)$_q$NR$^7$YR$^{7'}$, —(CH$_2$)$_q$OYR$^7$, —(CH$_2$)$_q$ON=CR$^7$R$^{7'}$, —P(=O)(OR$^7$)(OR$^{7'}$), —P(=O)(NR$^7$R$^{7'}$)$_2$, —P(=O)R$^8$$_2$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$.

3. The compound of claim 2 wherein R$^4$ is H.
4. The compound of claim 2, wherein R$^4$ is H.
5. The compound of claim 2, wherein R$^1$ is selected from the group consisting of —(CH$_2$)$_q$YR$^7$, —(CH$_2$)$_q$NR$^7$YR$^{7'}$, —(CH$_2$)$_q$OYR$^7$, and —(CH$_2$)$_q$ON=CR$^7$R$^{7'}$.

6. A compound selected from:

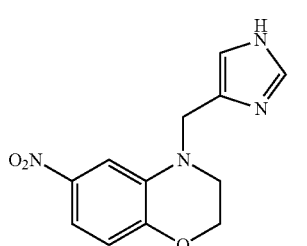

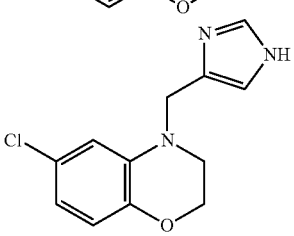

-continued

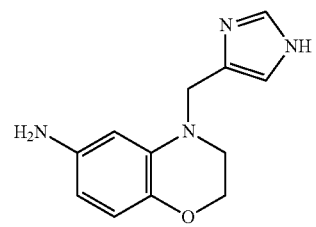

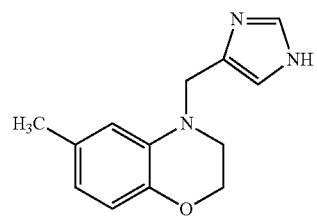

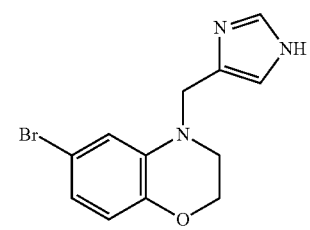

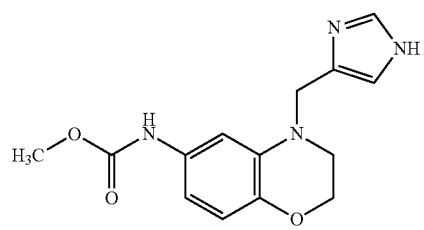

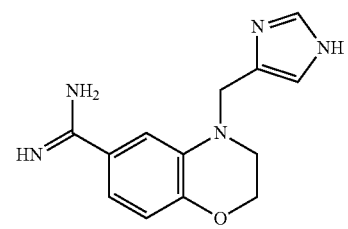

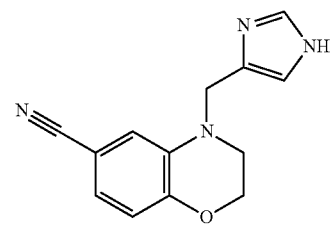

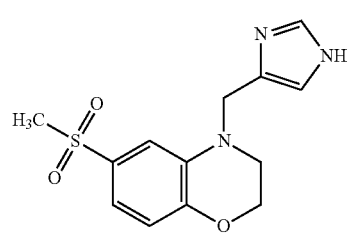

165
-continued
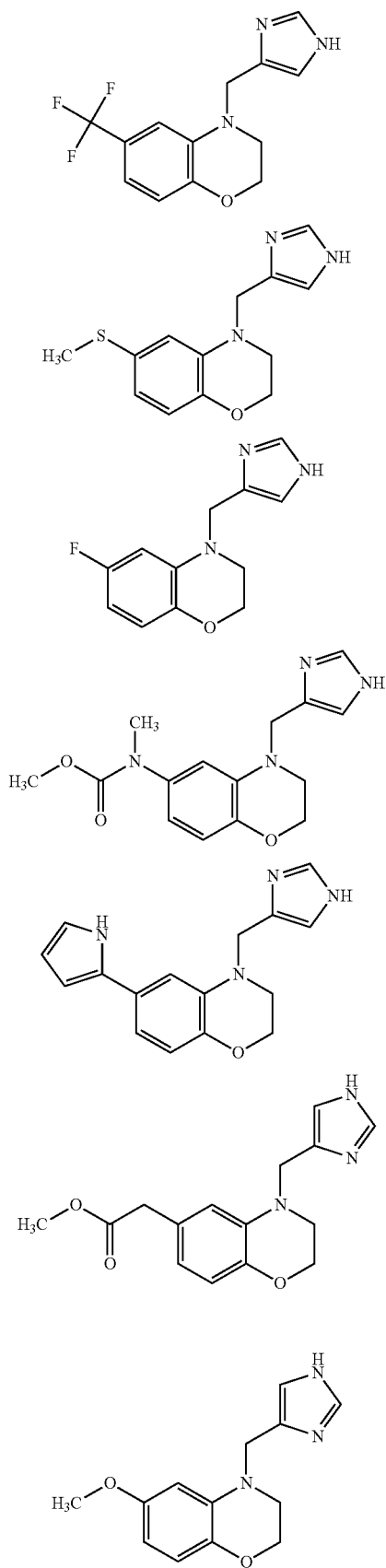
166
-continued
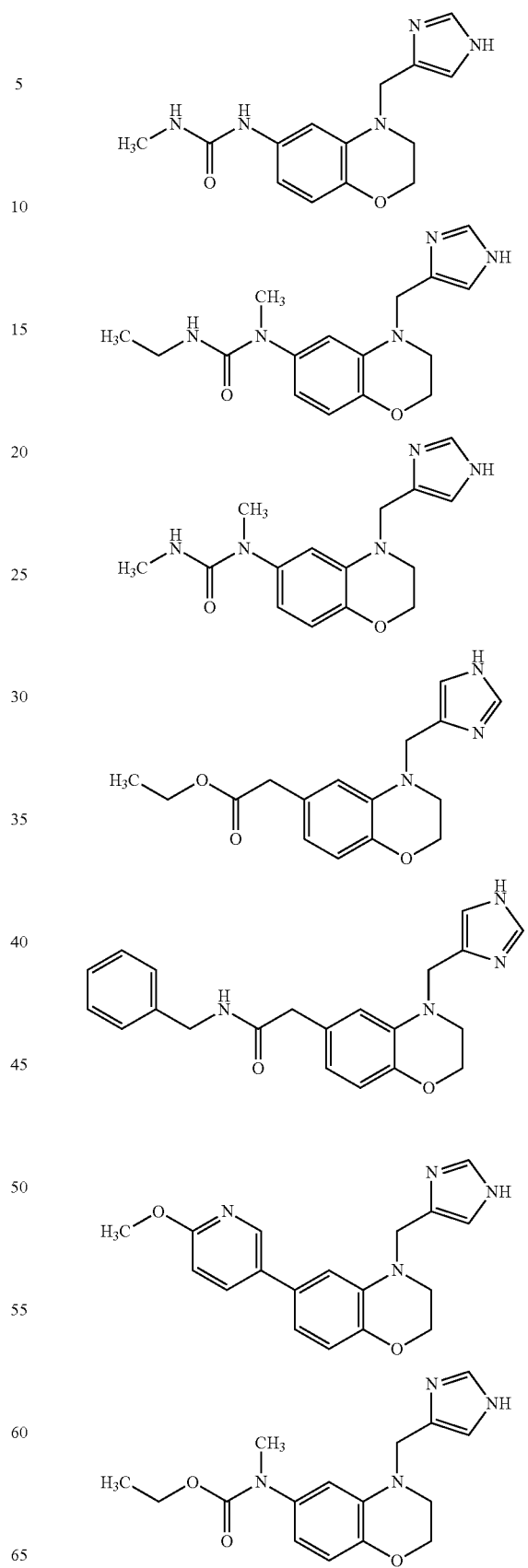

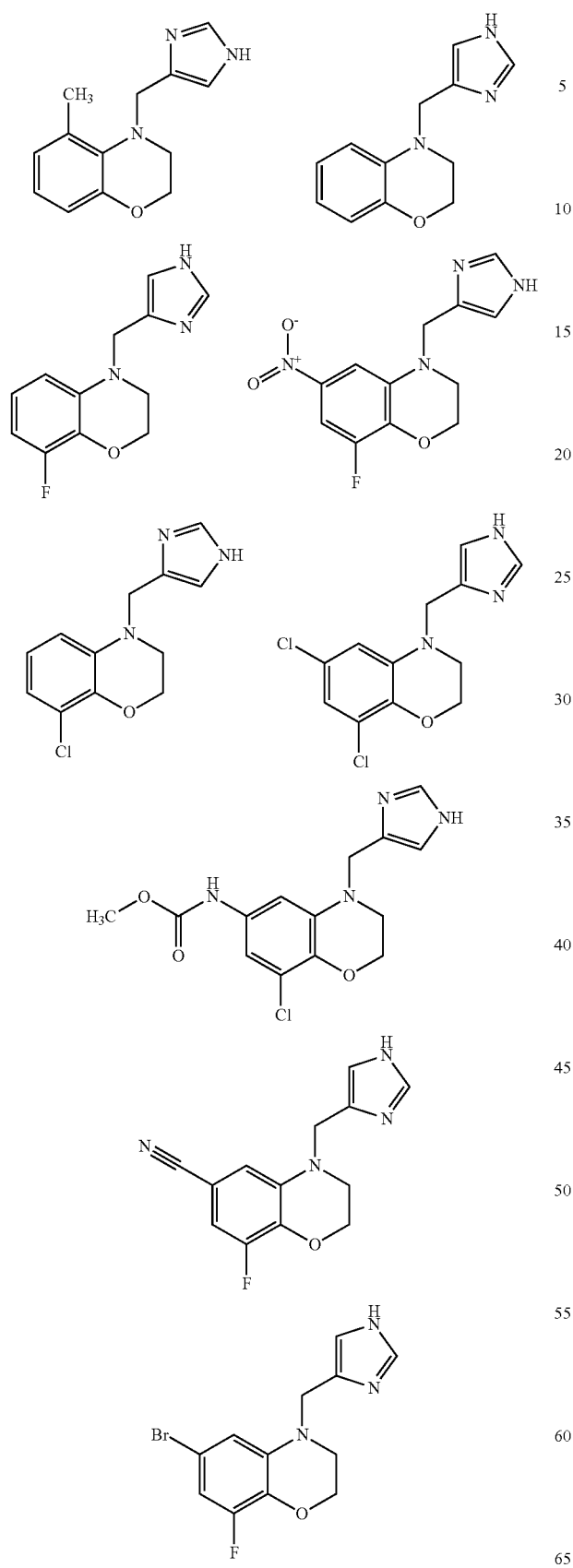
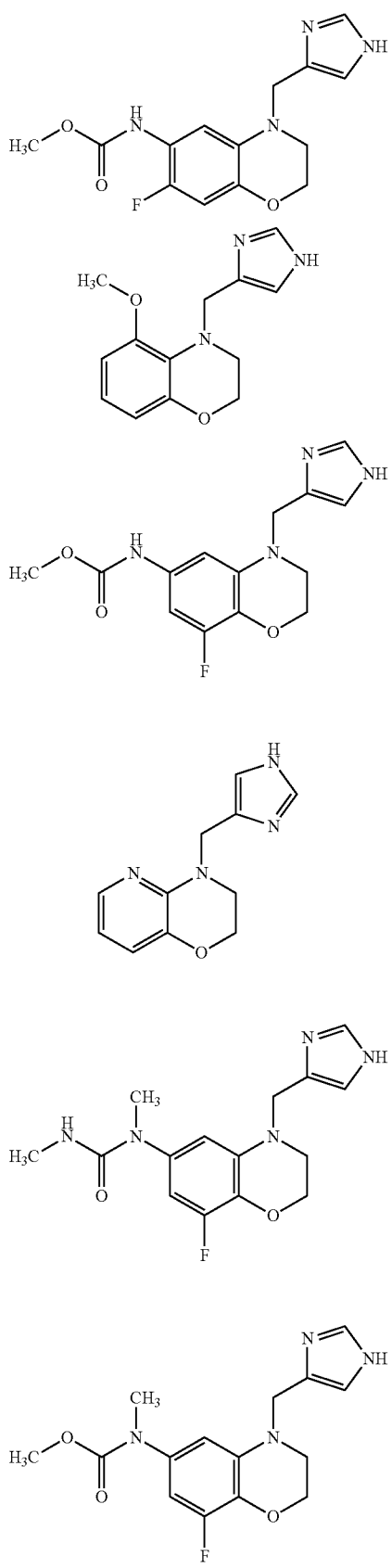

169
-continued
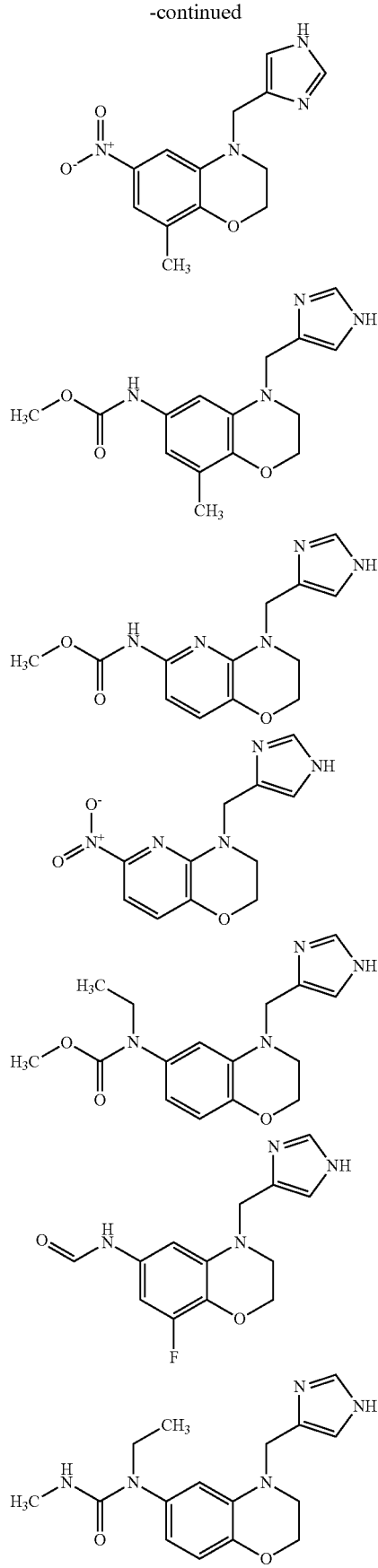
170
-continued
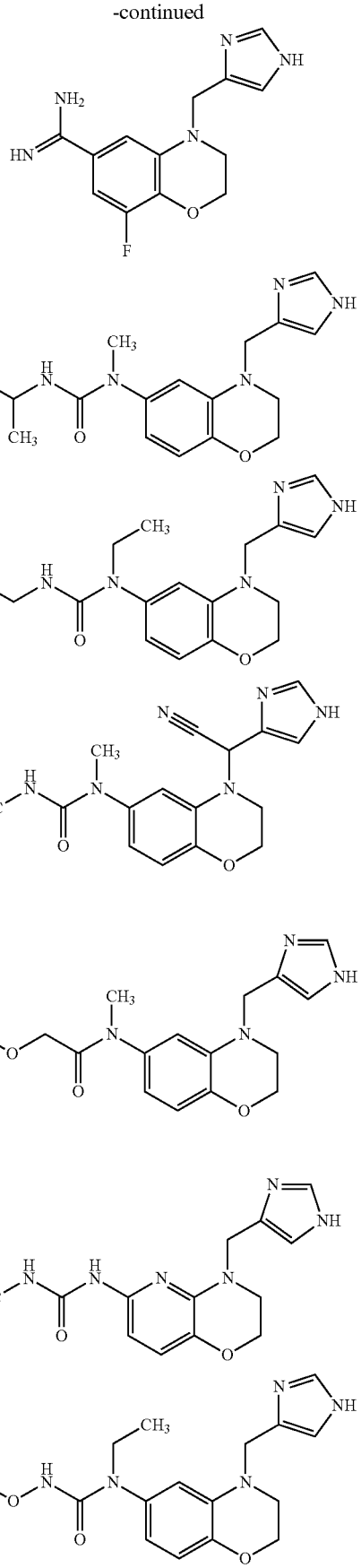

171
-continued
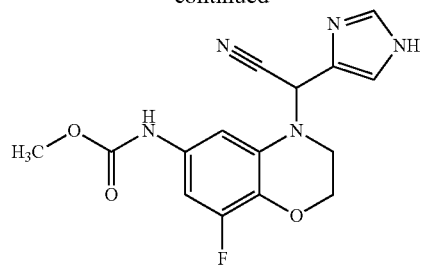
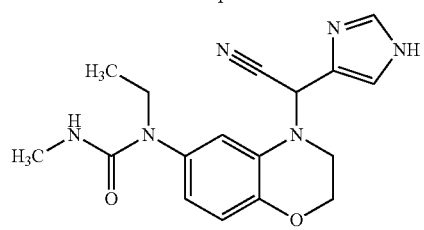
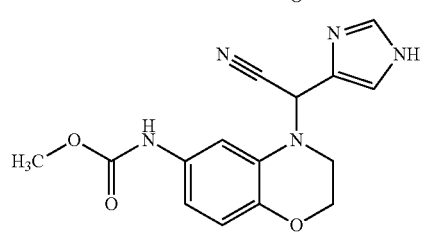
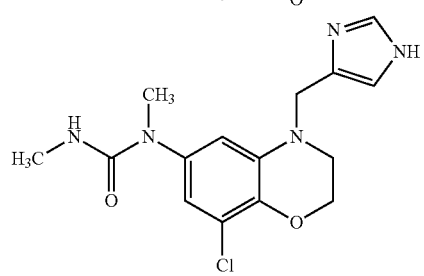
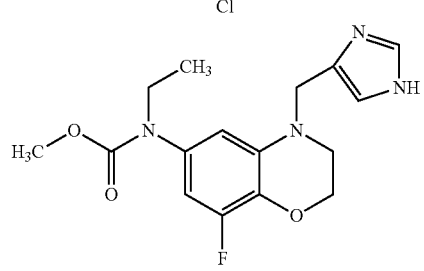
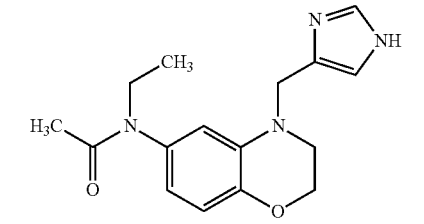
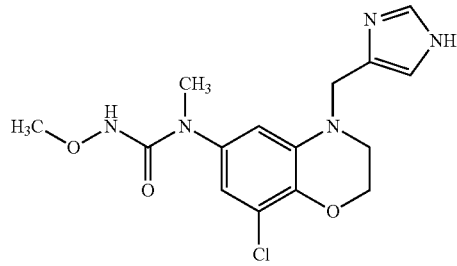
172
-continued
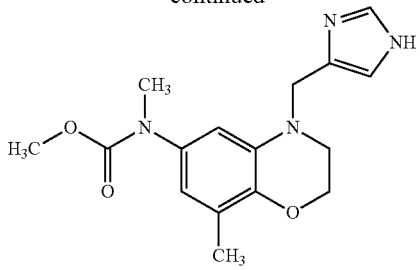
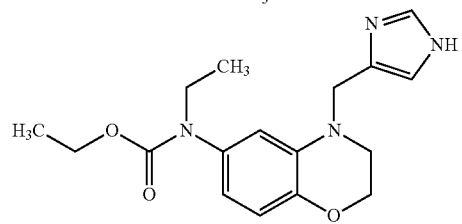
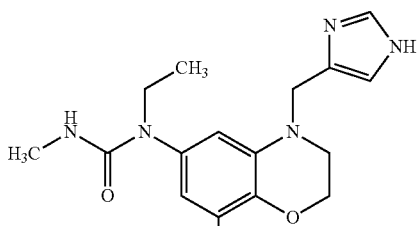
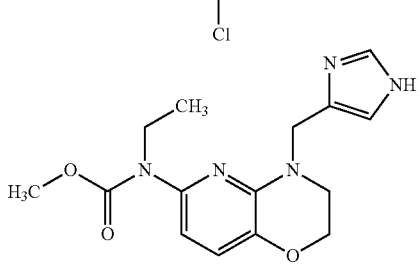
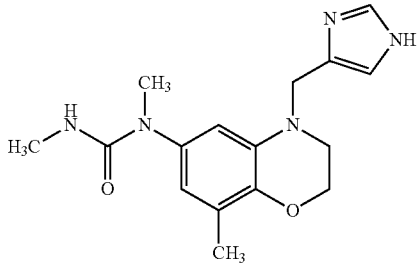
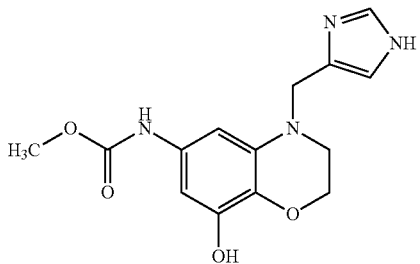
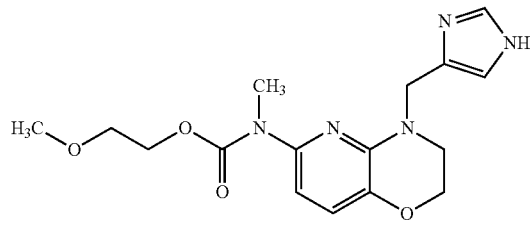

173
-continued
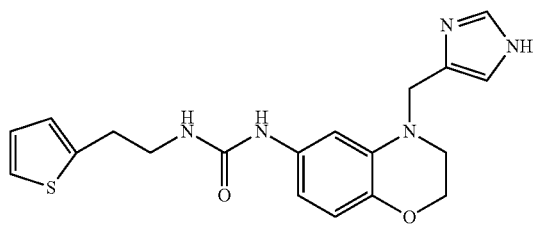
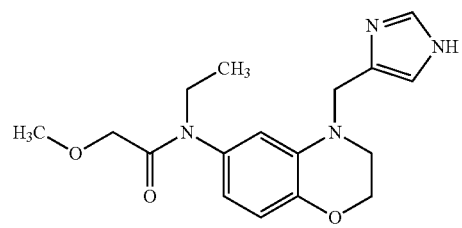
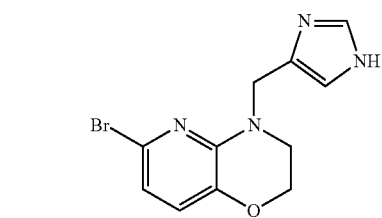
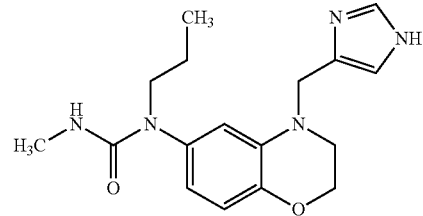
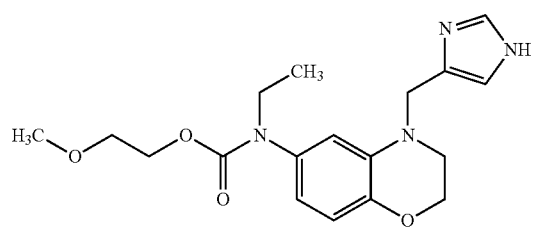
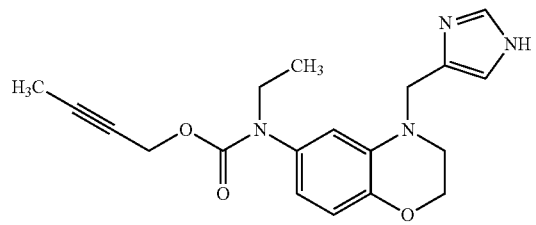
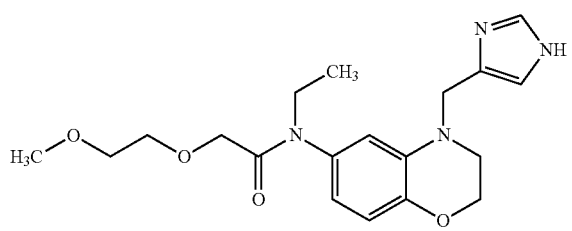
174
-continued
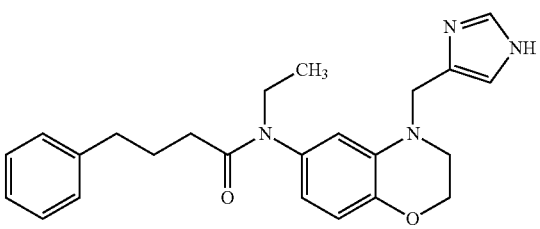
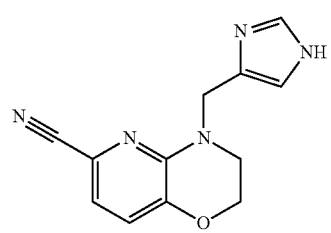
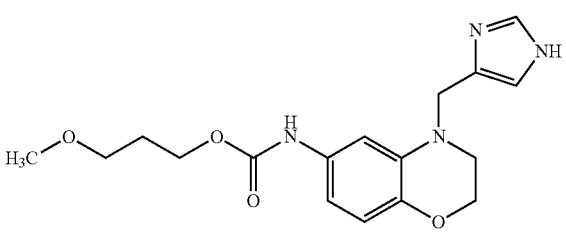
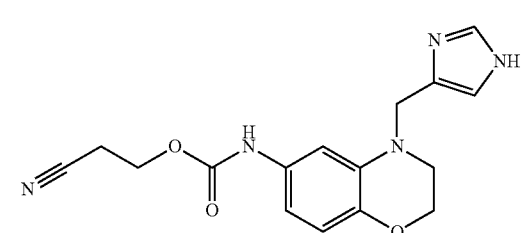
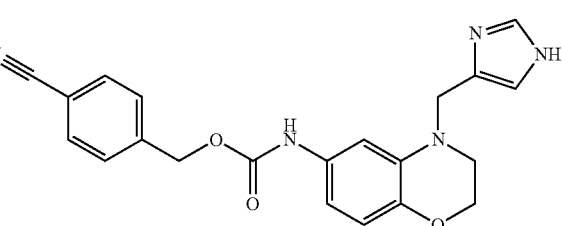

-continued

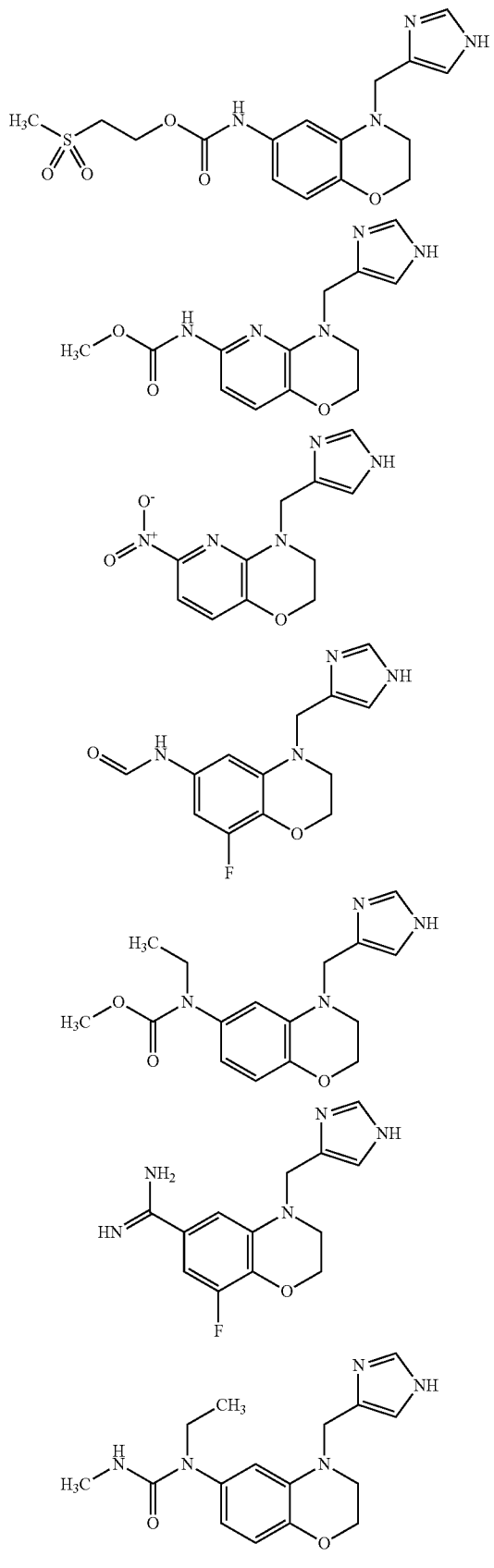

7. A pharmaceutical composition comprising at least one compound of claim 1, or a pharmaceutically acceptable salt thereof and at least one pharmaceutically acceptable carrier, adjuvant or vehicle.

8. A pharmaceutical composition comprising at least one compound of claim 6, or a pharmaceutically acceptable salt thereof and at least one pharmaceutically acceptable carrier, adjuvant or vehicle.

9. The pharmaceutical composition of claim 7, wherein said additional therapeutic agents are selected from the group consisting of anti-inflammatory steroids, PDE-4 inhibitors, anti-muscarinic agents, cromolyn sodium, $H_1$ receptor antagonists, 5-$HT_1$ agonists, NSAIDs, angiotensin-converting enzyme inhibitors, angiotensin II receptor agonists, β-blockers, β-agonists, leukotriene antagonists, diuretics, aldosterone antagonists, ionotropic agents, natriuretic peptides, pain management agents, anti-anxiety agents, anti-migraine agents, and therapeutic agents suitable for treating heart conditions, psychotic disorders, and glaucoma.

10. The pharmaceutical composition of claim 8, wherein said additional therapeutic agents are selected from the group consisting of steroids, PDE-4 inhibitors, anti-muscarinic agents, cromolyn sodium, $H_1$ receptor antagonists, 5-$HT_1$ agonists, NSAIDs, angiotensin-converting enzyme inhibitors, angiotensin II receptor agonists, β-blockers, β-agonists, leukotriene antagonists, diuretics, aldosterone antagonists, ionotropic agents, natriuretic peptides, pain management agents, anti-anxiety agents, anti-migraine agents, and therapeutic agents suitable for treating heart conditions, psychotic disorders, and glaucoma.

11. A compound of claim 1, in isolated and purified form.

12. A compound of claim 1 having the formula:

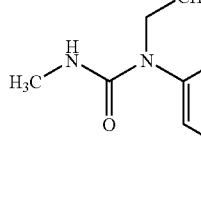

13. A compound of claim 1 having the formula:

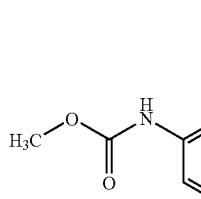

or a pharmaceutically acceptable salt thereof.

14. A compound of claim 1 having the formula:
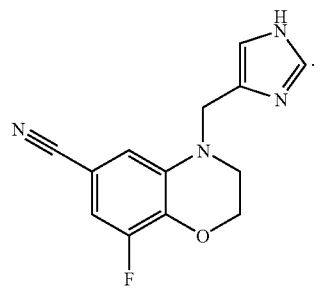
15. A compound of claim 1 having the formula:
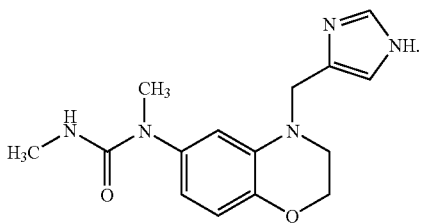
* * * * *